United States Patent
Iversen

(10) Patent No.: US 10,100,305 B2
(45) Date of Patent: Oct. 16, 2018

(54) METHODS AND COMPOSITIONS FOR MANIPULATING TRANSLATION OF PROTEIN ISOFORMS FROM ALTERNATIVE INITIATION OF START SITES

(75) Inventor: Patrick L. Iversen, Corvallis, OR (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/232,858

(22) PCT Filed: Jul. 13, 2012

(86) PCT No.: PCT/US2012/046783
§ 371 (c)(1),
(2), (4) Date: Apr. 17, 2014

(87) PCT Pub. No.: WO2013/012752
PCT Pub. Date: Jan. 24, 2013

(65) Prior Publication Data
US 2014/0296321 A1  Oct. 2, 2014

Related U.S. Application Data

(60) Provisional application No. 61/508,558, filed on Jul. 15, 2011.

(51) Int. Cl.
C12N 15/11 (2006.01)
C12N 15/113 (2010.01)

(52) U.S. Cl.
CPC .......... *C12N 15/113* (2013.01); *C12N 15/111* (2013.01); C12N 2310/11 (2013.01); C12N 2310/3233 (2013.01); C12N 2310/3513 (2013.01); C12N 2320/12 (2013.01); C12N 2320/34 (2013.01)

(58) Field of Classification Search
None
See application file for complete search history.

(56) References Cited

U.S. PATENT DOCUMENTS

| | | |
|---|---|---|
| 3,420,788 A | 1/1969 | Solms |
| 3,426,011 A | 2/1969 | Parmerter et al. |
| 3,453,257 A | 7/1969 | Parmerter et al. |
| 3,453,259 A | 7/1969 | Parmerter et al. |
| 3,459,731 A | 8/1969 | Gramera et al. |
| 4,235,871 A | 11/1980 | Papahadjopoulos et al. |
| 4,737,323 A | 4/1988 | Martin et al. |
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,539,082 A | 7/1996 | Nielsen et al. |
| 5,698,685 A | 12/1997 | Summerton et al. |
| 5,714,331 A | 2/1998 | Buchardt et al. |
| 5,719,262 A | 2/1998 | Buchardt et al. |
| 6,245,747 B1 | 6/2001 | Porter et al. |
| 6,670,461 B1 | 12/2003 | Wengel et al. |
| 6,692,911 B2 | 2/2004 | Pack et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,070,807 B2 | 7/2006 | Mixson |
| 7,084,125 B2 | 8/2006 | Wengel |
| 7,125,994 B2 | 10/2006 | Kim et al. |
| 7,145,006 B2 | 12/2006 | Kim et al. |
| 7,163,695 B2 | 1/2007 | Mixson |
| 7,179,896 B2 | 2/2007 | Kim et al. |
| 7,211,668 B2 | 5/2007 | Kim et al. |
| 7,517,644 B1 * | 4/2009 | Smith .................. 435/6.12 |
| 7,569,575 B2 | 8/2009 | Sorensen et al. |
| 7,572,582 B2 | 8/2009 | Wengel et al. |
| 7,943,762 B2 | 5/2011 | Weller et al. |
| 2005/0065171 A1 * | 3/2005 | Shakespeare et al. ... 514/263.22 |
| 2010/0048671 A1 * | 2/2010 | Qiu et al. .................. 514/44 A |

FOREIGN PATENT DOCUMENTS

| | | |
|---|---|---|
| EP | 0 798 386 B1 | 5/2004 |
| EP | 1 857 026 A1 | 11/2007 |
| FR | 2 774 274 A1 | 2/1998 |
| WO | 93/01286 A2 | 1/1993 |
| WO | 93/10932 A1 | 4/1996 |

(Continued)

OTHER PUBLICATIONS

Scrable et al, DELTA Np53 or p44: priming the p53 pump, 2005, International Journal of Biochemistry and Cell Biology, 37: 913-919.*
Abes et al., "Arginine-rich cell penetrating peptides: Design, structure-activity, and applications to alter pre-mRNA splicing by steric-block oligonucleotides," *J Pept Sci* 14:455-460, 2008.
Adorno et al., "A Mutant-p53/Smad Complex Opposes p63 to Empower TGFβ-Induced Metastasis," *Cell* 137:87-98, Apr. 3, 2009.
Banks et al., "Isolation of human-p53-specific monoclonal antibodies and their use in the studies of human p53 expression," *Eur J Biochem* 159:529-534, 1986.
Berge et al., "Pharmaceutical Salts," *Journal of Pharmaceutical Sciences* 66(1):1-18, Jan. 1977.
Blessed et al., "The Association Between Quantitative Measures of Dementia and of Senile Change in the Cerebral Grey Matter of Elderly Subjects," *Brit. J. Psychiat.* 114:797 -811, 1968.

(Continued)

*Primary Examiner* — Ekaterina Poliakova-Georgantas
(74) *Attorney, Agent, or Firm* — Seed Intellectual Property Law Group LLP

(57) ABSTRACT

Provided herein are antisense oligonucleotides, compositions comprising antisense oligonucleotides, and methods for the use of antisense oligonucleotides in manipulating translation. Expression of isoforms of proteins expressed from different start codons of the same transcript are inhibited by antisense oligonucleotides, which may also enhance expression of non-target isoforms.

23 Claims, 12 Drawing Sheets

Specification includes a Sequence Listing.

(56) References Cited

FOREIGN PATENT DOCUMENTS

| WO | 96/10390 A1 | 4/1996 |
|---|---|---|
| WO | 96/10391 A1 | 4/1996 |
| WO | 96/14057 A1 | 5/1996 |
| WO | 03/031612 A2 | 4/2003 |
| WO | 2008/002443 A1 | 1/2008 |
| WO | 2008/036127 A2 | 3/2008 |
| WO | 2009/064471 A1 | 5/2009 |
| WO | 2009/086469 A2 | 7/2009 |
| WO | 2010/120262 A1 | 10/2010 |
| WO | 2011/150408 A2 | 12/2011 |
| WO | 2013/112227 A1 | 8/2013 |

OTHER PUBLICATIONS

Bourdon et al., "p53 isoforms can regulate p53 transcriptional activity," *Genes & Developoment* 19:2122-2137, 2005.
Bunz et al., "Disruption of p53 in human cancer cells alters the responses to therapeutic agents," *J Clin Invest* 104(3):263-269, 1999.
Courtois et al., "ΔN-p53, a natural isoform of p53 lacking the first transactivation domain, counteracts growth suppression by wild-type p53," *Oncogene* 21:6722-6728, 2002.
Crum et al., "Population-based Norms for the Mini-Mental State Examination by Age and Educational Level," *JAMA* 269(18):2386-2391, 1993.
Dordunoo et al., "Preformulation Studies on Solid Dispersions Containing Triamterene or Temazepam in Polyethylene Glycols or Gelucire 44/14 for Liquid Filling of Hard Gelatin Capsules," *Drug Development and Industrial Pharmacy* 17(12):1685-1713, 1991.
Egholm et al., "PNA hybridizes to complementary oligonucleotides obeying the Watson-Crick hydrogen-bonding rules," *Nature* 365:566-568, Oct. 7, 1993.
Emerich et al., "Biocompatibility of Poly (DL-Lactide-co-Glycolide) Microspheres Implanted Into the Brain," *Cell Transplantation* 8:47-58, 1999.
Flaman et al., "The human tumour suppressor gene p53 is alternatively spliced in normal cells," *Oncogene* 12(4):813-818, 1996.
Ghosh et al., "Regulation of Human p53 Activity and Cell Localization by Alternative Splicing," *Molecular and Cellular Biology* 24(18):7987-7997, Sep. 2004.
Gregoriadis, *Drug Carriers in Biology and Medicine*, "Liposomes," pp. 288-341, Chapter Chapter 14, Academic Press, 1979.
Hames, eds., "Nucleic acid hybridization—a practical approach," IRL Press, Oxford, England 1985, pp. 107-108.
Hanson "Oligonucleotide Analogues Having Modified Intersubunit Linkages," U.S. Appl. No. 61/349,783, filed May 28, 2010.
Hanson et al., "Boronic Acid Conjugates of Oligonucleotide Analogues," U.S. Appl. No. 61/613,385, filed Mar. 20, 2012.
Hanson et al., "Functionally-Modified Oligonucleotides and Subunits Thereof," U.S. Appl. No. 61/561,805, filed Nov. 18, 2011.
Harlow et al., "Monoclonal Antibodies Specific for Simian Virus 40 Tumor Antigens," *Journal of Virology* 39(3):861-869, Sep. 1981.
Harms and Chen, "The functional domains in p53 family proteins exhibit both common and distinct properties," *Cell Death and Differentiation* 13:890-897, 2006.
Ishiwata et al., "Physical-Chemistry Characteristics and Biodistribution of Poly(ethylene glycol)-Coated Liposomes Using Poly(oxyethylene) Cholesteryl Ether," *Chem Pharm Bull* 43(6):1005-1011, Jun. 1995.
Iversen, "Phosphorodiamidate morpholino oligomers: Favorable properties for sequence-specific gene inactivation," *Current Opinion in Molecular Therapeutics* 3(3):235-238, 2001.
Kim et al., "Wild-type p53 in cancer cells: when a guardian turns into a blackguard," *Biochem Pharmacol* 77(1):11-20, Jan. 1, 2009.
Kokmen et al., "A Short Test of Mental Status: Description and Preliminary Results," *Mayo Clinic Proceedings* 62(4):281-288, Apr. 1987.
Koshkin et al., "LNA (Locked Nucleic Acids): Synthesis of the adenine, cytosine, quinine, 5-methylcytosine, thymine and uracil bicyclonucleoside monomers, oligomerisation, and unprecedented nucleic acid recognition," *Tetrahedron* 54(14):3607-3630, Apr. 2, 1998.
Lang et al., "Gain of Function of a p53 Hot Spot Mutation in a Mouse Model of Li-Fraumeni Syndrome," *Cell* 119:861-879, Dec. 17, 2004.
Lappalainen et al., "Cationic liposomes mediated delivery of antisense oligonucleotides targeted to HPV 16 E7 mRNA in CaSki cells," *Antiviral Research* 23:119-130, 1994.
Lasic et al., "Liposomes Revisited," *Science* 167:1275-1276, Mar. 3, 1995.
Lasic et al., "The 'Stealth' Liposome: A Prototypical Biomaterial," *Chemical Reviews* 95(8):2601-2628, Dec. 1995.
Liu et al., "Cationic Liposome-mediated Intravenous Gene Delivery," *The Journal of Biological Chemistry* 270(42):24864-24870, Oct. 20, 1995.
Liu et al., "Efficient and Isoform-Selective Inhibition of Cellular Gene Expression by Peptide Nucleic Acids," *Biochemistry* 43:1921-1927, 2004.
Mackereth et al., "Zebrafishpax8 is required for otic placode induction and plays a redundant role with Pax2 genes in the maintenance of the otic placode," *Development* 132(2):371-382, Jan. 2005.
Maier et al., "Modulation of mammalian life span by the short isoform of p53," *Genes & Development* 18:306-319, 2004.
Matsuda et al., "Determinants of Initiation Codon Selection during Translation in Mammalian Cells," *PLoS ONE* 5(11):e15057, Nov. 2010, 14 pages.
Miyada et al., "[6] Oligonucleotide Hybridization Techniques," *Methods in Enzymology* 154:94-107, 1987.
Nelson et al., "Arginine-Rich Peptide Conjugation to Morpholino Oligomers: Effects on Antisense Activity and Specificity," *Bioconjugate Chem* 16:959-966, 2005.
New, *Liposomes: A Practical Approach*, Chapter 2, "Preparation of Liposomes," pp. 33-104, IRL Press, 1990.
Obika et al., "Stability and structural features of the duplexes containing nucleoside analogues with a fixed N-type conformation, 2'-O,4'-C-methylribonucleosides," *Tetrahedron Letters* 39:5401-5404, 1998.
Obika et al., "Synthesis and properties of 3'-amino-2',4'-BNA, a bridge nucleic acid with a N3'→P5' phosphoramidate linkage," *Bioorganic & Medicinal Chemistry* 16:9230-9237, 2008.
Obika et al., "Synthesis of 2'-O,4'-C-Methyleneuridine and -cytidine. Novel Bicyclic Nucleosides Having a Fixed $C_3$,-endo Sugar Puckering," *Tetrahedron Letters* 38(50):8735-8738, 1997.
Oku et al., "Real-time analysis of liposomal trafficking in tumor-bearing mice by use of positron emission tomography," *Biochimica et Biophysica Acta* 1238:86-90, 1995.
Olive et al., "Mutant p53 Gain of Function in Two Mouse Models of Li-Fraumeni Syndrome," *Cell* 119:847-860, Dec. 17, 2004.
Pfeffer et al., "Measurement of Functional Activities in Older Adults in the Community," *J. Gerontology* 37(3): 323-329, 1982.
Ray et al., "Two internal ribosome entry sites mediate the translation of p53 isoforms," *EMBO Reports* 7(4):404-410, 2006.
Rovinski et al., "Deletion of 5'-Coding Sequences of the Cellular p53 Gene in Mouse Erythroleukemia: a Novel Mechanism of Oncogene Regulation," *Molecular and Cellular Biology* 7(2):847-853, Feb. 1987.
Schroeder et al., "Diffusion enhancement of drugs by loaded nanoparticles in vitro," *Progress in Neuro-Psychopharmacology and Biological Psychiatry* 23(5):941-949, Jul. 1999.
Sheen et al., "Bioavailability of a Poorly Water-Soluble Drug from Tablet and Solid Dispersion in Humans," *Journal of Pharmaceutical Sciences* 80(7):712-714, Jul. 1991.
Singh et al., "LNA (locked nucleic Acids): synthesis and high-affinity nucleic acid recognition," *Chemical Communications* 4:455-456, 1998.
Summerton et al., "Morpholino Antisense Oligomers: Design, Preparation, and Properties," *Antisense & Nucleic Acid Drug Development* 7:187-195, 1997.
Uhlmann et al., "Antisense Oligonucleotides: A New Therapeutic Principle," *Chemical Reviews* 90(4):544-584, Jun. 1990.

(56) References Cited

OTHER PUBLICATIONS

Vagnozzi et al., "Inhibition of Foot-and-Mouth Disease Virus Infections in Cell Cultures with Antisense Morpholino Oligomers," *Journal of Virology* 81(21):11669-11680, Nov. 2007.

Van Uden et al., "Cyclodextrins as a useful tool for bioconversions in plant cell biotechnology," *Plant Cell, Tissue and Organ Culture* 38(2-3):103-113, Sep. 1994.

Vousden et al., "Blinded by the Light: The Growing Complexity of p53," *Cell* 137:413-431, May 1, 2009.

Wang et al., "The P53 Pathway: Targets for the Development of Novel Cancer Therapies," *Cancer Treatment and Research* 119:175-181, 2004.

Wengel, "Synthesis of 3'-C- and 4'-C-Branched Oligodeoxynucleotides and the Development of Locked Nucleic Acid (LNA)," *Accounts of Chemical Research* 32(4):301-310, 1999.

Wenz, "Cyclodextrins as Building Blocks for Supramolecular Structures and Functional Units," *Agnew Chem Int Ed Engl* 33:803-822, 1994.

Williams et al., "Cationic lipids reduce time and dose of c-myc antisense oligodeoxynucleotides required to specifically inhibit Burkitt's lymphoma cell growth," *Leukemia* 10:1980-1989, 1996.

Wiman, "Strategies for therapeutic targeting of the p53 pathway in cancer," *Cell Death and Differentiation* 13:921-926, 2006.

Wu et al., "Cell-penetrating peptides as transporters for morpholino oligomers: effects of amino acid composition on intracellular delivery and cytotoxicity," *Nucleic Acids Research* 35(15):51828-5191, 2007.

Wu et al., "Receptor-mediated in Vitro Gene Transformation by a Soluble DNA Carrier System," *The Journal of Biological Chemistry* 262(10):4429-4432, Apr. 5, 1987.

Yin et al., "p53 Stability and activity is regulated by Mdm2-mediated induction of alternatives p53 translation products," *Nature Cell Biology* 4:462-467, 2002.

Zhu et al., "Identification of a Novel p53 Functional Domain That Is Necessary for Mediating Apoptosis," *J Biol Chem* 273(21):13030-13036, May 22, 1998.

Scrable et al., "DELTANp53 or p44: priming the p53 pump," *International Journal of Biochemistry and Cell Biology*, 37(5):913-919, May 1, 2005.

\* cited by examiner

SEQUENCE LISTING

<160> NUMBER OF SEQ ID NOS: 39

<210> SEQ ID NO 1
<211> LENGTH: 53
<212> TYPE: RNA
<213> ORGANISM: Homo sapiens

<400> SEQUENCE: 1
cugccuuccg ggucacugcc auggaggagc cgcagucaga uccuagcguc gag    53

<210> SEQ ID NO 2
<211> LENGTH: 53
<212> TYPE: RNA
<213> ORGANISM: Homo sapiens

<400> SEQUENCE: 2
cccccuugcc gucccaagca auggaugauu ugaugcuguc cccggacgau auu    53

<210> SEQ ID NO 3
<211> LENGTH: 22
<212> TYPE: DNA
<213> ORGANISM: Artificial Sequence
<220> FEATURE:
<223> OTHER INFORMATION: p53 targeting oligonucleotide

<400> SEQUENCE: 3
gcggctcctc catggcagtg ac    22

<210> SEQ ID NO 4
<211> LENGTH: 22
<212> TYPE: DNA
<213> ORGANISM: Artificial Sequence
<220> FEATURE:
<223> OTHER INFORMATION: p53 targeting oligonucleotide

<400> SEQUENCE: 4
catcaaatca tccattgctt gg    22

<210> SEQ ID NO 5
<211> LENGTH: 20
<212> TYPE: DNA
<213> ORGANISM: Artificial Sequence
<220> FEATURE:
<223> OTHER INFORMATION: p53 targeting oligonucleotide

<400> SEQUENCE: 5
agtttccata ggtctgaaaa    20

<210> SEQ ID NO 6
<211> LENGTH: 20
<212> TYPE: DNA
<213> ORGANISM: Artificial Sequence
<220> FEATURE:
<223> OTHER INFORMATION: p53 targeting oligonucleotide
<220> FEATURE:
<221> NAME/KEY: modified_base
<222> LOCATION: (2)...(4)
<223> OTHER INFORMATION: I
<220> FEATURE:
<221> NAME/KEY: modified_base
<222> LOCATION: 15
<223> OTHER INFORMATION: I

<400> SEQUENCE: 6
gnnnactgta gatgngtgaa    20

```
<210> SEQ ID NO 7
<211> LENGTH: 20
<212> TYPE: DNA
<213> ORGANISM: Artificial Sequence
<220> FEATURE:
<223> OTHER INFORMATION: p53 targeting oligonucleotide

<400> SEQUENCE: 7
cggataagat gctgaggagg                                                    20

<210> SEQ ID NO 8
<211> LENGTH: 19
<212> TYPE: DNA
<213> ORGANISM: Artificial Sequence
<220> FEATURE:
<223> OTHER INFORMATION: p53 targeting oligonucleotide

<400> SEQUENCE: 8
gttgtagtgg atggtggta                                                     19

<210> SEQ ID NO 9
<211> LENGTH: 20
<212> TYPE: DNA
<213> ORGANISM: Artificial Sequence
<220> FEATURE:
<223> OTHER INFORMATION: p53 targeting oligonucleotide

<400> SEQUENCE: 9
ctggagtctt ccagtgtgat                                                    20

<210> SEQ ID NO 10
<211> LENGTH: 21
<212> TYPE: DNA
<213> ORGANISM: Artificial Sequence
<220> FEATURE:
<223> OTHER INFORMATION: p53 targeting oligonucleotide
<220> FEATURE:
<221> NAME/KEY: modified_base
<222> LOCATION: 4
<223> OTHER INFORMATION: I

<400> SEQUENCE: 10
aagngtgaaa tattctccat c                                                  21

<210> SEQ ID NO 11
<211> LENGTH: 19
<212> TYPE: DNA
<213> ORGANISM: Artificial Sequence
<220> FEATURE:
<223> OTHER INFORMATION: p53 targeting oligonucleotide

<400> SEQUENCE: 11
gcgctcacgc ccacggatc                                                     19

<210> SEQ ID NO 12
<211> LENGTH: 20
<212> TYPE: DNA
<213> ORGANISM: Artificial Sequence
<220> FEATURE:
<223> OTHER INFORMATION: p53 targeting oligonucleotide

<400> SEQUENCE: 12
ccctgctccc ccctggctcc                                                    20

<210> SEQ ID NO 13
<211> LENGTH: 22
<212> TYPE: DNA
```

```
<213> ORGANISM: Artificial Sequence
<220> FEATURE:
<223> OTHER INFORMATION: p53 targeting oligonucleotide

<400> SEQUENCE: 13
tgccatcaac atatcttgat cg                                              22

<210> SEQ ID NO 14
<211> LENGTH: 9
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 14

Arg Arg Arg Gln Arg Arg Lys Lys Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 15

Arg Lys Lys Arg Arg Gln Arg Arg Arg
1               5

<210> SEQ ID NO 16
<211> LENGTH: 11
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 16

Arg Arg Arg Arg Arg Arg Arg Arg Arg Phe Phe
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 17

Arg Arg Arg Arg Arg Phe Phe Arg Arg Arg Arg
1               5                   10

<210> SEQ ID NO 18
<211> LENGTH: 4
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 18

Arg Arg Arg Arg
1
```

<210> SEQ ID NO 19
<211> LENGTH: 5
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 19

Arg Arg Arg Arg Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 20

Arg Arg Arg Arg Arg Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 21

Arg Arg Arg Arg Arg Arg Arg
1               5

<210> SEQ ID NO 22
<211> LENGTH: 8
<212> TYPE: PRT
<213> ORGANISM: Artifcial Sequence
<220> FEATURE:
<223> OTHER INFORMATION: Arginine-Rich Cell-Penetrating Peptide
      Transporter

<400> SEQUENCE: 22

Arg Arg Arg Arg Arg Arg Arg Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 23

Arg Arg Arg Arg Arg Arg Arg Arg Arg
1               5

<210> SEQ ID NO 24
<211> LENGTH: 16
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES

```
<222> LOCATION: 2, 4, 6, 8, 10, 12, 14, 16
<223> OTHER INFORMATION: Acp

<400> SEQUENCE: 24

Arg Xaa Arg Xaa Arg Xaa Arg Xaa Arg Xaa Arg Xaa Arg Xaa Arg Xaa
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES
<222> LOCATION: 2, 5, 8, 11
<223> OTHER INFORMATION: Acp

<400> SEQUENCE: 25

Arg Xaa Arg Arg Xaa Arg Arg Xaa Arg Arg Xaa Arg
1               5                   10

<210> SEQ ID NO 26
<211> LENGTH: 15
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES
<222> LOCATION: 2, 5, 8, 11, 14
<223> OTHER INFORMATION: Acp

<400> SEQUENCE: 26

Arg Xaa Arg Arg Xaa Arg Arg Xaa Arg Arg Xaa Arg Arg Xaa Arg
1               5                   10                  15

<210> SEQ ID NO 27
<211> LENGTH: 12
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES
<222> LOCATION: 2, 8
<223> OTHER INFORMATION: Acp
<220> FEATURE:
<221> NAME/KEY: MOD_RES
<222> LOCATION: 5, 11
<223> OTHER INFORMATION: bAla

<400> SEQUENCE: 27

Arg Xaa Arg Arg Xaa Arg Arg Xaa Arg Arg Xaa Arg
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 28

Arg Ala Arg Arg Ala Arg Arg Ala Arg Arg Ala Arg Phe Phe Cys
1               5                   10                  15
```

<210> SEQ ID NO 29
<211> LENGTH: 15
<212> TYPE: PRT
<213> ORGANISM: Artificial Sequence
<220> FEATURE:
<223> OTHER INFORMATION: Arginine-Rich Cell-Penetrating Peptide
    Transporter

<400> SEQUENCE: 29

Arg Gly Arg Arg Gly Arg Arg Gly Arg Arg Gly Arg Phe Phe Cys
 1               5                  10                  15

<210> SEQ ID NO 30
<211> LENGTH: 10
<212> TYPE: DNA
<213> ORGANISM: Homo Sapiens

<400> SEQUENCE: 30
tggctaaugc                                                                10

<210> SEQ ID NO 31
<211> LENGTH: 21
<212> TYPE: RNA
<213> ORGANISM: Homo Sapiens

<400> SEQUENCE: 31
aaggaaaaug gaugagacag a                                                   21

<210> SEQ ID NO 32
<211> LENGTH: 22
<212> TYPE: RNA
<213> ORGANISM: Homo Sapiens

<400> SEQUENCE: 32
cgacugcaga cccaugacaa ga                                                  22

<210> SEQ ID NO 33
<211> LENGTH: 10
<212> TYPE: PRT
<213> ORGANISM: Artificial Sequence
<220> FEATURE:
<223> OTHER INFORMATION: Fragment of exemplary "non-canonical" isoform

<400> SEQUENCE: 33

Ile Arg Gly Arg Glu Arg Phe Glu Met Phe
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: Fragment of exemplary "non-canonical" isoform

<400> SEQUENCE: 34

Asp Gln Thr Ser Phe Gln Lys Glu Asn Cys
 1               5                  10

<210> SEQ ID NO 35
<211> LENGTH: 15
<212> TYPE: PRT
<213> ORGANISM: Artificial Sequence
<220> FEATURE:
<223> OTHER INFORMATION: Fragment of exemplary "non-canonical" isoform

```
<400> SEQUENCE: 35

Ile Arg Gly Arg Glu Arg Phe Glu Met Phe Arg Glu Leu Asn Glu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Fragment of exemplary "non-canonical" isoform

<400> SEQUENCE: 36

Met Leu Leu Asp Leu Arg Trp Cys Tyr Phe Leu Ile Asn Ser Ser
1               5                   10                  15

<210> SEQ ID NO 37
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: (2)...(2)
<223> OTHER INFORMATION: Xaa = 6-aminohexanoic
<220> FEATURE:
<221> NAME/KEY: MOD_RES
<222> LOCATION: (5)...(5)
<223> OTHER INFORMATION: Xaa = 6-aminohexanoic
<220> FEATURE:
<221> NAME/KEY: MOD_RES
<222> LOCATION: (8)...(8)
<223> OTHER INFORMATION: Xaa = 6-aminohexanoic
<220> FEATURE:
<221> NAME/KEY: MOD_RES
<222> LOCATION: (11)...(11)
<223> OTHER INFORMATION: Xaa = 6-aminohexanoic
<220> FEATURE:
<221> NAME/KEY: MOD_RES
<222> LOCATION: (13)...(13)
<223> OTHER INFORMATION: Xaa = 6-aminohexanoic
<220> FEATURE:
<221> NAME/KEY: MOD_RES
<222> LOCATION: (14)...(14)
<223> OTHER INFORMATION: Xaa = beta-alanine

<400> SEQUENCE: 37

Arg Xaa Arg Arg Xaa Arg Arg Xaa Arg Arg Xaa Arg Xaa Xaa
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: (2)...(2)
<223> OTHER INFORMATION: Xaa = 6-aminohexanoic
<220> FEATURE:
<221> NAME/KEY: MOD_RES
<222> LOCATION: (5)...(5)
<223> OTHER INFORMATION: Xaa = beta-alanine
<220> FEATURE:
<221> NAME/KEY: MOD_RES
<222> LOCATION: (8)...(8)
<223> OTHER INFORMATION: Xaa = 6-aminohexanoic
<220> FEATURE:
<221> NAME/KEY: MOD_RES
<222> LOCATION: (11)...(11)
<223> OTHER INFORMATION: Xaa = beta-alanine
<220> FEATURE:
```

```
<221> NAME/KEY: MOD_RES
<222> LOCATION: (13)...(13)
<223> OTHER INFORMATION: Xaa = 6-aminohexanoic
<220> FEATURE:
<221> NAME/KEY: MOD_RES
<222> LOCATION: (14)...(14)
<223> OTHER INFORMATION: Xaa = beta-alanine

<400> SEQUENCE: 38

Arg Xaa Arg Arg Xaa Arg Arg Xaa Arg Arg Xaa Arg Xaa Xaa
 1               5                  10

<210> SEQ ID NO 39
<211> LENGTH: 17
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: (2)...(2)
<223> OTHER INFORMATION: Xaa = 6-aminohexanoic acid
<220> FEATURE:
<221> NAME/KEY: MOD_RES
<222> LOCATION: (4)...(4)
<223> OTHER INFORMATION: Xaa = 6-aminohexanoic acid
<220> FEATURE:
<221> NAME/KEY: MOD_RES
<222> LOCATION: (6)...(6)
<223> OTHER INFORMATION: Xaa = 6-aminohexanoic acid
<220> FEATURE:
<221> NAME/KEY: MOD_RES
<222> LOCATION: (8)...(8)
<223> OTHER INFORMATION: Xaa = 6-aminohexanoic acid
<220> FEATURE:
<221> NAME/KEY: MOD_RES
<222> LOCATION: (10)...(10)
<223> OTHER INFORMATION: Xaa = 6-aminohexanoic acid
<220> FEATURE:
<221> NAME/KEY: MOD_RES
<222> LOCATION: (12)...(12)
<223> OTHER INFORMATION: Xaa = 6-aminohexanoic acid
<220> FEATURE:
<221> NAME/KEY: MOD_RES
<222> LOCATION: (14)...(14)
<223> OTHER INFORMATION: Xaa = 6-aminohexanoic acid
<220> FEATURE:
<221> NAME/KEY: MOD_RES
<222> LOCATION: (16)...(16)
<223> OTHER INFORMATION: Xaa = 6-aminohexanoic acid
<220> FEATURE:
<221> NAME/KEY: MOD_RES
<222> LOCATION: (17)...(17)
<223> OTHER INFORMATION: Xaa = beta-alanine

<400> SEQUENCE: 39

Arg Xaa Arg Xaa Arg Xaa Arg Xaa Arg Xaa Arg Xaa Arg Xaa Arg Xaa
 1               5                  10                  15

Xaa
```

METHODS AND COMPOSITIONS FOR MANIPULATING TRANSLATION OF PROTEIN ISOFORMS FROM ALTERNATIVE INITIATION OF START SITES

CROSS-REFERENCE TO RELATED APPLICATION

The present application claims the benefit under 35 U.S.C. § 119(e) of U.S. Provisional Patent Application No. 61/508,558 filed on Jul. 15, 2011; which application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_493USPC_SEQUENCE_LISTING. The text file is about 10.3 KB, was created on Apr. 16, 2014, and is being submitted electronically via EFS web.

BACKGROUND

Technical Field

Provided herein are antisense oligonucleotides, compositions comprising antisense oligonucleotides, and methods for the use of antisense oligonucleotides in manipulating translation.

Description of the Related Art

The human genome is composed of approximately 28,000 genes from which approximately 150,000 proteins are derived. The mechanisms by which multiple proteins can be generated from a single gene include alternate use of promoters, splice sites, polyadenylation sites, translation initiation codons, RNA editing and selenocysteine insertion. In the case of alternate translation initiation start sites, a potential family of related proteins can be produced from a single transcript which can result in qualitative and quantitative differences in the expressed proteins. The biological significance of alternate translation start sites is determined by the differences in the peptide segment that is not shared by the two or more proteins derived from the same gene. The activity of one or more of such proteins may be associated with a disease.

In one example, the p53 tumor protein is translated as different isoforms with distinct biological effects. The p53 tumour suppressor gene encodes a transcription factor that is commonly inactivated in human cancer. In response to many forms of stress including DNA damage and replicative stress, p53 can regulate the expression of genes that block cell cycle progression or promote apoptosis, enabling p53 to eliminate premalignant cells that could otherwise give rise to cancer. As a result, much effort is directed at reconstituting or reactivating p53 expression in tumour cells that have undergone loss or missense mutation in p53.

p53, however, can also promote the repair and survival of damaged cells through a large number of mechanisms (see Kim et al., 2009; and Vousden and Prives, 2009). The dual function of p53 in promoting death or survival raises questions regarding the determinants that govern the cellular response to p53. The dual function of p53 must also be considered in the treatment of tumours that retain wild-type and even mutant p53 alleles.

Moreover, many isoforms of p53 exist, some of which may possess novel and unanticipated functions (see Harms and Chen, 2006). For instance, mouse p44 has both positive and negative effects on the transcription regulatory functions of p53 depending on the specific target gene (see Maier et al., 2004) and even though p53β/γ lacks the oligomerization domain and was reported to lack transcriptional activity, it retains the ability to bind certain p53-response elements on DNA (see Bourdon et al., 2005). It would be advantageous to interfere with p53-mediated survival in certain types of cancers, and to minimize induction of p53 isoforms having unanticipated activities There exists a need for compositions and methods for modulating the translation of protein isoforms associated with alternate translation initiation start sites, particularly in relation to disease-associated protein isoforms. The present invention meets this need and offers other related advantages.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

The present invention relates generally to the use of antisense oligonucleotides and related agents in compositions and methods for modulating the expression of protein isoforms translated from alternative translation initiation sites.

Therefore, in one aspect, provided herein is an isolated antisense oligonucleotide of 12 to 50 nucleotides in length, wherein the antisense oligonucleotide comprises a sequence substantially complementary to one or more translation start codons of an mRNA that encodes at least two cellular proteins translated from at least two translation start codons of said mRNA, wherein said oligonucleotide inhibits translation of one or more of said at least two cellular proteins. In some embodiments, the oligonucleotide selectively inhibits the translation of a first isoform relative to a second isoform. In some embodiments, this selective inhibition modulates the levels and/or ratios of the translation of a first isoform relative to a second isoform. In some embodiments, the isolated antisense oligonucleotide comprises a sequence substantially complementary to a translation start codon of an mRNA that encodes at least two cellular protein isoforms translated from at least two translation start codons of said mRNA, where said oligonucleotide inhibits translation of an isoform. In some embodiments, substantially complementary is 75% to 100% complementary. In some embodiments, said isoform is the most abundant isoform of the at least two cellular protein isoforms encoded by said mRNA. In some embodiments, said isoform is an aberrant isoform of a protein encoded by said mRNA. In some embodiments, said isoform and a second isoform of said at least two cellular protein isoforms have different intracellular localizations, and/or different cellular activities. In some embodiments, one of said isoform and said second isoform is secreted, and the other of said isoform and said second isoform is not secreted. In some embodiments, a second isoform of said at least two cellular protein isoforms comprises an N-terminal deletion relative to the isoform inhibited by said isolated antisense oligonucleotide. In some embodiments, the N-terminal deletion comprises a signal peptide. In some embodiments, the start codon is AUG, CUG, GUG, UUG, AUA, UUU, or ACG.

In some embodiments, the isolated antisense oligonucleotide comprises a sequence substantially complementary to a translation start codon of an mRNA that encodes at least two cellular protein isoforms translated from at least two translation start codons of said mRNA, wherein said oligonucleotide inhibits translation of a first isoform and increases translation of a second isoform. In some embodiments, substantially complementary is 75% to 100% complementary. In some embodiments, the first isoform is the most abundant isoform of the at least two cellular protein isoforms encoded by said mRNA. In some embodiments, the first isoform is an aberrant isoform of a protein encoded by said mRNA. In some embodiments, the first isoform and the second isoform have different intracellular localizations and/or different cellular activities. In some embodiments, one of said first isoform and said second isoform is secreted, and the other of said first isoform and said second isoform is not secreted. In some embodiments, said second isoform comprises an N-terminal deletion relative to said first isoform. In some embodiments, the N-terminal deletion comprises a signal peptide. In some embodiments, the start codon is AUG, CUG, GUG, UUG, AUA, UUU, or ACG.

In one aspect, provided herein is a method of inhibiting translation of a cellular protein translated from a start codon of an mRNA that encodes at least two cellular proteins translated from at least two start codons. In one aspect, provided herein is a method of inhibiting translation of an isoform of a cellular protein translated from a start codon of an mRNA that comprises at least two start codons. In some embodiments, the method comprises specifically hybridizing to said mRNA an antisense oligonucleotide of 12 to 50 nucleotides in lengths comprising a sequence substantially complementary to said translation start codon, wherein said antisense oligonucleotide inhibits translation of said isoform. In some embodiments, substantially complementary is 75% to 100% complementary. In some embodiments, said isoform is the most abundant isoform of the cellular protein. In some embodiments, said isoform is an aberrant isoform of said cellular protein. In some embodiments, said mRNA encodes a second isoform of said cellular protein, said second isoform having a different intracellular localization and/or a different cellular activity than the isoform inhibited by said antisense oligonucleotide. In some embodiments, said mRNA encodes a second isoform of said cellular protein, and one of said isoform inhibited by said antisense oligonucleotide and said second isoform is secreted, and the other of said isoform inhibited by said antisense oligonucleotide and said second isoform is not secreted. In some embodiments, said mRNA encodes a second isoform of said cellular protein comprising an N-terminal deletion relative to said isoform inhibited by said antisense oligonucleotide. In some embodiments, the N-terminal deletion comprises a signal peptide. In some embodiments, the start codon is AUG, CUG, GUG, UUG, AUA, UUU, or ACG. In some embodiments, the method further comprises hybridizing to said mRNA one or more additional antisense oligonucleotides, each additional antisense oligonucleotide complementary to an additional translation start codon of an additional isoform of said cellular protein encoded by said mRNA, wherein said hybridizing inhibits translation of each of said additional isoforms.

In one aspect, provided herein is a method of inhibiting a protein associated with a disease. In one aspect, provided herein is a method of inhibiting an isoform associated with a disease. In some embodiments, the method comprises administering to a subject an antisense oligonucleotide of 12 to 50 nucleotides in length comprising a sequence substantially complementary to a translation start codon of an mRNA that encodes a cellular protein having at least two isoforms, wherein said antisense oligonucleotide inhibits translation of an isoform. In some embodiments, substantially complementary is 75% to 100% complementary. In some embodiments, said isoform is the most abundant isoform of the cellular protein. In some embodiments, said isoform is an aberrant isoform of said cellular protein. In some embodiments, said mRNA encodes a second isoform of said cellular protein, said second isoform having a different intracellular localization and/or a different cellular activity than the isoform inhibited by said antisense oligonucleotide. In some embodiments, said mRNA encodes a second isoform of said cellular protein, and one of said isoform inhibited by said antisense oligonucleotide and said second isoform is secreted, and the other of said isoform inhibited by said antisense oligonucleotide and said second isoform is not secreted. In some embodiments, said mRNA encodes a second isoform of said cellular protein comprising an N-terminal deletion relative to said isoform inhibited by said antisense oligonucleotide. In some embodiments, the N-terminal deletion comprises a signal peptide. In some embodiments, the start codon is AUG, CUG, GUG, UUG, AUA, UUU, or ACG. In some embodiments, the disease is a proliferative disorder, Alzheimer's disease, diabetes, a neurodegenerative disorder, a TAR DNA-binding protein-43 (TBP-43) proteinopathy, amytrophic lateral sclerosis, or leukemia. In some embodiments, the method further comprises administering to said subject one or more additional antisense oligonucleotides, each additional antisense oligonucleotide complementary to an additional translation start codon of an additional isoform of said cellular protein encoded by said mRNA, wherein said additional antisense oligonucleotides inhibit translation of said additional isoforms.

In some embodiments, provided herein is a pharmaceutical composition comprising an isolated antisense oligonucleotide as described herein and a pharmaceutically acceptable carrier. In some embodiments, provided herein is a method of increasing translation of said second isoform comprising hybridizing an isolated antisense oligonucleotide as described herein to said start codon. In one aspect, provided herein is an antisense oligonucleotide of 12 to 50 nucleotides in length comprising a sequence substantially complementary to a translation start codon of an mRNA that encodes at least two cellular protein isoforms translated from at least two translation start codons of said mRNA for the treatment of a disease. Antisense oligonucleotides for use in the treatment of disease can be any antisense oligonucleotide provided herein. In some embodiments, the disease is a proliferative disorder, Alzheimer's disease, diabetes, a neurodegenerative disorder, a TAR DNA-binding protein-43 (TBP-43) proteinopathy, amytrophic lateral sclerosis, or leukemia.

In some embodiments of the methods and compositions provided herein, the mRNA encodes a member of a cell signaling pathway. In some embodiments, the mRNA encodes a mammalian protein, such as a human protein. In some embodiments, the mRNA encodes a viral protein, such as a foot-and-mouth disease protein. In some embodiments, the mRNA encodes a protein selected from the group consisting of p53, FGF2, VEGF-A, c-Myc, n-Myc, 1-Myc, LYL1, p15 INK4B, WT1, BAG1, NOD2, Caspase 8, Catechol O methyl transferase, EGF3, EIF4G1, GATA1, TRIIA-alpha, IL-1ra, MAP3K8, NFATC1, SHC, SOCS3, RAG1, IDE, TDP-43, and RGS2.

In some embodiments of the methods and compositions provided herein, the antisense oligonucleotide inhibits cell cycle progression. In some embodiments, the antisense oligonucleotide enhances sensitivity of tumor cells to chemotherapy. In some embodiments, the antisense oligonucleotide enhances sensitivity of tumor cells to radiation therapy. In some embodiments, the antisense oligonucleotide increases translation of a second isoform of the cellular protein. In some embodiments, the isolated antisense oligonucleotide further comprises one or more of (i) a backbone comprising morpholino subunits linked by phosphorous-containing intersubunit linkages; (ii) a peptide to which said isolated antisense oligonucleotide is conjugated; (iii) one or more positively charged backbone linkages; and (iv) one or more backbone linkages comprising a 4-piparazino group.

As described below, in various embodiments, the invention relates generally to antisense agents for modulating p53 expression, and methods of use thereof. For instance, certain embodiments include methods of increasing sensitivity of a cell to a chemotherapeutic, where the cell expresses full-length or mutant p53 or both, and where a predominant response of the cell to p53 expression, or p53 activation by the chemotherapeutic, is survival relative to cell-death, comprising contacting the cell with the chemotherapeutic and a nuclease-resistant antisense oligonucleotide of about 12-40 bases, where the chemotherapeutic is a DNA intercalating agent, a topoisomerase II inhibitor, or both, and where the antisense oligonucleotide reduces expression of full-length or mutant p53, thereby increasing sensitivity of the cell to the chemotherapeutic.

In certain embodiments, the antisense oligonucleotide is complementary to at least 12 bases of SEQ ID NO:1 (the region surrounding the AUG codon encoding for residue 1 of full-length p53). In some embodiments, the antisense oligonucleotide is complementary to the AUG start codon. In particular embodiments, the antisense oligonucleotides comprises a targeting sequence that is at least 90% identical to SEQ ID NO:3 (M1). In certain embodiments, the antisense oligonucleotide comprises the targeting sequence of SEQ ID NO:3 (M1). In certain embodiments, the antisense oligonucleotide consists of the targeting sequence of SEQ ID NO:3 (M1).

Some methods include contacting the cell with a second nuclease-resistant antisense oligonucleotide of about 12-30 bases, where the second oligonucleotide is complementary to at least 12 bases of SEQ ID NO:2 (the region surrounding the AUG codon encoding for residue 40 of full-length p53). In certain embodiments, the second antisense oligonucleotide is complementary to the AUG codon encoding for residue Met40 of full-length p53. In certain embodiments, the antisense oligonucleotides comprises a targeting sequence that is at least 90% identical to SEQ ID NO:4 (M40). In some embodiments, the antisense oligonucleotide comprises the targeting sequence of SEQ ID NO:4 (M40). In certain embodiments, the antisense oligonucleotide consists of the targeting sequence of SEQ ID NO:4 (M40). Particular embodiments comprise contacting the chemotherapeutic prior to, at the same time as, or after contacting the cell with the antisense oligonucleotide(s).

Also included are methods of reducing expression of full-length p53 and at least one ΔN-p53 isoform thereof in a cell, comprising contacting the cell with at least two nuclease-resistant antisense oligonucleotides of about 12-40 bases, where the first antisense oligonucleotide is complementary to at least 12 bases of SEQ ID NO:1 (the region surrounding the AUG codon encoding for residue 1 of full-length p53), and where the second oligonucleotide is complementary to at least 12 bases of SEQ ID NO:2 (the region surrounding the AUG codon encoding for residue 40 of full-length p53), thereby reducing expression of full-length p53 and the ΔN-p53 isoform thereof.

In certain embodiments, the first antisense oligonucleotide is complementary to the AUG start codon. In certain embodiments, the first antisense oligonucleotides comprises a targeting sequence that is at least 90% identical to SEQ ID NO:3 (M1). In certain embodiments, the first antisense oligonucleotide comprises the targeting sequence of SEQ ID NO:3 (M1). In certain embodiments, the first antisense oligonucleotide consists of the targeting sequence of SEQ ID NO:3 (M1). In some embodiments, the second antisense oligonucleotide is complementary to the AUG codon encoding for residue Met40 of full-length p53. In some embodiments, the antisense oligonucleotides comprises a targeting sequence that is at least 90% identical to SEQ ID NO:4 (M40). In some embodiments, the antisense oligonucleotide comprises the targeting sequence of SEQ ID NO:4 (M40). In specific embodiments, the antisense oligonucleotide consists of the targeting sequence of SEQ ID NO:4 (M40). In some embodiments, the cell is in a subject, and the method comprises administering the antisense oligonucleotides to the subject.

Certain embodiments include sensitizing the cell to a chemotherapeutic, where a predominant response of the cell to p53 expression, or p53 activation by the chemotherapeutic, is survival relative to cell-death, further comprising contacting the cell with the chemotherapeutic, prior to, at the same time as, or after contacting the cell with the antisense oligonucleotide(s), where the chemotherapeutic is a DNA intercalating agent, a topoisomerase II inhibitor, or both. In particular embodiments, the cell is a cancer cell. In certain embodiments, the cancer cell is associated with one or more of breast cancer, axillary lymph node involvement following resection of primary breast cancer, ovarian cancer, bladder cancer such as transitional cell bladder cancer, lung cancer, thyroid cancer, gastric cancer, soft tissue or osteogenic sarcoma, neuroblastoma, Wilms' tumor, malignant lymphoma (Hodgkin's or non-Hodgkin's), acute myeloid leukemia such as acute myeloblastic leukemia, acute lymphoblastic leukemia, Kaposi's sarcoma related to acquired immunodeficiency syndrome (AIDS), Ewing's tumor, squamous cell carcinoma of the head, neck, cervix, or vagina, carcinoma of the testes, prostate, or uterus, or refractory multiple myeloma. In some embodiments, the cancer cell is in a mammalian subject, and the method comprises administering the antisense oligonucleotide to the subject, prior to, before, or after administering the chemotherapeutic. In particular embodiments, the subject is a human subject.

Certain embodiments include methods for treating cancer, where the cancer is optionally refractory or resistant to a chemotherapeutic in a p53-associated manner. In some embodiments, the cancer is breast cancer, axillary lymph node involvement following resection of primary breast cancer, ovarian cancer, bladder cancer such as transitional cell bladder cancer, lung cancer, thyroid cancer, gastric cancer, soft tissue or osteogenic sarcoma, neuroblastoma, Wilms' tumor, malignant lymphoma (Hodgkin's or non-Hodgkin's), acute myeloid leukemia such as acute myeloblastic leukemia, acute lymphoblastic leukemia, Kaposi's sarcoma related to acquired immunodeficiency syndrome (AIDS), Ewing's tumor, squamous cell carcinoma of the head, neck, cervix, or vagina, carcinoma of the testes, prostate, or uterus, or refractory multiple myeloma.

In some embodiments, the chemotherapeutic is an anthracycline antibiotic or an analog thereof. In certain embodiments, the anthracycline antibiotic or analog thereof is one or more of daunorubicin (Daunomycin), doxorubicin (Adriamycin), epirubicin, idarubicin, valrubicin, or mitoxantrone, or a pharmaceutical salt or formulation thereof. In certain embodiments, the anthracycline antibiotic is doxorubicin or a pharmaceutical salt or formulation thereof. In some embodiments, the pharmaceutical salt is a hydrochloride salt. In particular embodiments, the formulation comprises a liposomal formulation. In specific embodiments, the formulation comprises a PEGylated form of doxorubicin, optionally comprising a liposomal formulation. In some embodiments, the doxorubicin is covalently attached to a monoclonal antibody.

In some embodiments, the antisense oligonucleotide is a phosphorodiamidate morpholino oligonucleotide (PMO), a PMO comprising one or more piperazine-containing intersubunit linkages (PMOplus), a PMO-X oligonucleotide, a peptide-nucleic acid (PNA), a locked-nucleic acid (LNA), or a 2'-O-methyl oligoribonucleotide. In particular embodiments, the antisense oligonucleotide is composed of morpholino subunits linked by phosphorus-containing intersubunit linkages joining a morpholino nitrogen of one subunit to a 5' exocyclic carbon of an adjacent subunit. In certain embodiments, the oligomer contains about 10%-50% intersubunit cationic linkages.

In certain embodiments, the antisense oligonucleotide is covalently attached to a cell-penetrating peptide. In certain embodiments, the cell-penetrating peptide is an arginine-rich peptide. In certain embodiments, the arginine-rich peptide is attached at its C-terminus to the 5' end of the oligonucleotide through a one- or two-amino acid linker. In certain embodiments, the peptide is attached at its C-terminus to the 3' end of the oligonucleotide through a one- or two-amino acid linker. In certain embodiments, the cell-penetrating peptide has a sequence selected from SEQ ID NOS:14-29.

Also included are compositions, comprising a first antisense oligonucleotide and a second antisense oligonucleotide, where the first antisense oligonucleotide is complementary to at least 12 bases of SEQ ID NO:1 (the region surrounding the AUG codon encoding for residue 1 of full-length p53), and where the second oligonucleotide is complementary to at least 12 bases of SEQ ID NO:2 (the region surrounding the AUG codon encoding for residue 40 of full-length p53). In certain embodiments, the first antisense oligonucleotide is complementary to the AUG start codon. In some embodiments, the first antisense oligonucleotides comprises a targeting sequence that is at least 90% identical to SEQ ID NO:3 (M1). In certain embodiments, the first antisense oligonucleotide comprises the targeting sequence of SEQ ID NO:3 (M1). In certain embodiments, the first antisense oligonucleotide consists of the targeting sequence of SEQ ID NO:3 (M1). In certain embodiments, the second antisense oligonucleotide is complementary to the AUG codon encoding for residue Met40 of full-length p53. In certain embodiments, the antisense oligonucleotides comprises a targeting sequence that is at least 90% identical to SEQ ID NO:4 (M40). In certain embodiments, the antisense oligonucleotide comprises the targeting sequence of SEQ ID NO:4 (M40). In certain embodiments, the antisense oligonucleotide consists of the targeting sequence of SEQ ID NO:4 (M40).

Certain compositions further comprise a chemotherapeutic, where the chemotherapeutic is a DNA intercalating agent, a topoisomerase II inhibitor, or both. In certain embodiments, the chemotherapeutic is an anthracycline antibiotic or an analog thereof. In certain embodiments, the anthracycline antibiotic or analog thereof is one or more of daunorubicin (Daunomycin), doxorubicin (Adriamycin), epirubicin, idarubicin, valrubicin, or mitoxantrone, or a pharmaceutical salt or formulation thereof. In certain embodiments, the antisense oligonucleotide is a phosphorodiamidate morpholino oligonucleotide (PMO), a PMO comprising one or more piperazine-containing intersubunit linkages (PMOplus), a peptide-nucleic acid (PNA), a locked-nucleic acid (LNA), or a 2'-O-methyl oligoribonucleotide. Also included are compositions for treating cancer, where the cancer is optionally refractory or resistant to a chemotherapeutic in a p53-associated manner.

Also included are methods for reducing expression of full-length p53 or an isoform or mutant thereof, comprising contacting a cell with an antisense oligonucleotide described herein, thereby reducing expression of full-length p53 or an isoform or mutant thereof. Some embodiments comprise contacting the cell with a first antisense oligonucleotide that is complementary to at least 12 bases of SEQ ID NO:1, and a second antisense oligonucleotide that is complementary to at least 12 bases of SEQ ID NO:2. In certain embodiments, a predominant response of the cell to p53 expression, or p53 activation by a chemotherapeutic or DNA damage, is survival relative to cell-death. In certain embodiments, the cell is in a subject, and the method comprises administering the antisense oligonucleotide(s) to the subject. Certain embodiments comprise sensitizing the cell to a chemotherapeutic, comprising contacting the cell with the chemotherapeutic prior to, at the same time as, or after contacting the cell with the antisense oligonucleotide(s). In certain embodiments, the cell is a cancer cell. Sometimes, where the cell is a cancer cell, the cancer cell is in a mammalian subject, and the method comprises administering the antisense oligonucleotide to the subject, prior to, before, or after administering the chemotherapeutic. In certain embodiments, the subject is a human subject.

Also included are methods for treating cancer, where the cancer is optionally refractory or resistant to a chemotherapeutic in a 53-associated manner. In some embodiments, the cancer is breast cancer, axillary lymph node involvement following resection of primary breast cancer, ovarian cancer, bladder cancer such as transitional cell bladder cancer, lung cancer, thyroid cancer, gastric cancer, soft tissue or osteogenic sarcoma, neuroblastoma, Wilms' tumor, malignant lymphoma (Hodgkin's or non-Hodgkin's), acute myeloid leukemia such as acute myeloblastic leukemia, acute lymphoblastic leukemia, Kaposi's sarcoma related to acquired immunodeficiency syndrome (AIDS), Ewing's tumor, squamous cell carcinoma of the head, neck, cervix, or vagina, carcinoma of the testes, prostate, or uterus, or refractory multiple myeloma. In certain embodiments, the chemotherapeutic is an anthracycline antibiotic or an analog thereof. In particular embodiments, the anthracycline antibiotic or analog thereof is one or more of daunorubicin (Daunomycin), doxorubicin (Adriamycin), epirubicin, idarubicin, valrubicin, or mitoxantrone, or a pharmaceutical salt or formulation thereof.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

FIG. 2A shows a western blot analysis of p53 and p21 expression in H460 cells treated with doxorubicin (200 ng/ml) for 24 hours. FIG. 2B shows a western blot analysis of p53 and p21 expression in HCT116 cells treated with 5-FU (50 µg/ml) for 24 hours. FIG. 2C shows a western blot analysis of p53 and p21 expression in OCI/AML3 and OCI/AML4 cells 5 hours after γ-irradiation (5 Gy). Cells were pre-treated with the indicated, peptide-conjugated PMOs (3 µM) for 2 hours prior to irradiation or drug treatment. p53 was detected with PAb1801.

FIG. 4A shows western blot analysis of p53 and p21 expression in H460 cells treated with doxorubicin (200 ng/ml) for 24 hours. Cells were pre-treated with increasing amounts of peptide-conjugated M40 for 2 hours prior to doxorubicin treatment. The arrowhead points to a 35 kDa polypeptide that is detected with DO1. FIG. 4B shows western blot analysis of p53 expression in H460 cells treated with doxorubicin (200 ng/ml) for 24 hours. Cells were pre-treated with peptide-conjugated PMOs, each at a concentration of 5 µM. The membranes were probed with 3 antibodies against p53 (PAb1801, DO1 and FL393) and with antibodies that recognize two p53 targets, p21 and Mdm2. β-actin expression serves as a protein loading control. Arrowheads point to a 35 kDa polypeptide recognized with DO1 and FL393 in cells treated with M40, and to a smaller polypeptide of about 33 kDa recognized by FL393 in cells treated with M1 and M40.

In FIG. 5A, HCT116 p53+/+ cells were treated with 5-FU (50 µg/ml) for 48 hours with or without prior treatment with E10, M1 or E10SA for 2 hours. After drug treatment, cells were collected, fixed, stained with propidium iodide and analyzed by flow cytometry. Apoptotic cells with sub-G1 DNA content are indicated. HCT116 p53−/− are included in the bottom panel as a control. In FIG. 5B, H460 cells were treated with doxorubicin (200 ng/ml) for 48 hours with or without prior treatment with CP-M1 (3 µM) or CP-E10SA (3 µM) for 2 hours. Cells were analyzed by flow cytometry after staining with propidium iodide.

In FIG. 6A, H460 cells were treated with doxorubicin (200 ng/ml) for 72 hours with or without prior treatment with peptide-conjugated MI (5 µM) and/or peptide conjugated M40 (5 µM) for 2 hours. After drug treatment, cells were collected, fixed, stained with propidium iodide and analyzed by flow cytometry. Apoptotic cells with sub-G1 DNA content are indicated. The histogram in FIG. 6B shows the proportion of cells with sub-G1 DNA content after treatment as in (A). The mean values from 3 independent experiments are shown +/− S.E.M. In FIG. 6C, H460 cells were treated with doxorubicin (200 ng/ml) for 72 hours with or without prior treatment with peptide-conjugated MI (5 µM) and/or peptide-conjugated M40 (5 µM) for 2 hours. After drug treatment, cells were collected and analyzed for caspase-3 activity using a flow cytometric assay. The histogram shows the proportion of cells with caspase-3 activity determined in 3 independent experiments. The mean values are shown +/− S.E.M.

DETAILED DESCRIPTION OF THE INVENTION

1. Definitions

Figure 1:
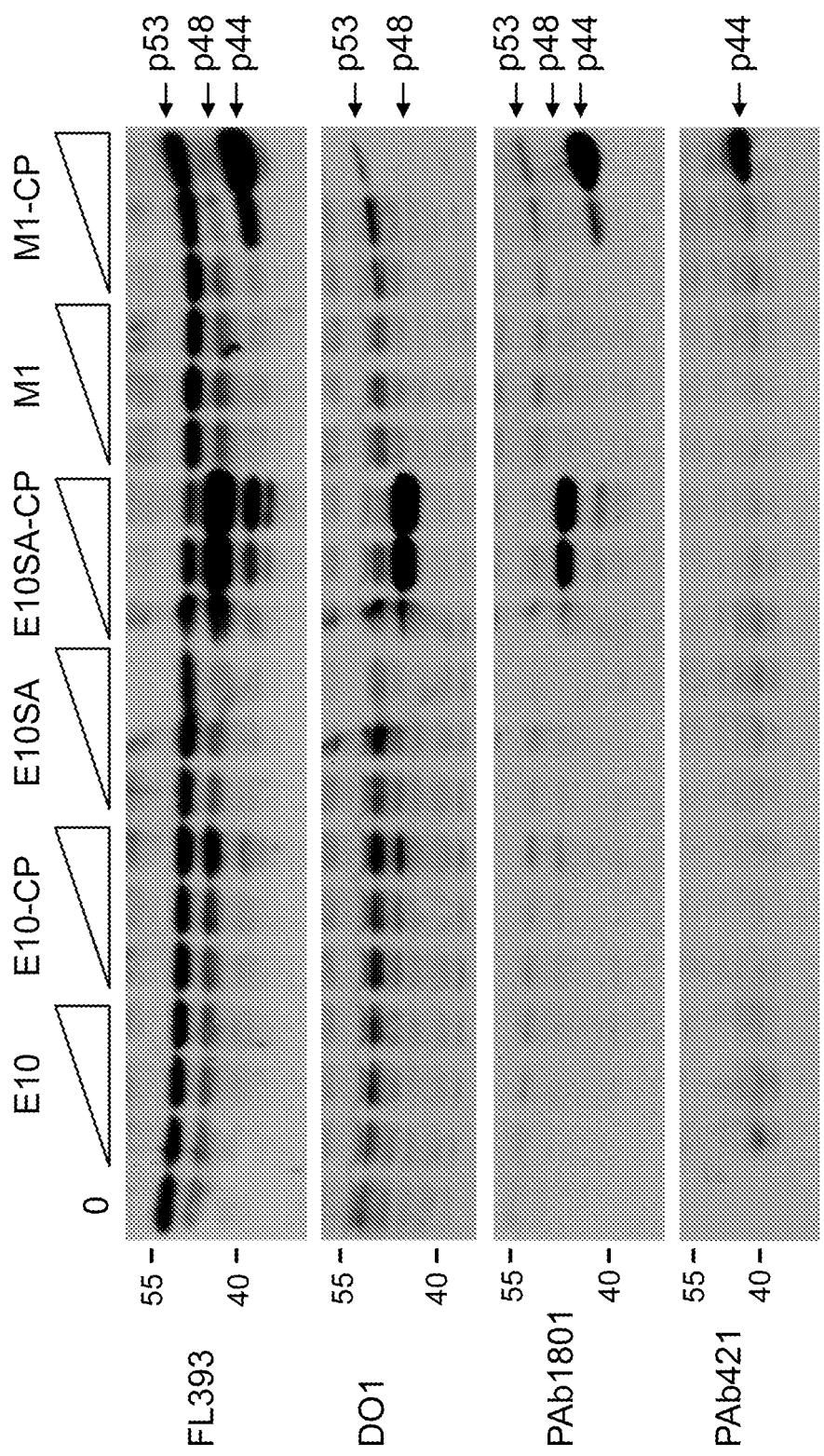
FIG. 1 shows that PMOs interfere with p53 expression in non-stressed MCF7 cells and increase translation of p53 isoforms. MCF7 cells were treated with increasing concentrations (0, 1, 3, 10 µM) of peptide-conjugated PMOs (E10-CP, E10SA-CP, M1-CP) or with non-conjugated PMOs (E10, E10SA, M1) for 2 hours. Cells were collected 24 hours after treatment and protein extracts were analyzed by Western blot analysis using 4 antibodies against p53.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

"Isoform" and "protein isoform" are used interchangeably to refer to proteins having different amino acid sequences, but are expressed from the same gene and optionally the same mRNA transcript. Non-limiting examples include transcription of different portions of the same gene at the level of DNA (e.g. transcription start sites), alternative splicing of mRNAs expressed from the same gene, and alternative translation products from the same mRNA or from different copies of the same mRNA (e.g. alternative codon usage and initiation of translation at different points along an mRNA, such as at different start codons). Isoforms may be naturally occurring or non-naturally occurring. In general, a naturally occurring isoform is an isoform that is translated by a cell in the absence of external intervention. In contrast, a non-naturally occurring isoform is generally an isoform that is translated at levels above a minimum threshold for detection only in the presence of an intervention in the natural translation process (e.g. delivery of an agent to a cell and in vitro translation methods).

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, or peptide transduction domains. The peptides, as shown herein, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration.

The terms "antisense oligomer" or "antisense compound" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), and 2'-O-Methyl oligonucleotides, and other antisense agents known in the art.

Such an antisense oligomer can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence is a region surrounding or including an AUG start codon of an mRNA, a 3' or 5' splice site of a pre-processed mRNA, or a branch point. The target sequence may be within an exon or within an intron. The target sequence for a splice site may include an mRNA sequence having its 5' end 1 to about 25 base pairs downstream of a normal splice acceptor junction in a preprocessed mRNA. A preferred target sequence for a splice is any region of a preprocessed mRNA that includes a splice site or is contained entirely within an exon coding sequence or spans a splice acceptor or donor site.

An oligomer is more generally said to be "targeted against" a biologically relevant target, such as a Tp53 gene mRNA (encoding a p53 protein), when it is targeted against the nucleic acid of the target in the manner described above. Exemplary targeting sequences include SEQ ID NOS:1 (region surrounding the p53 AUG start codon) and 2 (region surrounding the Met40 AUG codon of p53). Additional exemplary targeting sequences include SEQ ID NOs: 30-32.

In addition, included are illustrative antisense oligonucleotides that comprise, consist essentially of, or consist of one or more of SEQ ID NOS: 3-12. Also included are variants of these antisense oligomers, including variant oligomers having 80%, 85%, 90%, 95%, 97%, 98%, or 99% (including all integers in between) sequence identity or sequence homology to any one of SEQ ID NOS:3-12, and/or variants that differ from these sequences by about 1, 2, 3, 4, 5, 6, 7, 8, 9, or 10 nucleotides, preferably those variants that modulate (preferably reduce) p53 expression in a cell. Also included are oligonucleotides of any one or more of SEQ ID NOS:3-13, which comprise a suitable number of cationic or other modified linkages, as described herein, e.g., up to about 1 per every 2-5 uncharged linkages, such as about 4-5 per every 10 uncharged linkages, and/or which comprise an Arg-rich peptide attached thereto, as also described herein.

The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Appn. Nos. PCT/US07/11435 (cationic linkages) and U.S. Ser. No. 08/012,804 (improved synthesis), all of which are incorporated herein by reference.

"PMO+" refers to phosphorodiamidate morpholino oligomers comprising any number of (1-piperazino)phosphinylideneoxy, (1-(4-(ω-guanidino-alkanoyl))-piperazino) phosphinylideneoxy linkages (A2 and A3) that have been described previously (see e.g., PCT publication WO/2008/036127 which is incorporated herein by reference in its entirety.

"PMO-X" refers to phosphorodiamidate morpholino oligomers disclosed herein comprising at least one (B) linkage or at least one of the disclosed terminal modifications, and as disclosed in WO2011/150408 and US2012/0065169, which are incorporated herein by reference in their entireties. Further PMO-X phosphorodiamidate morpholino oligomers useful herein may be found in U.S. Provisional Application No. 61/561,806, filed Nov. 18, 2011, which is incorporated herein by reference in its entirety.

In addition, any oligonucleotide of the invention as described herein may comprise a boronic acid conjugate. A "boronic acid conjugate" of an oligonucleotide analogue refers to an oligonucleotide analogue comprising boronic acid or boronic ester moieties, as described in U.S. Provisional Application No. 61/613,385, filed Mar. 20, 2012, which is incorporated herein by reference in its entirety.

A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the modified intersubunit linkages of the oligomers described herein and U.S. Patent Application No. 61/349,783 and Ser. No. 11/801,885, one nitrogen is always pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits, for example structure (I).

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, typically at least 60% to 100% or 75% or 80% of its linkages, are uncharged, and contain a single phosphorous atom. Antisense oligonucleotides and oligonucleotide analogs may contain between about 8 and 40 subunits, typically about 8-25 subunits, and preferably about 12 to 25 subunits (including all integers and ranges in between). In certain embodiments, oligonucleotides may have exact sequence complementarity to the target sequence or near complementarity, as defined below.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U (see, e.g., Sequence Listing).

An "amino acid subunit" or "amino acid residue" can refer to an α-amino acid residue (—CO—CHR—NH—) or a β- or other amino acid residue (e.g., —CO—(CH$_2$)$_n$CHR—NH—), where R is a side chain (which may include hydrogen) and n is 1 to 7, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmosine, isodesmosine, homocysteine, citrulline and ornithine. The term "non-natural amino acids" refers to those amino acids not present in proteins found in nature, examples include beta-alanine (β-Ala), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that has been removed from the sequences that are normally adjacent to the fragment.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect (e.g., sensitization of a cancer cell to a chemotherapeutic) For an antisense oligomer, this effect is typically brought about by inhibiting translation or natural splice-processing of a selected target sequence. An "effective amount," targeted against p53 mRNA, also relates to an amount effective to modulate expression of p53.

By "enhance" or "enhancing," or "increase" or "increasing," or "stimulate" or "stimulating," refers generally to the ability of one or antisense compounds or compositions to produce or cause a greater physiological response (i.e., downstream effects) in a cell or a subject, as compared to the response caused by either no antisense compound or a control compound. Exemplary responses include increased sensitivity to a chemotherapeutic or other agent or treatment (e.g. DNA damage, radiation). An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7. 1.8, etc.) the amount produced by no antisense compound (the absence of an agent) or a control compound.

The term "reduce" or "inhibit" may relate generally to the ability of one or more antisense compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include, for example, reductions in expression of p53, or a mutant or truncant thereof, as measured by mRNA and/or protein levels. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "target sequence" refers to a portion of the target RNA against which the oligonucleotide or antisense agent is directed, that is, the sequence to which the oligonucleotide will hybridize by Watson-Crick base pairing of a complementary sequence. In certain embodiments, the target sequence may be a contiguous region of a pre-mRNA that includes both intron and exon target sequence. In certain other embodiments, the target sequence will consist exclusively of either intron or exon sequences.

The term "targeting sequence" or "antisense targeting sequence" refers to the sequence in an oligonucleotide or other antisense agent that is complementary (meaning, in addition, substantially complementary) to the target sequence in the RNA genome. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least 90% sequence homology, and preferably at least 95% sequence homology, with the exemplary antisense targeting sequences described herein.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Tip, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

An agent is "actively taken up by mammalian cells" when the agent can enter the cell by a mechanism other than passive diffusion across the cell membrane. The agent may be transported, for example, by "active transport," referring to transport of agents across a mammalian cell membrane by e.g., an ATP-dependent transport mechanism, or by "facilitated transport," referring to transport of antisense agents across the cell membrane by a transport mechanism that requires binding of the agent to a transport protein, which then facilitates passage of the bound agent across the membrane. For both active and facilitated transport, oligonucleotide analogs preferably have a substantially uncharged backbone, as defined below.

A "heteroduplex" refers to a duplex between an antisense oligonucleotide and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNaseH, which are capable of cutting double-stranded RNA/RNA or RNA/DNA complexes.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of a disease or pathology in the individual or cell. Treatment includes, but is not limited to, administration of, e.g., a pharmaceutical composition, and may be performed either prophylactically, or subsequent to the initiation of a pathologic event or contact with an etiologic agent. Treatment includes any desirable effect on the symptoms or pathology of a disease or condition associated with inflammation, among others described herein.

Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

A wild-type gene or gene product is that which is most frequently observed in a population and is thus arbitrarily designed the "normal" or "wild-type" form of the gene.

The chemical terms below have the following meanings, unless indicated otherwise:

"Amino" refers to the —NH$_2$ radical.
"Cyano" or "nitrile" refers to the —CN radical.
"Hydroxy" or "hydroxyl" refers to the —OH radical.
"Imino" refers to the =NH substituent.
"Guanidinyl" refers to the —NHC(=NH)NH$_2$ substituent.
"Amidinyl" refers to the —C(=NH)NH$_2$ substituent.
"Nitro" refers to the —NO$_2$ radical.
"Oxo" refers to the =O substituent.
"Thioxo" refers to the =S substituent.
"Cholate" refers to the following structure:

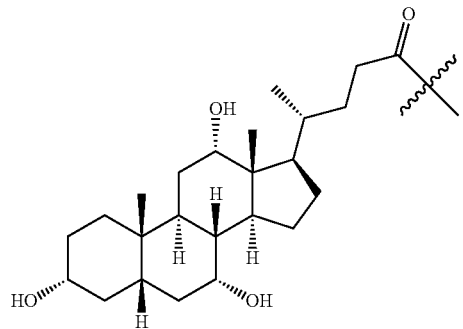

"Deoxycholate" refers to the following structure:

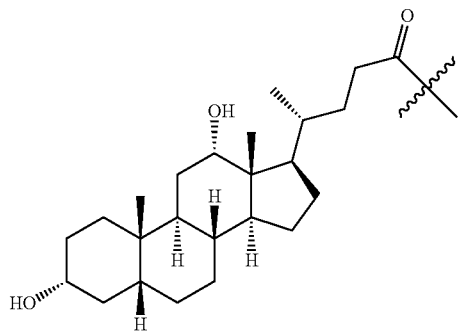

"Alkyl" refers to a straight or branched hydrocarbon chain radical which is saturated or unsaturated (i.e., contains one or more double and/or triple bonds), having from one to thirty carbon atoms, and which is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Alkoxyalkyl" refers to a radical of the formula —$R_bOR_a$ where $R_a$ is an alkyl radical as defined and where $R_b$ is an alkylene radical as defined. Unless stated otherwise specifically in the specification, an alkoxyalkyl group may be optionally substituted as described below.

"Alkylcarbonyl" refers to a radical of the formula —C(=O)$R_a$ where $R_a$ is an alkyl radical as defined above. Unless stated otherwise specifically in the specification, an alkylcarbonyl group may be optionally substituted as described below.

"Alkyloxycarbonyl" refers to a radical of the formula —C(=O)O$R_a$ where $R_a$ is an alkyl radical as defined. Unless stated otherwise specifically in the specification, an alkyloxycarbonyl group may be optionally substituted as described below.

"Alkylamino" refers to a radical of the formula —NH$R_a$ or —N$R_a R_a$ where each $R_a$ is, independently, an alkyl radical as defined above. Unless stated otherwise specifically in the specification, an alkylamino group may be optionally substituted as described below.

"Amidyl" refers to a radical of the formula —N(H)C(=O)$R_a$ where $R_a$ is an alkyl or aryl radical as defined herein. Unless stated otherwise specifically in the specification, an amidyl group may be optionally substituted as described below.

"Amidinylalkyl" refers a radical of the formula —$R_b$—C(=NH)NH$_2$ where $R_b$ is an alkylene radical as defined above. Unless stated otherwise specifically in the specification, an amidinylalkyl group may be optionally substituted as described below.

"Amidinylalkylcarbonyl" refers a radical of the formula —C(=O)$R_b$—C(=NH)NH$_2$ where $R_b$ is an alkylene radical as defined above. Unless stated otherwise specifically in the specification, an amidinylalkylcarbonyl group may be optionally substituted as described below.

"Aminoalkyl" refers to a radical of the formula —$R_b$—N$R_a R_a$ where $R_b$ is an alkylene radical as defined above, and each $R_a$ is independently a hydrogen or an alkyl radical.

"Thioalkyl" refers to a radical of the formula —S$R_a$ where $R_a$ is an alkyl radical as defined above. Unless stated otherwise specifically in the specification, a thioalkyl group may be optionally substituted.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Arylcarbonyl" refers to a radical of the formula —C(=O)$R_c$ where $R_c$ is one or more aryl radicals as defined above, for example, phenyl. Unless stated otherwise specifically in the specification, an arylcarbonyl group may be optionally substituted.

"Aryloxycarbonyl" refers to a radical of the formula —C(=O)O$R_c$ where $R_c$ is one or more aryl radicals as defined above, for example, phenyl. Unless stated otherwise specifically in the specification, an aryloxycarbonyl group may be optionally substituted.

"Aralkylcarbonyl" refers to a radical of the formula —C(=O)$R_b$—$R_c$ where $R_b$ is an alkylene chain as defined above and $R_c$ is one or more aryl radicals as defined above, for example, phenyl. Unless stated otherwise specifically in the specification, an aralkylcarbonyl group may be optionally substituted.

"Aralkyloxycarbonyl" refers to a radical of the formula —C(=O)O$R_b$—$R_c$ where $R_b$ is an alkylene chain as defined above and $R_c$ is one or more aryl radicals as defined above, for example, phenyl. Unless stated otherwise specifically in the specification, an aralkyloxycarbonyl group may be optionally substituted.

"Aryloxy" refers to a radical of the formula —O$R_c$, where $R_c$ is one or more aryl radicals as defined above, for example, phenyl. Unless stated otherwise specifically in the specification, an arylcarbonyl group may be optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms and from three to eight carbon atoms, Monocyclic cycicoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted.

"Cycloalkylalkyl" refers to a radical of the formula —$R_b R_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkylcarbonyl" refers to a radical of the formula —C(=O)$R_d$ where $R_d$ is a cycloalkyl radical as defined above. Unless stated otherwise specifically in the specification, a cycloalkylcarbonyl group may be optionally substituted.

Cycloalkyloxycarbonyl" refers to a radical of the formula —C(=O)O$R_d$ where $R_d$ is a cycloalkyl radical as defined above. Unless stated otherwise specifically in the specification, a cycloalkyloxycarbonyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Guanidinylalkyl" refers a radical of the formula —$R_b$—NHC(=NH)$NH_2$ where $R_b$ is an alkylene radical as defined above. Unless stated otherwise specifically in the specification, a guanidinylalkyl group may be optionally substituted as described below.

"Guanidinylalkylcarbonyl" refers a radical of the formula —C(=O)$R_b$—NHC(=NH)$NH_2$ where $R_b$ is an alkylene radical as defined above. Unless stated otherwise specifically in the specification, a guanidinylalkylcarbonyl group may be optionally substituted as described below.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5,18-crown-6,21-crown-7, aza-18-crown-6, diaza-18-crown-6, aza-21-crown-7, and diaza-21-crown-7. Unless stated otherwise specifically in the specification, a heterocyclyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —$CO_2H$, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$CH_2SO_2R_g$, —$CH_2SO_2NR_gR_h$, —SH, —$SR_g$ or —$SSR_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc. Amidyl moieties may be substituted with up to 2 halo atoms, while other groups above may be substituted with one or more halo atoms. With the exception of alkyl groups, all other groups may also be substituted with amino or monoalklyamino. With the exception of alkyl and alkylcarbonyl groups, all other groups may also be substituted with guanidinyl or amidynyl. Optional substitutents for any of the above groups also include arylphosphoryl, for example —$R_aP(Ar)_3$ wherein Ra is an alkylene and Ar is aryl moiety, for example phenyl.

"Lower alkyl" refers to an alkyl radical of one to six carbon atoms, as exemplified by methyl, ethyl, n-butyl, i-butyl, t-butyl, isoamyl, n-pentyl, and isopentyl. In certain embodiments, a "lower alkyl" group has one to four carbon atoms. In other embodiments a "lower alkyl" group has one to two carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and/or relatively non-polar groups such as methyl, ethyl, methoxy, ethoxy, or fluoro.

2. Targeting Alternative Translation Start Codons

In some embodiments, an antisense oligonucleotide provided herein is substantially complementary to a translation start codon of an mRNA that encodes at least two cellular protein isoforms, each isoform translated from a different start codon. The term "start codon" refers to the codon encoding the first amino acid of a protein isoform translated from an mRNA. Typically, the start codon is AUG (all sequences listed in 5' to 3' orientation unless otherwise indicated), encoding methionine or formylmethionine. However, alternative codons used as the point of translation initiation and encoding the first amino acid of a protein translated from an mRNA are also encompassed by the term. Non-limiting examples of alternative start codons include CUG, GUG, UUG, AUA, UUU, and ACG. A single mRNA may comprise one or more start codons, such as about or more than about 2, 3, 4, 5, 6, 7, 8, 9, 10, 11, 12, 13, 14, 15, 20, or more start codons, each of which may be any of a number of possible start codons. Proteins translated from different start codons are referred to as "isoforms" of one another. Each of two or more start codons may be used equally within a cell for the translation initiation of the corresponding isoforms. Typically, one codon serves as the primary start codon, and is preferentially used within a cell for the translation initiation of the corresponding primary isoform of the protein. One or more start codons to which an antisense oligonucleotide provided herein is substantially complementary is referred to as a "target start codon." Start codons in addition to the target start codon are referred to as "alternative start codons." Alternative start codons may or may not be utilized within a cell for the translation initiation of the corresponding isoforms.

In certain embodiments, hybridization of the antisense oligonucleotide provided herein to a target start codon inhibits translation of the isoform expressed from the target start codon. In some embodiments, the level of inhibition is about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more. In some embodiments, the level of inhibition is about, less than about, or more than about 2-fold, 5-fold, 10-fold, 100-fold, 1000-fold, 10000-fold, 100000-fold, 1000000-fold, or more. In some embodiments, the level of translation initiation activity of one or more alternative start codons increases in the presence of an antisense oligonucleotide that hybridizes to a target start codon, such as an increase of about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more. In some embodiments, one or more alternative start codons are only utilized for translation initiation (e.g. detectable above a minimum threshold of detection) when one or more target start codons (e.g. the primary start codon) are blocked by hybridization to an antisense oligonucleotide provided herein. In some embodiments, the level of translation initiation activity of one or more alternative start codons is unaffected by hybridization of the antisense oligonucleotide with a target start codon. In some embodiments, the portion of the antisense oligonucleotide that is substantially complementary the start codon is located near the middle of the antisense oligonucleotide sequence, or the middle of the portion of the antisense oligonucleotide sequence that specifically hybridizes to a target polynucleotide (e.g. an mRNA).

An alternative start codon may be located 5' or 3' with respect to a target start codon. In general, an isoform initiated from an alternative start codon located 5' with respect to a target start codon comprises an N-terminal extension with respect to the isoform initiated from the target start codon, while an isoform initiated from an alternative start codon located 3' with respect to a target start codon comprises an N-terminal deletion with respect to the isoform initiated from the target start codon. Amino acid sequences encoded by regions of extension or deletion between isoforms may comprise functional regions or domains associated with one or more cellular activities or protein characteristics, including, but not limited to, protein-protein interactions (e.g. binding domains), protein localization signals (e.g. signal peptide), sequences involved in membrane association (e.g. runs of hydrophobic amino acids), sequences associated with proper protein folding, sequences associated with proper post-translational processing, and sequences associated with enzymatic activity (e.g. the active site of an enzyme, or a target site for the regulation of an enzyme, such as a phosphorylation site). As a result, isoforms of a single protein may have different cellular localizations and/or activities. For example, one isoform may be secreted while another isoform is not secreted (e.g. cytosolic). As a further example, one isoform may have a signaling or enzymatic activity that is regulated while the signaling or enzymatic activity of another isoform is unregulated. In some embodiments, the activity of a protein isoform translated from a target start codon is completely missing from (e.g. below a minimum threshold for detection) an isoform translated from an alternative start codon. In general, the biological significance of alternate translation start sites is determined by the differences in the peptide segment that is not shared by the two or more related proteins. In the case of fibroblast growth factor 2 (FGF2), an 18 kDa protein synthesized from one AUG start site is a cytoplasmic protein that is a ligand for cell surface receptors while a 24 kDa protein synthesized from an upstream CUG start site contains a nuclear localization signal and can induce cell immortalization and enhanced metastatic properties in rat bladder carcinoma. In the case of vascular endothelial growth factor (VEGF), the larger protein synthesized from an upstream CUG start site is an intracellular protein localized to the Golgi apparatus while the smaller protein synthesized from the AUG start site is a secreted protein. In each case the proteins resulting from alternate translation start sites possess different cellular localization and function capable of changing the fate of the cell.

An alternative start codon can be located in-frame or out-of-frame with respect to a target codon, and can be located about, less than about, or more than about 10, 15, 20, 25, 30, 35, 40, 45, 50, 55, 60, 65, 70, 75, 80, 85, 90, 100, 120, 150, 180, 210, or more nucleotides away from a target start codon. In some embodiments, protein isoforms expressed from alternative start codons comprise N-terminal extensions or deletions of about, less than about, or more than about 10, 15, 20, 25, 30, 35, 40, 45, 50, 55, 60, 65, 70, 75, 80, 85, 90, 95, 100, 150, 200, or more amino acids.

Proteins encoded by mRNA targets provided herein include any protein having two or more isoforms encoded by the target mRNA. In some embodiments, translation may only initiate at one of two or more start codons of the two or more isoforms to produce detectable levels of only a single isoform in the absence of an antisense oligonucleotide provided herein, the presence of which induces translation from an alternative start codon to produce detectable levels of one or more additional isoforms. Examples of proteins encoded by mRNA targets provided herein include, but are not limited to, cellular proteins, eukaryotic proteins, prokaryotic proteins, plant proteins, animal proteins, mammalian proteins, human proteins, and signaling proteins. In some embodiments, the protein encoded by a target mRNA is not a viral protein, such as a foot-and-mouth-disease viral protein. In some embodiments, the protein encoded by a target mRNA is a protein involved in cell cycle regulation. In some embodiments, the isoform inhibited by the antisense oligonucleotide is an aberrant or dysfunctional protein isoform. In some embodiments, the isoform inhibited by the antisense oligonucleotide is associated with a disease, including but not limited to a proliferative disorder, a neurodegenerative disorder, an inflammatory disorder, or an autoimmune disorder.

Illustrative proteins having alternative translation initiation sites and useful in the context of the present invention may be found in various known and publicly available databases. In one example, sequences may be identified from the "Human alternative open reading frames (HAltORF) database, which is a publicly available and searchable online database referencing putative products of out-of-frame alternative translation initiation (ATI) in human mRNAs (Database (Oxford). 2012 May 20; 2012:bas025. Print 2012)(www.ncbi.nlm.nih.gov/pubmed/22613085).

In another example, sequences may be identified from the ATID database (bioinfo.au.tsinghua.edu.cn/atie/browse.php?organism=Homo%20sapiens), as described by Cai et al. (ATID: a web-oriented database for collection of publicly available alternative translational initiation events. Bioinformatics, doi:10.1093/bioinformatics/bti704) and Zhang et al. (A genome-wide survey of alternative translational initiation events in human. Science in China Series C: Life Sciences. 2007 50 (3): 423-428).

Illustrative examples of proteins useful in accordance with the present invention include, but are in no way limited to, p53, SMN, TBP, FGF2, VEGF-A, c-Myc, n-Myc, 1-Myc, LYL1, p15 INK4B, WT1, BAG1, NOD2, Caspase 8, Catechol O methyl transferase, EGF3, EIF4G1, GATA1, TRIIA-alpha, IL-1ra, MAP3K8, NFATC1, SHC, SOCS3, RAG1, IDE, TDP-43, and RGS2.

Additional information about exemplary genes that may be targeted according to the invention can be readily located from publicly available sources (e.g., NCBI, Human Genome Compendium, and elsewhere). Information about p53, for example, can be found at genecards.org/cgi-bin/carddisp.pl?gene=Tp53&search=p53. Information about FGF2, for example, can be found at genecards.org/cgi-bin/carddisp.pl?gene=FGF2&search=FGF2. Information about VEGF-A, for example, can be found at genecards.org/cgi-bin/carddisp.pl?gene=VEGFA&search=VEGF-A. Information about c-Myc, for example, can be found at genecards.org/cgi-bin/carddisp.pl?gene=MYC&search=c-Myc. Information about n-Myc, for example, can be found at genecards.org/cgi-bin/carddisp.pl?gene=MYCN&search=n-Myc. Information about LYL1, for example, can be found at genecards.org/cgi-bin/carddisp.pl?gene=LYL1&search=LYL1. Information about p15 INK 4B, for example, can be found at genecards.org/cgi-bin/carddisp.pl?gene=CDKN2B&search=INK4B. Information about WT1, for example, can be found at genecards.org/cgi-bin/carddisp.pl?gene=WT1&search=WT1. Information about BAG1, for example, can be found at genecards.org/cgi-bin/carddisp.pl?gene=BAG1&search=BAG1. Information about NOD2, for example, can be found at genecards.org/cgi-bin/carddisp.pl?gene=NOD2&search=NOD2. Information about Caspase 8, for example, can be found at genecards.org/cgi-bin/carddisp.pl?gene=CASP8&search=caspase+8. Information about COMT, for example, can be found at genecards.org/cgi-in/carddisp.pl?gene=COMT&search=Catechol+O+methyl+transferase+. Information about EIF4G1 can be found, for example, at genecards.org/cgi-bin/carddisp.pl?gene=EIF4G1&search=EIF4G1. Information about GATA1 can be found, for example, at genecards.org/cgi-bin/carddisp.pl?gene=GATA1& search=GATA1. Information about IL-1ra can be found, for example, at genecards.org/cgi-bin/carddisp.pl?gene=IL1RN&search=Interleukin+1+receptor+%28IL-1ra%29. Information about MAP3K8 can be found, for example, at genecards.org/cgi-bin/carddisp.pl?gene=MAP3K8&search=MAP3K8. Information about NFATC1 can be found, for example, at genecards.org/cgi-bin/carddisp.pl?gene=NFATC1&search=NFATC1. Information about SHC can be found, for example, at genecards.org/cgi-bin/carddisp.pl?gene=SHC1&search=SHC. Information about SOCS3 can be found, for example, at genecards.org/cgi-bin/carddisp.pl?gene=SOCS3&search=SOCS3. Information about RAG1 can be found, for example, at genecards.org/cgi-bin/carddisp.pl?gene=RAG1&search=RAG1. Information about IDE, for example, can be found at genecards.org/cgi-bin/carddisp.pl?gene=IDE&search=IDE. Information about TDP-43, for example, can be found at genecards.org/cgi-bin/carddisp.pl?gene=TARDBP&search=TDP-43. Information about RGS2, for example, can be found at genecards.org/cgi-bin/carddisp.pl?gene=RGS2&search=RGS2.

Table 1 provides a list of additional information relating to illustrative genes having known alternative translation start codons, at least one of which is not the typical sequence of AUG, as well as the associated NCBI database accession numbers and sample start codons. Table 2 provides additional information relating to illustrative genes having two or more known isoforms, as well as the length, pI, and molecular weight of each isoform.

TABLE 1

ILLUSTRATIVE GENES HAVING ALTERNATIVE TRANSLATION START CODONS

| Gene | Accession Number | Codon |
|---|---|---|
| FGF2 | NM 002006 | 4 CUG, 1 AUG |
| VEGF-A | NM 003376 | 1 CUG, 1 AUG |
| c-myc | NM 002467 | 1 CUG, 1 AUG |
| N-myc | NM 005378 | 1 CUG, 1 AUG |
| L-myc | NM 005376 | 1 CUG, 1 AUG |
| LYL1 | NM 005583 | 1 CUG, 1 AUG |
| p15 INK 4B | NM 004936 | 1 CUG, 1 AUG |
| WT1 | NM 000378 | 1 CUG, 1 AUG |
| BAG1 | NM 004223 | 1 CUG, 1 AUG |

TABLE 2

ILLUSTRATIVE GENES HAVING TWO OR MORE KNOWN ISOFORMS

| Gene | Accession No. | Isoform | Length | PI | Mol Weight |
|---|---|---|---|---|---|
| NOD2 | NM_022162 | Isoform 1 | 1040 | 6.3 | 115283 |
| | | Isoform 2 | 1013 | 6.6 | 112530 |

TABLE 2-continued

ILLUSTRATIVE GENES HAVING TWO OR MORE KNOWN ISOFORMS

| Gene | Accession No. | Isoform | Length | PI | Mol Weight |
|---|---|---|---|---|---|
| Caspase 8 | NM_001228 | Isoform 1 | 538 | 5.2 | 61864 |
| | | Isoform 2 | 479 | 5.0 | 55391 |
| Catechol O methyl transferase (COMT) | NM_000754 | Isoform 1 | 271 | 5.3 | 30037 |
| | | Isoform 2 | 221 | 5.2 | 24449 |
| Epidermal Growth Factor Receptor 3 (EGF3) | | Isoform 1 | 387 | 8.6 | 42613 |
| | | Isoform 2 | 282 | 9.3 | 31160 |
| Early Initiation Factor 4G1 (EIF4G1) | NM_182917 | Isoform 1 | 1600 | 5.3 | 175535 |
| | | Isoform 2 | 1513 | 5.2 | 16663 |
| | | Isoform 3 | 1436 | 5.1 | 158597 |
| | | Isoform 4 | 1404 | 4.1 | 154885 |
| GATA1 | NM_002049 | Isoform 1 | 413 | 9.0 | 42751 |
| | | Isoform 2 | 330 | 9.5 | 34232 |
| Transcription Factor 2A-α (TRIIA-alpha) | | Isoform 1 | 376 | 4.4 | 41514 |
| | | Isoform 2 | 337 | 4.5 | 37152 |
| Interleukin 1 receptor (IL-1ra) | NM_173841 | Isoform 1 | 177 | 5.8 | 20055 |
| | | Isoform 2 | 143 | 4.8 | 16142 |
| MAP3K8 | NM_005204 | Isoform 1 | 467 | 5.5 | 52898 |
| | | Isoform 2 | 438 | 5.9 | 49593 |
| NFATC1 | NM_172390 | Isoform 1 | 716 | 7.9 | 77785 |
| | | Isoform 2 | 680 | 7.4 | 74276 |
| SHC | NM_183001 | Isoform 1 | 583 | 5.9 | 62852 |
| | | Isoform 2 | 473 | 6.7 | 51611 |
| | | Isoform 3 | 428 | 6.1 | 46668 |
| SOCS3 | NM_003955 | Isoform 1 | 225 | 9.0 | 24770 |
| | | Isoform 2 | 214 | 8.8 | 23643 |
| RAG1 | NM_000448 | Isoform 1 | 345 | 8.3 | 38878 |
| | | Isoform 2 | 274 | 5.1 | 31117 |
| | | Isoform 3 | 230 | 5.2 | 25989 |

It will be understood in light of the present disclosure and the list of exemplary genes how to make and use antisense oligonucleotides of the present invention which target a gene of interest.

A. Illustrative Embodiments for Targeting Alternative Translation Start Codons of the p53 Protein The p53 tumor suppressor protein is encoded by Tp53 gene. The human gene is located on the short arm of chromosome 17 (17p13.1), a region that is frequently deleted in human cancers. The human Tp53 gene spans about 22,000 base pairs, contains 11 exons, and codes for a ~2.2 Kb mRNA. Translation of the wild-type or full-length p53 protein (also referred to as isoform 1; p53α; or "p53") begins in exon 2.

Human p53 is 393 amino acids in length, and can be divided into at least seven domains, each corresponding to specific functions. (I) An acidic N-terminus transactivation domain (TAD), also known as activation domain 1 (AD1; TA1) (~1-42). The N-terminus contains two complementary transcriptional activation domains, a major one at about residues 1-42 and a minor one at about residues 55-75, specifically involved in the regulation of several pro-apoptotic genes. This region also contains the Highly Conserved Domain I (HCD I). (II) An activation domain 2 (AD2; TA2), the second and minor TAD referred to above, which is important for apoptotic activity (~43-63). (III) A proline rich domain important for the apoptotic activity of p53 (~64-92). (IV) A central DNA-binding core domain (DBD), which contains one zinc atom and several arginine amino acids (~100-300). This region is responsible for binding the p53 co-repressor LMO3, contains HCD II to V, and is the target of about 90% of p53 mutations found in human cancers. (V) A nuclear localization signaling domain (~316-325). (VI) A homo-oligomerisation domain (OD) (~307-355), which contains a beta-strand followed by an alpha-helix that is necessary for dimerization. Human p53 is composed of a dimer of two dimers (a tetramer); tetramerization appears to be essential for many activities of p53 in vivo. (VII) A C-terminal involved in downregulation of DNA binding of the central domain (~356-393). This region can also bind non-specifically to damaged DNA.

Alternative splicing of p53 pre-mRNA leads to numerous P53 isoforms. As noted above, the wild-type or "canonical" p53 isoform is sometimes referred to as P53α. Exemplary "non-canonical" isoforms include p53β, which differs from the wild-type sequence as follows: residues 332-341 are altered from IRGRERFEMF (SEQ ID NO: 33)→DQTSFQKENC (SEQ ID NO: 34), and residues 342-393 are deleted. p53γ differs from the wild-type sequence as follows: residues 332-341 are altered from IRGRERFEMF (SEQ ID NO: 33)→DQTSFQKENC (SEQ ID NO: 34), and residues 342-393 are deleted. Δ40p53 is an N-terminal truncant that is missing residues 1-39. Δ40p53β is missing residues 1-39, has an alteration from IRGRERFEMF (SEQ ID NO: 33)→DQTSFQKENC (SEQ ID NO: 34) at residues 332-341, and is missing residues 342-393. Δ40p53γ is missing residues 1-39, has an alteration from IRGRERFEMFRELNE (SEQ ID NO: 35)→MLLDLRWCYFLINSS (SEQ ID NO: 36) at residues 332-346, and is missing residues 347-393. Δ133p53 is missing residues 1-132. Δ133p53β is missing residues 1-132, has an alteration from IRGRERFEMF (SEQ ID NO: 33)→DQTSFQKENC (SEQ ID NO: 34) at residues 332-341, and is missing residues 342-393. Δ133p53γ is missing residues 1-132, has an alteration of IRGRERFEMFRELNE (SEQ ID NO: 35)→MLLDLRWCYFLINSS (SEQ ID NO: 36) at residues 332-346, and is missing residues 347-393. Δp53 is missing about 66 residues including Highly Conserved Domain V. Certain p53 isoforms described herein are referred to more generally as ΔN-p53 (or p44), which is missing TA1 but retains TA2, and is likely produced by internal initiation of translation at codon 40 in human p53 mRNA. p48 likely corresponds to either p53β or p53γ, and is for certain experiments is referred to as p53β/γ. The ΔN-p53β/γ isoform is likely missing the N-terminal transactivation domain as well as the C-terminal oligomerization domain of p53.

Antisense agents or combinations thereof can be targeted to reduce expression of any one or more of the p53 isoforms described herein and/or known in the art. Antisense agents can also be targeted to reduce induction of any one or more of the non-canonical p53 isoforms, for instance, by minimizing the oligonucleotide's effects on alternate splicing that might otherwise lead to expression of such p53 isoforms. One advantage of minimizing expression of non-canonical p53 isoforms can be found in reducing their potential for unanticipated activities. Even though many isoforms are believed to be inactive, for instance, because they lack transcriptional activity at known p53-regulated promoters or lack the ability to oligomerize, it is still possible that they possess unanticipated and potentially undesirable activities. Certain embodiments therefore relate to combinations of antisense agents that have shown to be capable of not only reducing expression of wild-type or mutant p53, but also reducing expression (or minimizing induction) of non-canonical p53 isoforms, such as ΔN-p53, p53β and/or p53γ isoforms, among others described herein and known in the art. Examples include combinations of antisense oligonucleotides that target SEQ ID NO:1 and 2, discussed below.

Certain antisense oligonucleotides may comprise a targeting sequence that is complementary to one or more bases of the AUG start codon of wild-type p53 and/or the region surrounding that start codon, as shown in SEQ ID NO:1. Some antisense oligonucleotides may comprise a targeting sequence that is complementary to one or more bases of the methionine AUG codon at position 40 of wild-type p53 (Met40) and/or the region surrounding that codon, as shown in SEQ ID NO:2. These target sequences are shown in Table 3 below:

TABLE 3

EXEMPLARY P53 TARGET SEQUENCES

| NAME | SEQUENCE | SEQ ID NO: |
|---|---|---|
| Region Surrounding AUG Start Codon | CUGCCUUCCGGGUCACUGCCAUGGAGGAGCCGC AGUCAGAUCCUAGCGUCGAG | 1 |
| Region Surrounding Met40 AUG Codon | CCCCCUUGCCGUCCCAAGCAAUGGAUGAUUUGA UGCUGUCCCGGACGAUAUU | 2 |

Examples include antisense oligonucleotides that are fully complementary to the highlighted (bold) AUG codon in SEQ ID NO:1 or 2, including those that are also complementary to 1, 2, 3, 4, 5, 6, 7, 8, 9, or 10 bases on the 5' side, 3' side, or both sides of that codon. Certain antisense oligonucleotides may comprise a targeting sequence where the 5'-most base is complementary to a base that is 10, 11, 12, 13, 14, 15, 16, 17, 18, 19, 20, 21, 22, 23, 24, 25, 26, 27, 28, 29, or 30 bases downstream of the highlighted AUG codon in SEQ ID NO:1 or 2 (see Table 1), and which is complementary to a defined number of bases (e.g., 10-40 bases) upstream of that base. Certain antisense oligonucleotides may comprise a targeting sequence where the 3'-most base is complementary to a base that is 10, 11, 12, 13, 14, 15, 16, 17, 18, 19, or 20 bases upstream of the highlighted AUG codon in SEQ ID NO:1 or 2 (see Table 1), and which is complementary to a defined number of bases (e.g., 10-40 bases) downstream of that base. Certain embodiments relate to the use of a combination of these antisense agents, one that targets SEQ ID NO:1, and another that targets SEQ ID NO:2. Specific embodiments include antisense oligonucleotides comprising all or a portion (e.g., 10, 11, 12, 13, 14, 15, 16, 17, 18 bases) of SEQ ID NO:3 (M1) or 4 (M40).

Antisense oligonucleotides can also be targeted against, or be complementary to, a variety of region(s) in a pre-processed mRNA, such as an exon, an intron, an exon-intron junction, or a splice junction. For instance, certain antisense oligonucleotides may comprise a targeting sequence that is complementary to a region (target sequence) that overlaps the splice junction of a splice donor (SD) or splice acceptor (SA) site of exon 1, 2, 3, 4, 5, 6, 7, 8, 9, 10, or 11 of p53 pre-mRNA, and is complementary to a portion of an exonic region (e.g., 8, 9, 10, 11, 12, 13, 14, 15, 16, 17, 18, 19, 20, 21, 22, 23, 24, 25, 26, 27, 28, 29, or 30 nucleotides) and a portion of an intronic region (e.g., 8, 9, 10, 11, 12, 13, 14, 15, nucleotides) of the pre-processed mRNA.

Certain exemplary antisense oligonucleotides may comprise a targeting sequence that is complementary to an exonic region (target sequence) defined by the first 10, 15, 20, 25, 30, 40, 50, 60, 70, 80, 90, or 100 nucleotides (or ranges such as the first 10-30, 20-40, 30-50, 40-60, 50-70, 60-80, 80-100 nucleotides) immediately downstream of the splice acceptor site of exon 1, 2, 3, 4, 5, 6, 7, 8, 9, 10, or 11 of p54 pre-mRNA, but either does not overlap with the splice junction, or overlaps with the splice junction and is complementary to about 1, 2, 3, 4, 5, 6, 7, 8, 9, or 10 nucleotides of the proximal (upstream) intron. Some exemplary antisense oligonucleotides may comprise a targeting sequence that is complementary to an exonic region (target sequence) defined by the first 10, 15, 20, 25, 30, 40, 50, 60, 70, 80, 90, or 100 nucleotides (or ranges such as the first 10-30, 20-40, 30-50, 40-60, 50-70, 60-80, 80-100 nucleotides) immediately upstream of the splice donor site of exon 1, 2, 3, 4, 5, 6, 7, 8, 9, 10, or 11 of p54 pre-mRNA, but either does not overlap with the splice junction, or overlaps with the splice junction and, but either does not overlap with the splice junction, or overlaps with the splice junction and is complementary to about 1, 2, 3, 4, 5, 6, 7, 8, 9, or 10 nucleotides of the proximal (downstream) intron. Certain antisense oligonucleotides are complementary to at least about 8, 9, 10, 11, 12, 13, 14, 15, 16, 17, 18, 19, 20, 21, 22, 23, 24, 25, 26, 27, 28, 29, 30 or more contiguous or non-contiguous nucleotides within these target sequences. Exemplary splice-site or exon-targeted antisense oligonucleotides include those that comprise all or a portion (e.g., 10, 11, 12, 13, 14, 15, 16, 17, 18 bases) of SEQ ID NOS:5-12.

Selected antisense targeting sequences can be made shorter, e.g., about 12 bases, or longer, e.g., about 40 bases, and include a small number of mismatches, as long as the sequence is sufficiently complementary to effect translation, splicing, and/or other form of inhibition upon hybridization with the target, and forms with the target RNA, a heteroduplex having a Tm of 45° C. or greater.

In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, 12-25, or 15-25 bases, including all integers and ranges in between these ranges. An antisense oligomer of about 14-15 bases is generally long enough to have a unique complementary sequence in the target mRNA. In certain embodiments, a minimum length of complementary bases may be required to achieve the requisite binding Tm, as discussed below.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths less than about 30. For PMO oligomers, described further below, an optimum balance of binding stability and uptake generally occurs at lengths of 18-25 bases. Included are antisense oligomers (e.g., PNAs, LNAs, 2'-OMe, MOE, PMOs) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous and/or non-contiguous bases are complementary to a target sequence described herein, including the target sequences of SEQ ID NO:1 and 2, or variants thereof.

In certain embodiments, antisense oligomers may be 100% complementary to the p53 nucleic acid target sequence, or they may include mismatches, e.g., to accommodate variants, as long as a heteroduplex formed between the oligomer and the target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that a biological activity of the nucleic acid target, e.g., expression of p53 protein(s), is modulated.

The stability of the duplex formed between an oligomer and a target sequence is a function of the binding Tm and the susceptibility of the duplex to cellular enzymatic cleavage. The Tm of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol. Vol.* 154 pp. 94-107. In certain embodiments, antisense oligomer may have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (50° C. or greater) at a length of 25 bases or less are generally preferred over those requiring greater than 25 bases for high Tm values.

Figure 9A:
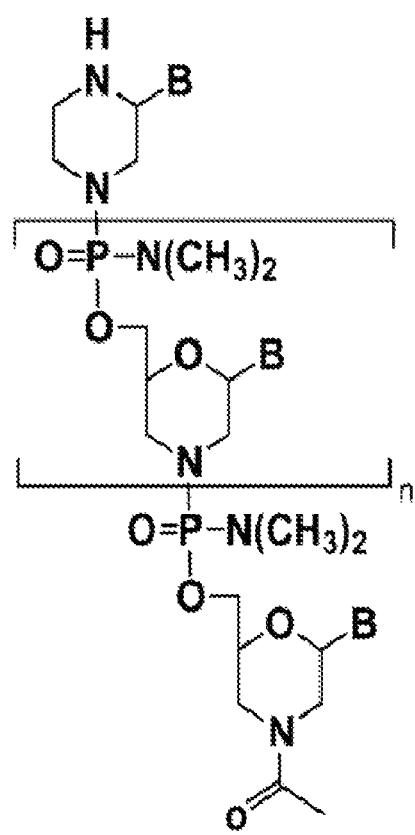
FIG. 9A shows an exemplary morpholino oligomer structure with a phosphorodiamidate linkage.
Figure 9B:
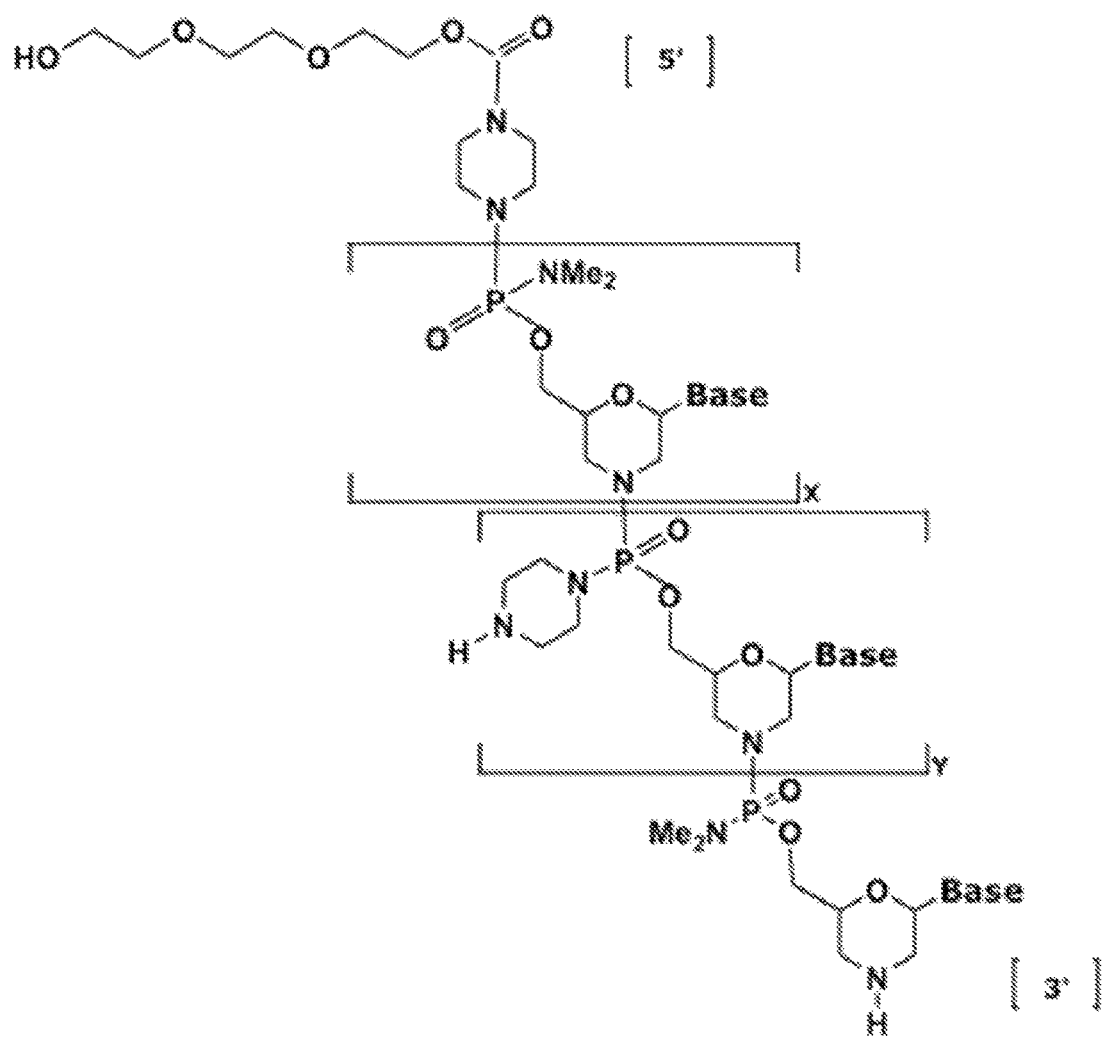
FIG. 9B shows a morpholino oligomer as in FIG. 1A, but where the backbone linkages contain one positively charged group in the form of a (piperazino) phosphorodiamidate linkage.

In certain embodiments, such as PMO oligomers, the antisense activity of an oligomer may be enhanced by using a mixture of uncharged and cationic phosphorodiamidate linkages, as exemplified in FIG. 9B. The total number of cationic linkages in the oligomer can vary from 1 to 10 (including all integers in between), and be interspersed throughout the oligomer. Preferably the number of charged linkages is at least 2 and no more than half the total backbone linkages, e.g., between 2, 3, 4, 5, 6, 7, or 8 positively charged linkages, and preferably each charged linkage is separated along the backbone by at least 1, 2, 3, 4, or 5 uncharged linkages. The antisense activity of various oligomers can be measured in vitro by fusing the oligomer target region to the 5' end a reporter gene (e.g., firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Exemplary antisense sequences for targeting p53 are shown in Table 4 below. Antisense oligonucleotides can comprise all or a portion of these targeting sequences.

TABLE 4

EXEMPLARY P53 TARGETING SEQUENCES

| PMO | p53 Region | Targeting Sequence 5'-3' | SEQ ID NO: |
|---|---|---|---|
| M1 | AUG start codon | GCGGCTCCTCCATGGCAGTGAC | 3 |

TABLE 4-continued

EXEMPLARY P53 TARGETING SEQUENCES

| PMO | p53 Region | Targeting Sequence 5'-3' | SEQ ID NO: |
|---|---|---|---|
| M40 | Met 40 AUG codon | CATCAAATCATCCATTGCTTGG | 4 |
| E2SD | Exon 2 | AGTTTCCATAGGTCTGAAAA | 5 |
| E4SA | Intron 3/ Exon 4 | GIIIACTGTAGATGIGTGAA | 6 |
| E6SA | Exon 6 | CGGATAAGATGCTGAGGAGG | 7 |
| E7SA | Exon 7 | GTTGTAGTGGATGGTGGTA | 8 |
| E7SD | Exon 7 | CTGGAGTCTTCCAGTGTGAT | 9 |
| E9SD | Exon 9 | AAGIGTGAAATATTCTCCATC | 10 |
| E10SA | Intron 9/ Exon 10 | GCGCTCACGCCCACGGATC | 11 |
| E10 | Exon 10 (Internal) | CCCTGCTCCCCCCTGGCTCC | 12 |

3. Antisense Oligonucleotide Compounds

The antisense oligonucleotides of the present invention typically (a) have the ability to be actively taken up by mammalian cells, and (b) once taken up, form a duplex with the target RNA with a Tm greater than about 45° C. In certain embodiments, the oligomer backbone may be substantially uncharged, and, preferably, may be recognized as a substrate for active or facilitated transport across the cell membrane. The ability of the oligomer to form a stable duplex with the target RNA may also relate to other features of the oligomer backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm. Included are antisense oligomers composed of PMO, PMO+ (PMOplus), PMO-X, LNA, PNAs, and/or 2'O-Me-based chemistries, described herein. In general, PNA and LNA chemistries utilize shorter targeting oligomers due to their relatively high target binding strength compared to PMO and 2'O-Me oligomers.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

PNAs are produced synthetically using any technique known in the art. PNA is a DNA analog in which a polyamide backbone replaces the traditional phosphate ribose ring of DNA as shown below.

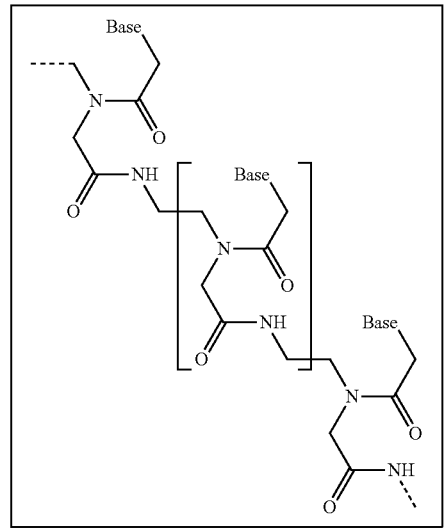

Despite a radical structural change to the natural structure, PNA is capable of sequence-specific binding in a helix form to DNA or RNA. Characteristics of PNA include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene™ has developed its proprietary Bts PNA monomers (Bts; benzothiazole-2-sulfonyl group) and proprietary oligomerisation process. The PNA oligomerisation using Bts PNA monomers is composed of repetitive cycles of deprotection, coupling and capping. Panagene's patents to this technology include U.S. Pat. No. 6,969,766, U.S. Pat. No. 7,211,668, U.S. Pat. No. 7,022,851, U.S. Pat. No. 7,125,994, U.S. Pat. No. 7,145,006 and U.S. Pat. No. 7,179,896. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

Oligonucleotide compounds may also contain "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008)16, 9230. Exemplary, non-limiting LNA structures are illustrated below:

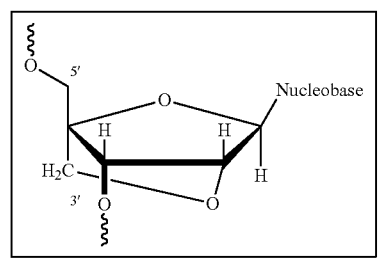

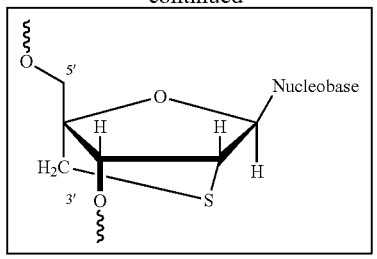

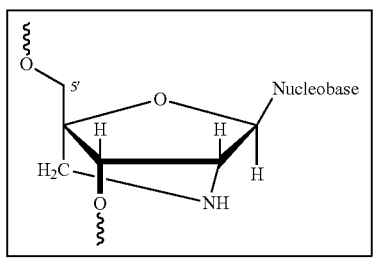

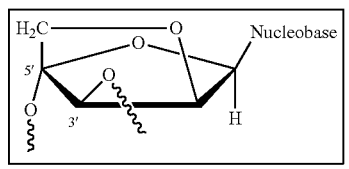

Compounds of the invention may incorporate one or more LNAs; in some cases, the compounds may be entirely composed of LNAs. Methods for the synthesis of individual LNA nucleoside subunits and their incorporation into oligonucleotides are known in the art: U.S. Pat. Nos. 7,572,582; 7,569,575; 7,084,125; 7,060,809; 7,053,207; 7,034,133; 6,794,499; and 6,670,461. Typical intersubunit linkers include phosphodiester and phosphorothioate moieties; alternatively, non-phosphorous containing linkers may be employed. A preferred embodiment is an LNA containing compound where each LNA subunit is separated by a DNA subunit (i.e., a deoxyribose nucleotide). Further preferred compounds are composed of alternating LNA and DNA subunits where the intersubunit linker is phosphorothioate.

A preferred oligomer structure employs morpholino-based subunits bearing base-pairing moieties, joined by uncharged linkages, as described above. Especially preferred is a substantially uncharged phosphorodiamidate-linked morpholino oligomer (PMO). Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, and in PCT application No. US08/088339, all of which are incorporated by reference.

Certain properties of the morpholino-based subunits include: the ability to be linked in a oligomeric form by stable, uncharged backbone linkages; the ability to support a nucleotide base (e.g., adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNase degradation.

Properties of the morpholino-based subunits include: 1) the ability to be linked in a oligomeric form by stable, uncharged or positively charged backbone linkages; 2) the ability to support a nucleotide base (e.g., adenine, cytosine, guanine, thymidine, uracil and hypoxanthine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNase and RNaseH degradation, respectively.

Figure 9C:
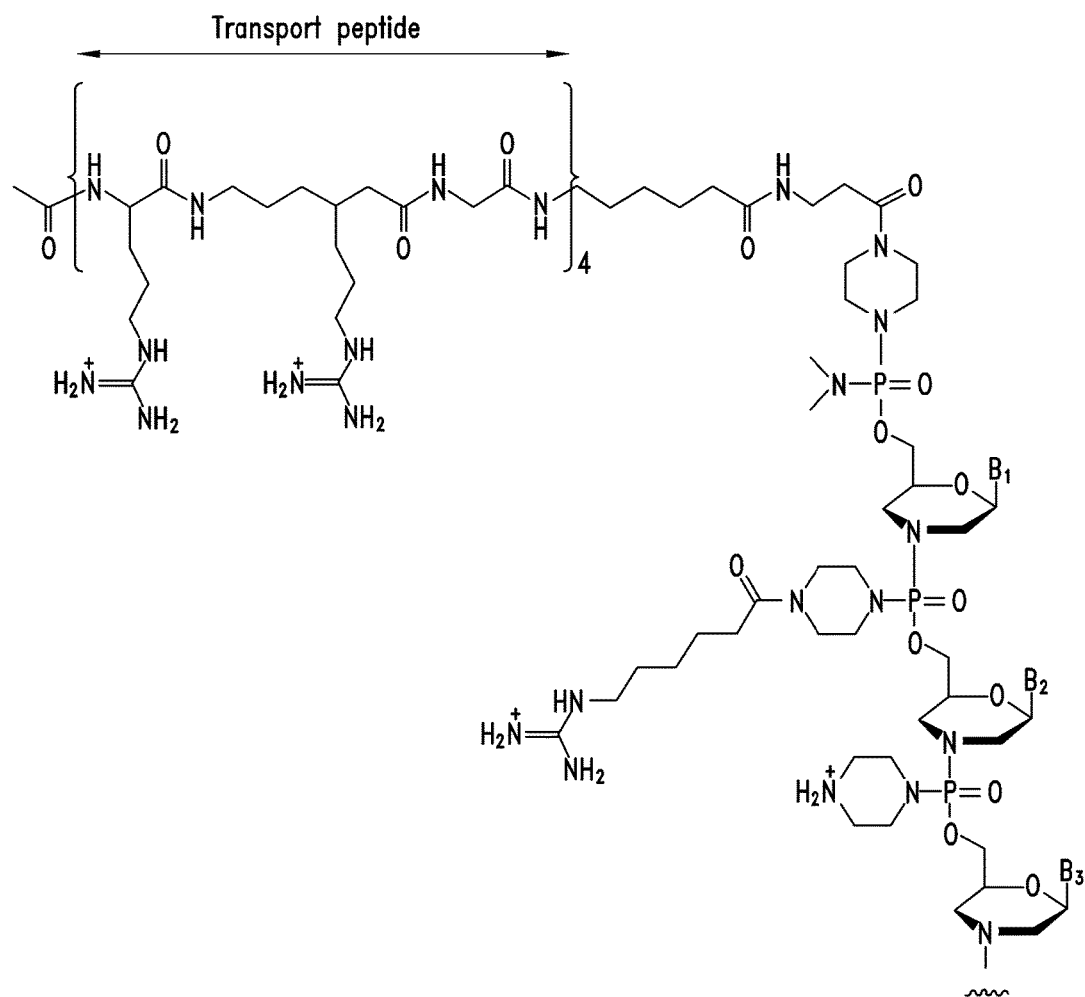
FIG. 9C shows a conjugate of an arginine-rich peptide and an antisense oligomer, in accordance with one embodiment of the invention.
Figure 9D:
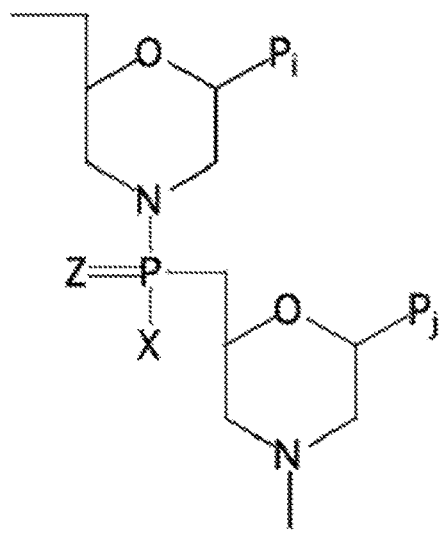
FIGS. 9D-G show the repeating subunit segment of exemplary morpholino oligonucleotides, designated D through G.
Figure 9E:
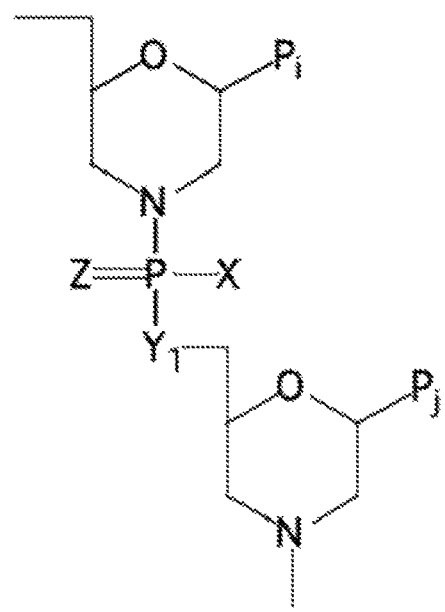

Examples of morpholino oligonucleotides having phosphorus-containing backbone linkages are illustrated in FIGS. 9A-9C. Especially preferred is a phosphorodiamidate-linked morpholino oligonucleotide, as shown in FIG. 9B, which is modified, in accordance with one aspect of the present invention, to contain positively charged groups at preferably 10%-50% of its backbone linkages. Exemplary backbone structures for antisense oligonucleotides of the claimed subject matter include the morpholino subunit types shown in FIGS. 9D-9G, each linked by an uncharged or positively charged, phosphorus-containing subunit linkage. FIG. 9D shows a phosphorus-containing linkage which forms the five atom repeating-unit backbone, where the morpholino rings are linked by a 1-atom phosphoamide linkage. FIG. 9E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 9F:
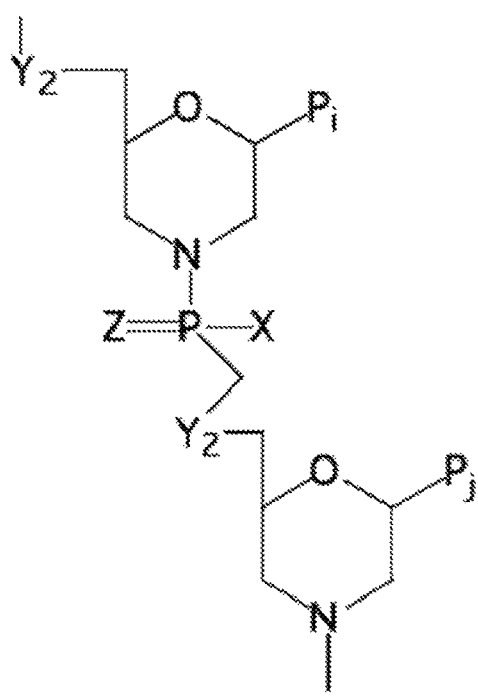
Figure 9G:
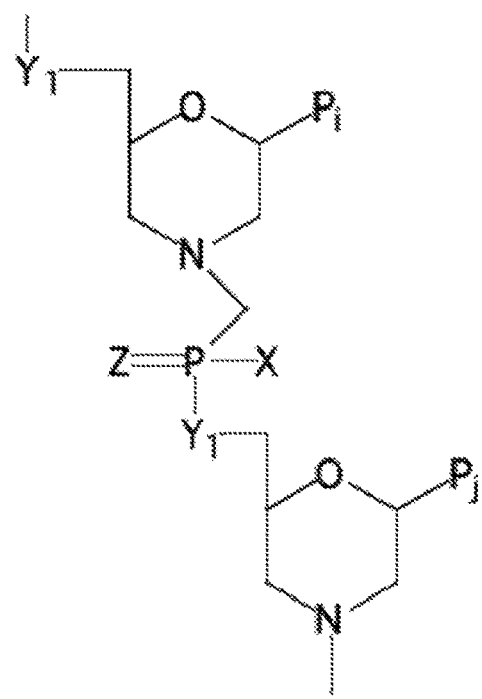

The linkages shown in FIGS. 9F and 9G are designed for 7-atom unit-length backbones. In FIG. 9F, the X moiety is as in FIG. 9E, and the Y moiety may be methylene, sulfur, or, preferably, oxygen. In FIG. 9G, the X and Y moieties are as FIG. 9E. Particularly preferred morpholino oligonucleotides include those composed of morpholino subunit structures of the form shown in FIG. 9E, where X=NH$_2$, N(CH$_3$)$_2$, or 1-piperazine or other charged group, Y=O, and Z=O.

As noted above, the substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%. The enhancement seen with added cationic backbone charges may, in some cases, be further enhanced by distributing the bulk of the charges close of the "center-region" backbone linkages of the antisense oligonucleotide, e.g., in a 20-mer oligonucleotide with 8 cationic backbone linkages, having at least 70% of these charged linkages localized in the 10 centermost linkages.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, certain of the antisense compounds can be constructed to contain a selected number of cationic linkages interspersed with uncharged linkages of the type described above. The intersubunit linkages, both uncharged and cationic, preferably are phosphorus-containing linkages, having the structure:

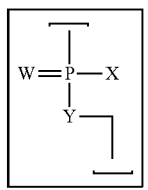

where
W is S or O, and is preferably O,
$X=NR^1R^2$ or $OR^6$,
$Y=O$ or $NR^7$,
and each said linkage in the oligomer is selected from:
(a) uncharged linkage (a), where each of $R^1$, $R^2$, $R^6$ and $R^7$ is independently selected from hydrogen and lower alkyl;
(b1) cationic linkage (b1), where $X=NR'R^2$ and $Y=O$, and $NR^1R^2$ represents an optionally substituted piperazino group, such that $R^1R^2=$—CHRCHRN($R^3$)($R^4$)CHRCHR—, where
  each R is independently H or $CH_3$,
  $R^4$ is H, $CH_3$, or an electron pair, and
  $R^3$ is selected from H, lower alkyl, e.g., $CH_3$, C(=NH)$NH_2$, Z-L-NHC(=NH)$NH_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;

(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy)alkyl; and (b3) cationic linkage (b3), where $Y=NR'$ and $X=OR^6$, and $R^7=LNR^3R^4R^5$, where L, $R^3$, $R^4$ and $R^5$ are as defined above, and $R^6$ is H or lower alkyl;

and at least one said linkage is selected from cationic linkages (1), (b2), and (b3).

In certain embodiments, an oligomer may include at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g., $CH_3$, C(=NH)$NH_2$, and C(O)-L-NHC(=NH)$NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g., —$CH_2$—$CH_2$—), alkoxy (—C—O—), and alkylamino (e.g., —$CH_2$—NH—), with the proviso that the terminal atoms in L (e.g., those adjacent to carbonyl or nitrogen) are carbon atoms. Although branched linkages (e.g., —$CH_2$—$CHCH_3$—) are possible, the linker is preferably unbranched. In one embodiment, the linker is a hydrocarbon linker. Such a linker may have the structure —($CH_2$)$_n$—, where n is 1-12, preferably 2-8, and more preferably 2-6.

The morpholino subunits may have the structure:

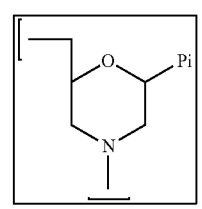

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

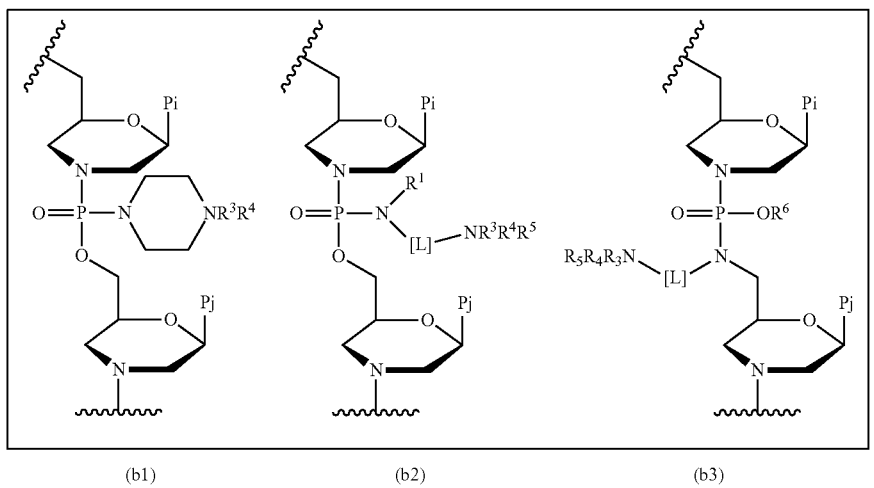

(b1)　　　　(b2)　　　　(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1') is referred to herein as a "Pip" linkage and (b1") is referred to herein as a "GuX" linkage:

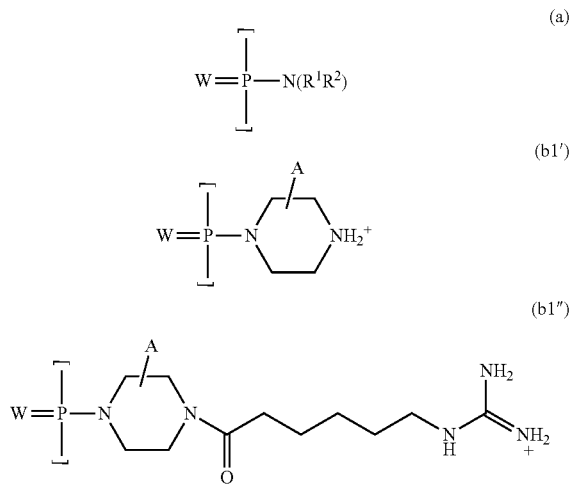

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted. In further embodiments, at least 10% of the linkages are of type (b1') or (b1"); for example, 10%-60% and preferably 20% to 50%, of the linkages may be of type (b1') or (b1").

In certain embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5' nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

As noted above, certain embodiments are directed to oligomers comprising novel intersubunit linkages, including PMO-X oligomers and those having modified terminal groups. In some embodiments, these oligomers have higher affinity for DNA and RNA than do the corresponding unmodified oligomers and demonstrate improved cell delivery, potency, and/or tissue distribution properties compared to oligomers having other intersubunit linkages. In one embodiment, the oligomers comprise at least one intersubunit linkage of type (B) as defined herein. The oligomers may also comprise one or more intersubunit linkages of type (A) as defined herein. The structural features and properties of the various linkage types and oligomers are described in more detail in the following discussion. The synthesis of these and related oligomers is described in co-owned WO2011/150408 and US2012/0065169, which are incorporated herein by reference in their entireties. Further oligomers of the PMO-X type useful herein may be found in U.S. Provisional Application No. 61/561,806, filed Nov. 18, 2011, which is incorporated herein by reference in its entirety.

Linkage (A)

Applicants have found that enhancement of antisense activity, biodistribution and/or other desirable properties can be optimized by preparing oligomers having various intersubunit linkages. For example, the oligomers may optionally comprise one or more intersubunit linkages of type (A), and in certain embodiments the oligomers comprise at least one linkage of type (A). In some other embodiments each linkage of type (A) has the same structure. Linkages of type (A) may include linkages disclosed in co-owned U.S. Pat. No. 7,943,762 which is hereby incorporated by reference in its entirety. Linkage (A) has the following structure (I), wherein 3' and 5' indicate the point of attachment to the 3' and 5' ends, respectively, of the morpholino ring (i.e., structure (i) discussed below):

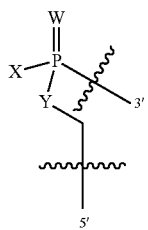

or a salt or isomer thereof, wherein:

W is, at each occurrence, independently S or O;

X is, at each occurrence, independently —N(CH$_3$)$_2$, —NR$^1$R$^2$, —OR$^3$ or;

Y is, at each occurrence, independently O or —NR$^2$,

R$^1$ is, at each occurrence, independently hydrogen or methyl;

R$^2$ is, at each occurrence, independently hydrogen or -LNR$^4$R$^5$R$^7$;

R$^3$ is, at each occurrence, independently hydrogen or C$_1$-C$_6$ alkyl;

R$^4$ is, at each occurrence, independently hydrogen, methyl, —C(=NH)NH$_2$, —Z-L-NHC(=NH)NH$_2$ or —[C(=O)CHR'NH]$_m$H, where Z is —C(=O)— or a direct bond, R' is a side chain of a naturally occurring amino acid or a one- or two-carbon homolog thereof, and m is 1 to 6;

R$^5$ is, at each occurrence, independently hydrogen, methyl or an electron pair;

R$^6$ is, at each occurrence, independently hydrogen or methyl;

R$^7$ is, at each occurrence, independently hydrogen C$_1$-C$_6$ alkyl or C$_1$-C$_6$ alkoxyalkyl; and L is an optional linker up to 18 atoms in length comprising alkyl, alkoxy or alkylamino groups, or combinations thereof.

In some examples, the oligomer comprises at least one linkage of type (A). In some other embodiments, the oligomer includes at least two consecutive linkages of type (A). In further embodiments, at least 5% of the linkages in the oligomer are type (A); for example in some embodiments, 5%-95%, 10% to 90%, 10% to 50%, or 10% to 35% of the linkages may be linkage type (A). In some specific embodiments, at least one type (A) linkage is —N(CH$_3$)$_2$. In other embodiments, each linkage of type (A) is —N(CH$_3$)$_2$. In other embodiments, at least one type (A) linkage is piperizin-1-yl, for example unsubstituted piperazin-1-yl (e.g., A2 or A3). In other embodiments, each linkage of type (A) is piperizin-1-yl, for example unsubstituted piperazin-1-yl.

The linker group L, as noted above, contains bonds in its backbone selected from alkyl (e.g. —CH2-CH2-), alkoxy (e.g., —C—O—C—), and alkylamino (e.g. —CH2-NH—), with the proviso that the terminal atoms in L (e.g., those adjacent to carbonyl or nitrogen) are carbon atoms. Although branched linkages (e.g. —CH2-CHCH3-) are possible, the linker is generally unbranched. In one embodiment, the linker is a hydrocarbon linker. Such a linker may have the structure (CH2)$_n$—, where n is 1-12, preferably 2-8, and more preferably 2-6.

Oligomers having any number of linkage type (A) are provided. In some embodiments, the oligomer contains no linkages of type (A). In certain embodiments, 5, 10, 20, 30, 40, 50, 60, 70, 80 or 90 percent of the linkages are linkage (A). In selected embodiments, 10 to 80, 20 to 80, 20 to 60, 20 to 50, 20 to 40, or 20 to 35 percent of the linkages are linkage (A).

Linkage (B)

In some embodiments, the oligomers comprise at least one linkage of type (B). For example the oligomers may comprise 1, 2, 3, 4, 5, 6 or more linkages of type (B). The type (B) linkages may be adjacent or may be interspersed throughout the oligomer. Linkage type (B) has the following structure (I):

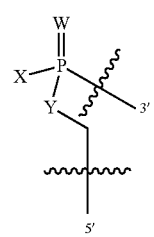

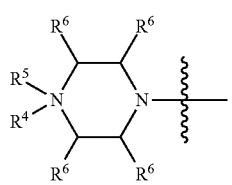

or a salt or isomer thereof, wherein:

W is, at each occurrence, independently S or O;

X is, at each occurrence, independently —NR$^8$R$^9$ or —OR$^3$; and

Y is, at each occurrence, independently O or —NR$^{10}$,

R$^3$ is, at each occurrence, independently hydrogen or C$_1$-C$_6$ alkyl;

R$^8$ is, at each occurrence, independently hydrogen or C$_2$-C$_{12}$ alkyl;

R$^9$ is, at each occurrence, independently hydrogen, C$_1$-C$_{12}$ alkyl, C$_1$-C$_{12}$ aralkyl or aryl;

R$^{10}$ is, at each occurrence, independently hydrogen, C$_1$-C$_{12}$ alkyl or -LNR$^4$R$^5$R$^7$;

wherein R$^8$ and R$^9$ may join to form a 5-18 membered mono or bicyclic heterocycle or R$^8$, R$^9$ or R$^3$ may join with R$^{10}$ to form a 5-7 membered heterocycle, and wherein when X is 4-piparazino, X has the following structure (III):

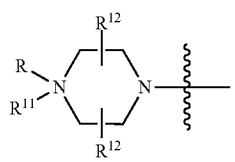

(III)

wherein:

R$^{11}$ is, at each occurrence, independently C$_2$-C$_{12}$ alkyl, C$_1$-C$_{12}$ aminoalkyl, C$_1$-C$_{12}$ alkylcarbonyl, aryl, heteroaryl or heterocyclyl;

R is, at each occurrence, independently an electron pair, hydrogen or C$_1$-C$_{12}$ alkyl; and R$^{12}$ is, at each occurrence, independently, hydrogen, C$_1$-C$_{12}$ alkyl, C$_1$-C$_{12}$ aminoalkyl, —NH$_2$, —NR$^{13}$R$^{14}$, —NR$^{13}$R$^{14}$R$^{15}$, C$_1$-C$_{12}$ alkylcarbonyl, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —SR$^{13}$ or C$_1$-C$_{12}$ alkoxy, wherein R$^{13}$, R$^{14}$ and R$^{15}$ are, at each occurrence, independently C$_1$-C$_{12}$ alkyl.

In some examples, the oligomer comprises one linkage of type (B). In some other embodiments, the oligomer comprises two inkages of type (B). In some other embodiments, the oligomer comprises three linkages of type (B). In some other embodiments, the oligomer comprises four linkages of type (B). In still other embodiments, the linkages of type (B) are consecutive (i.e., the type (B) linkages are adjacent to each other). In further embodiments, at least 5% of the linkages in the oligomer are type (B); for example in some embodiments, 5%-95%, 10% to 90%, 10% to 50%, or 10% to 35% of the linkages may be linkage type (B).

In certain embodiment, linkage (B) does not have any of the structures A1-A5. Table 5 shows representative linkages of type (A) and (B).

TABLE 5

| No. | Name | Structure |
|---|---|---|
| A1 | PMO | 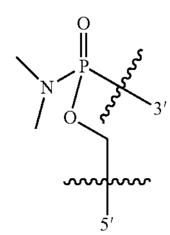 |
| A2 | PMO$^+$ (unprotonated form depicted) | 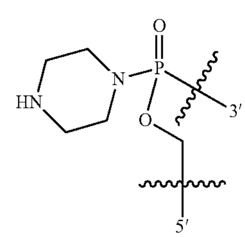 |
| A3 | PMO$^+$ (+) | 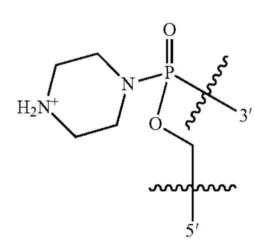 |

TABLE 5-continued

Representative Intersubunit Linkages

| No. | Name | Structure |
|---|---|---|
| A4 | PMO$^{nepip}$ (m+) | 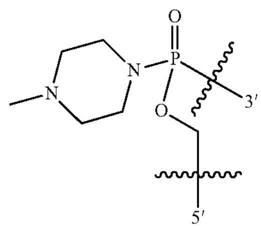 |
| A5 | PMO$^{GUX}$ | 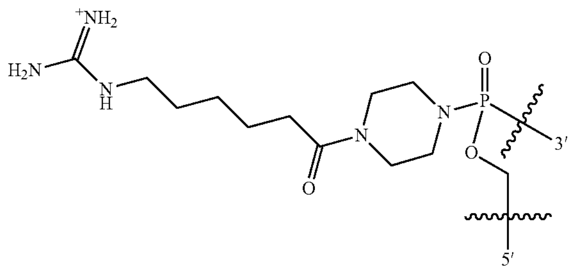 |
| B1 | PMO$^{cp}$ | 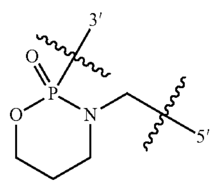 |
| B2 | PMO$^{cps}$ | 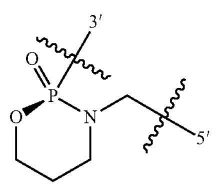 |
| B3 | PMO$^{cpr}$ | 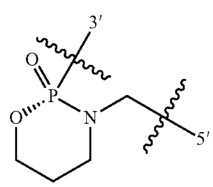 |
| B4 | PMO$^{Shc}$ | 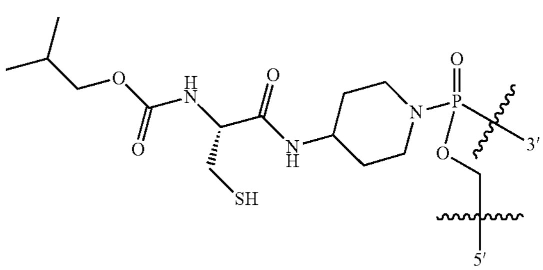 |
| B5 | PMO$^{morpholino}$ (m) | 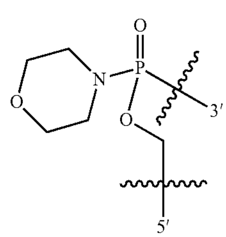 |

TABLE 5-continued

Representative Intersubunit Linkages

| No. | Name | Structure |
|---|---|---|
| B6 | PMO$^{tri}$ (t) | 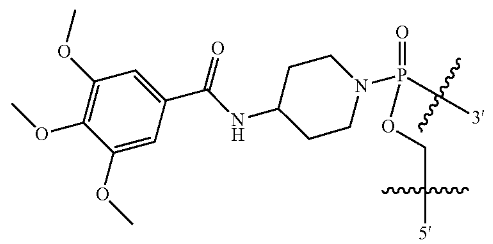 |
| B7 | PMO$^{hex}$ (h) | 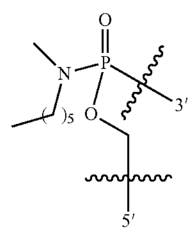 |
| B8 | PMO$^{dodec}$ | 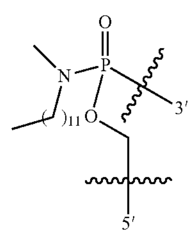 |
| B9 | PMO$^{dihex}$ | 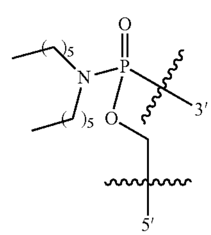 |
| B10 | PMO$^{apn}$ (a) | 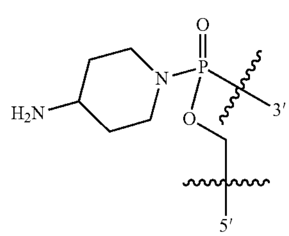 |
| B11 | PMO$^{pyr}$ (p) | 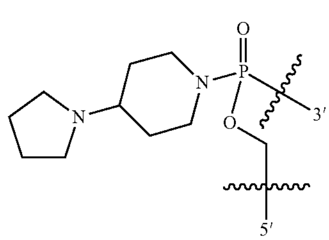 |

TABLE 5-continued

Representative Intersubunit Linkages

| No. | Name | Structure |
|---|---|---|
| B12 | PMO$^{pyr}$ (HCl Salt) | 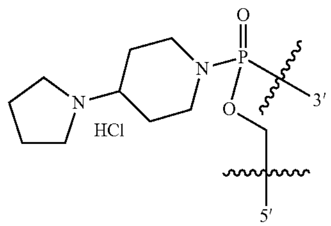 |
| B13 | PMO$^{rba}$ | 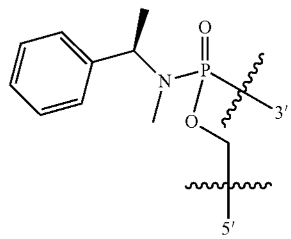 |
| B14 | PMO$^{sba}$ | 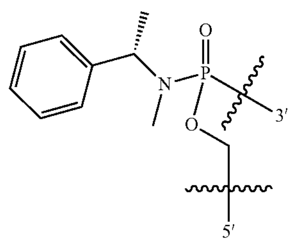 |
| B15 | PMO$^{dimethylapn}$ | 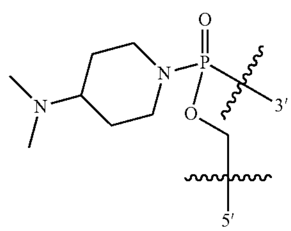 |
| B16 | PMO$^{etpip}$ | 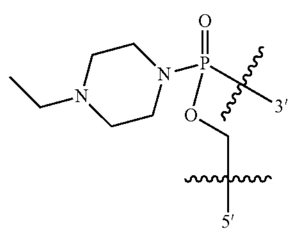 |
| B17 | PMO$^{iprpip}$ | 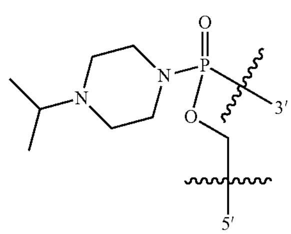 |

TABLE 5-continued

Representative Intersubunit Linkages

| No. | Name | Structure |
|---|---|---|
| B18 | PMO$^{pyrQMe}$ | 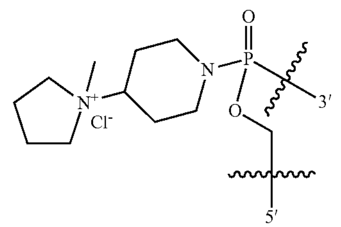 |
| B19 | PMO$^{cb}$ | 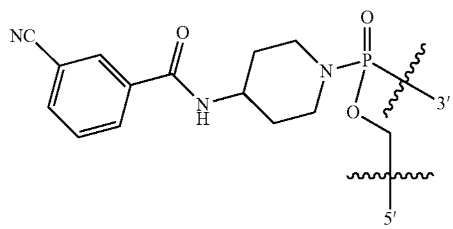 |
| B20 | PMO$^{ma}$ | 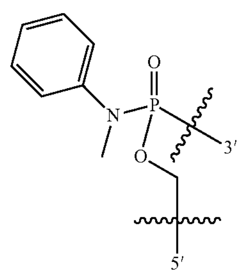 |
| B21 | PMO$^{bu}$ | 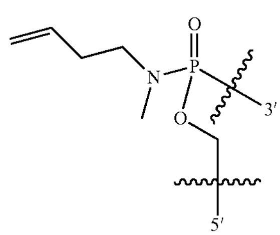 |
| B22 | PMO$^{bi}$ | 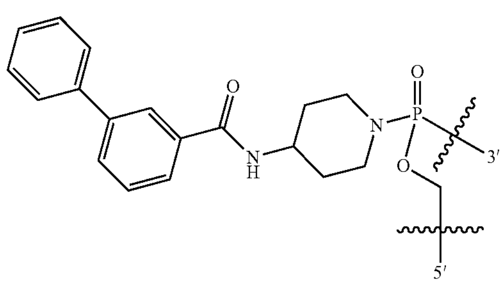 |
| B23 | PMO$^{pip}$ | 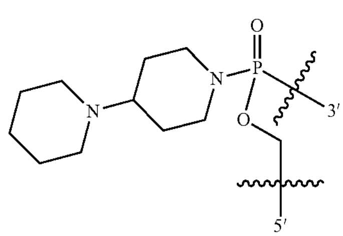 |

TABLE 5-continued

Representative Intersubunit Linkages

| No. | Name | Structure |
|---|---|---|
| B24 | PMO$^{odmb}$ | 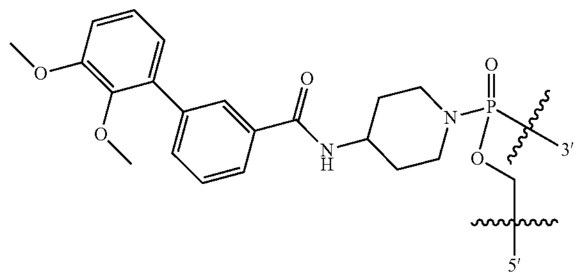 |
| B25 | PMO$^{tfb}$ | 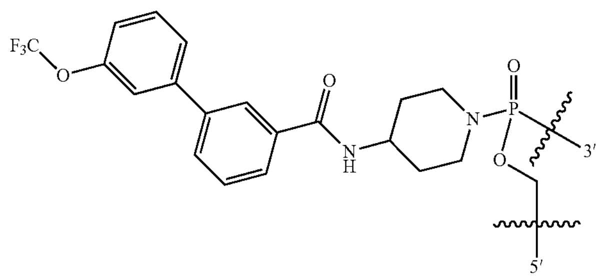 |
| B26 | PMO$^{ctfb}$ | 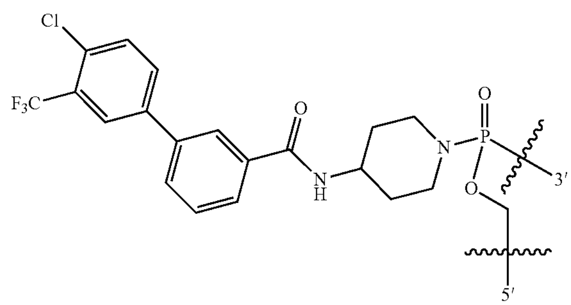 |
| B27 | PMO$^{ptfb}$ | 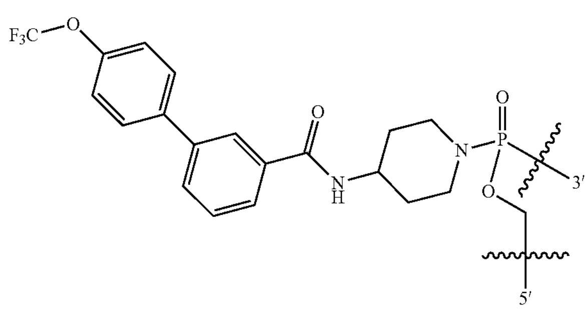 |
| B28 | PMO$^{dcb}$ | 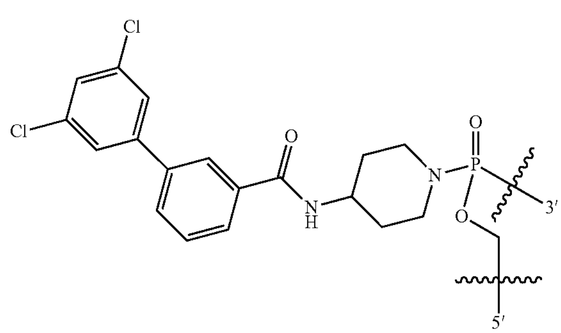 |

TABLE 5-continued

Representative Intersubunit Linkages

| No. | Name | Structure |
|---|---|---|
| B29 | PMO$^{dmb}$ | 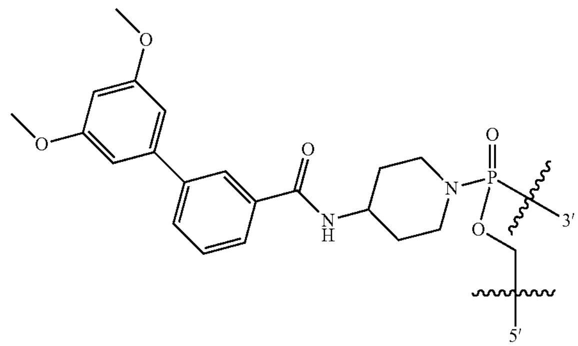 |
| B30 | PMO$^{hy}$ | 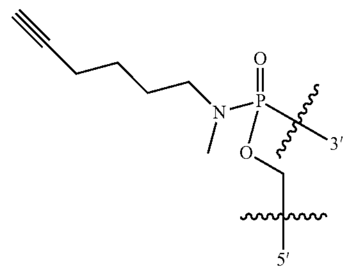 |
| B31 | PMO$^{6ce}$ | 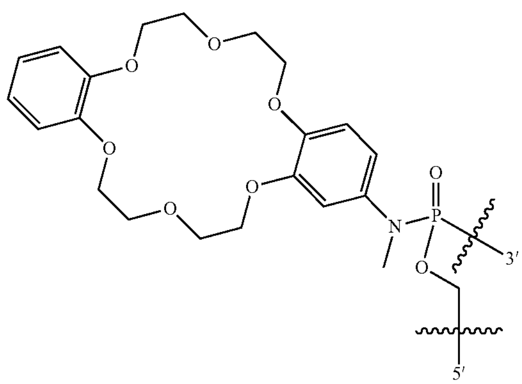 |
| B32 | PMO$^{b}$ | 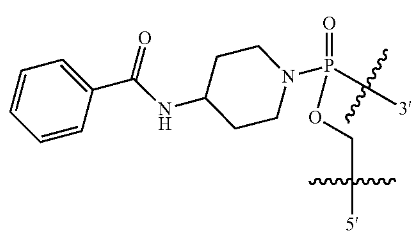 |
| B33 | PMO$^{q}$ | 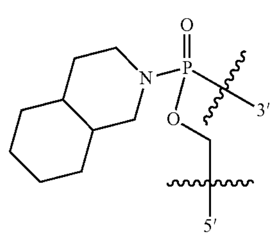 |

TABLE 5-continued
Representative Intersubunit Linkages
| No. | Name | Structure |
|---|---|---|
| B34 | PMO^npp | 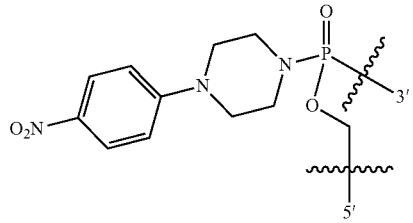 |
| B35 | PMO^o | 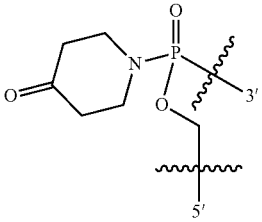 |
| B36 | PMO^4ce | 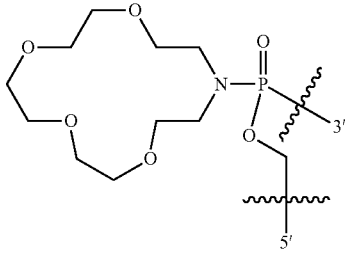 |
| B37 | PMO^5ce | 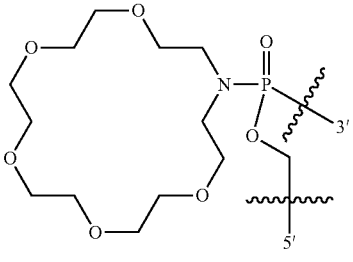 |
| B38 | PMO^f3p | 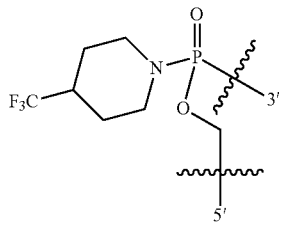 |
| B39 | PMO^cyp | 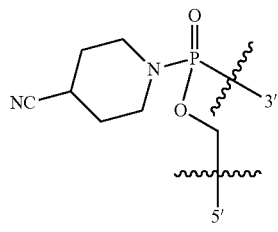 |

TABLE 5-continued

Representative Intersubunit Linkages

| No. | Name | Structure |
|---|---|---|
| B40 | PMO$^{mop}$ | 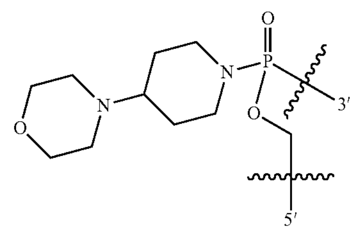 |
| B41 | PMO$^{pp}$ | 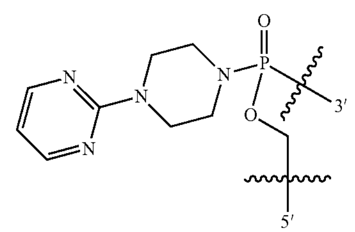 |
| B42 | PMO$^{dmepip}$ | 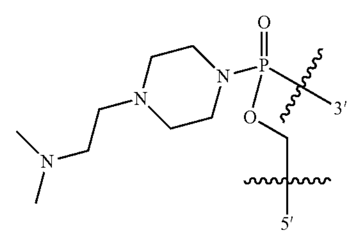 |
| B43 | PMO$^{NPpip}$ | 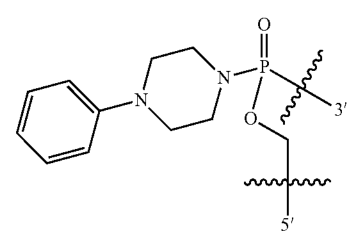 |
| B44 | PMO$^{bipip}$ | 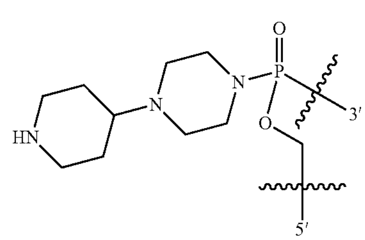 |
| B45 | PMO$^{suc}$ | 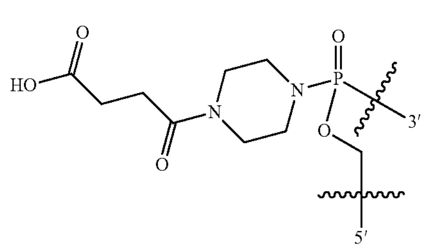 |

TABLE 5-continued

Representative Intersubunit Linkages

| No. | Name | Structure |
|---|---|---|
| 46 | PMO*glutaric* | 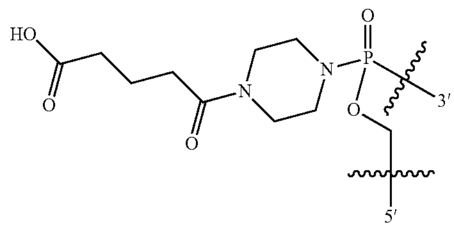 |
| B47 | PMO*tet* | 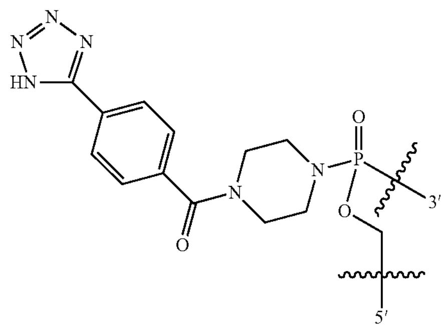 |
| B48 | PMO*thiol* (SH) | 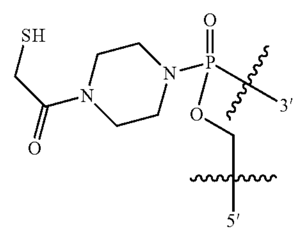 |
| B49 | PMO*pros* | 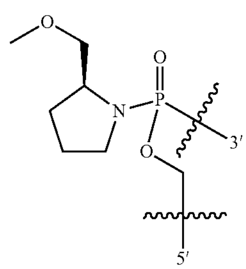 |
| B50 | PMO*pror* | 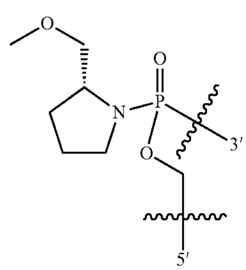 |
| B51 | PMO*tme* | 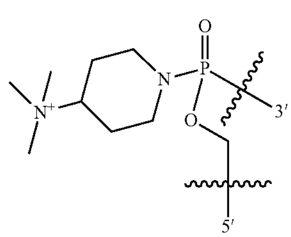 |

TABLE 5-continued
Representative Intersubunit Linkages
| No. | Name | Structure |
|---|---|---|
| B52 | PMO$^{ca}$ | 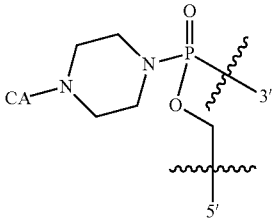<br>CA = Cholate |
| B53 | PMO$^{dca}$ | 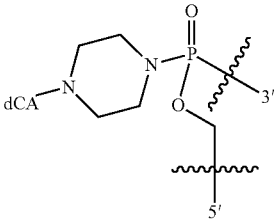<br>dCA = Cholate |
| B54 | PMO$^{guan}$ (g) | 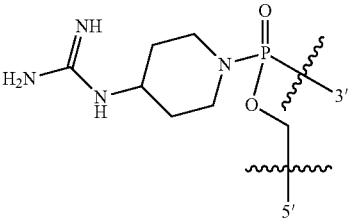 |
| B55 | PMO$^{+phos}$ | 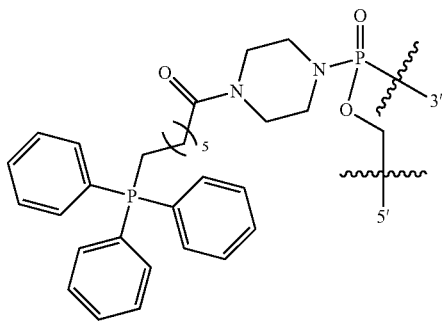 |
| B56 | PMO$^{apnphos}$ | 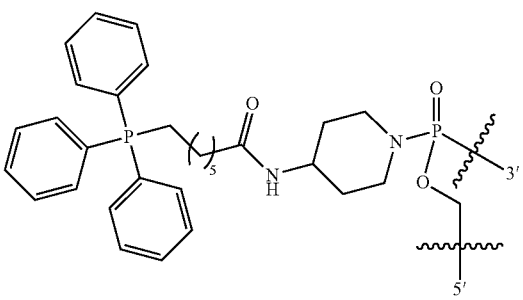 |

In the sequences and discussion that follows, the above names for the linkages are often used. For example, a base comprising a PMO$^{apn}$ linkage is illustrated as $^{apn}$B, where B is a base. Other linkages are designated similarly. In addition, abbreviated designations may be used, for example, the abbreviated designations in parentheses above may be used (e.g., $^a$B, refers to $^{apn}$B). Other readily identifiable abbreviations may also be used.

In a specific embodiment, an antisense oligonucleotide of the invention comprises PMO$^{apn}$ intersubunit linkages, e.g., as shown above as structure B10.

As noted above, the present disclosure also provides an oligomer comprising modified terminal groups. Applicants have found that modification of the 3' and/or 5' end of the oligomer with various chemical moieties provides beneficial therapeutic properties (e.g., enhanced cell delivery, potency, and/or tissue distribution, etc.) to the oligomers. In various embodiments, the modified terminal groups comprise a hydrophobic moiety, while in other embodiments the modified terminal groups comprise a hydrophilic moiety. The modified terminal groups may be present with or without the linkages described above. For example, in some embodiments, the oligomers comprise one or more modified terminal group and linkages of type (A), for example linkages wherein X is —N(CH$_3$)$_2$. In other embodiments, the oligomers comprise one or more modified terminal group and linkages of type (B), for example linkages wherein X is 4-aminopiperidin-1-yl (i.e., APN). In yet other embodiments, the oligomers comprise one or more modified terminal group and a mixture of linkages (A) and (B). For example, the oligomers may comprise one or more modified terminal group (e.g., trityl or triphenyl acetyl) and linkages wherein X is —N(CH$_3$)$_2$ and linkages wherein X is 4-aminopiperidin-1-yl. Other combinations of modified terminal groups and modified linkages also provide favorable therapeutic properties to the oligomers.

In one embodiment, the oligomers comprising terminal modifications have the following structure (XVII):

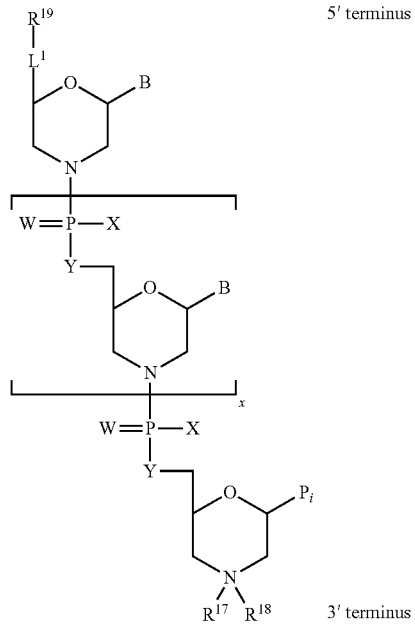

(XVII)

or a salt or isomer thereof, wherein X, W and Y are as defined above for any of linkages (A) and (B) and:

R$^{17}$ is, at each occurrence, independently absent, hydrogen or C$_1$-C$_6$ alkyl;

R$^{18}$ and R$^{19}$ are, at each occurrence, independently absent, hydrogen, a cell-penetrating peptide, a natural or non-natural amino acid, C$_2$-C$_{30}$ alkylcarbonyl, —C(=O)OR$^{21}$ or R$^{20}$;

R$^{20}$ is, at each occurrence, independently guanidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_3$-C$_{30}$ alkylcarbonyl, C$_3$-C$_8$ cycloalkylcarbonyl, C$_3$-C$_8$ cycloalkylalkylcarbonyl, C$_7$-C$_{30}$ arylcarbonyl, C$_7$-C$_{30}$ aralkylcarbonyl, C$_2$-C$_{30}$ alkyloxycarbonyl, C$_3$-C$_8$ cycloalkyloxycarbonyl, C$_7$-C$_{30}$ aryloxycarbonyl, C$_8$-C$_{30}$ aralkyloxycarbonyl, or —P(=O)(R$^{22}$)$_2$;

B is a base-pairing moiety;

L$^1$ is an optional linker up to 18 atoms in length comprising bonds selected from alkyl, hydroxyl, alkoxy, alkylamino, amide, ester, carbonyl, carbamate, phosphorodiamidate, phosphoroamidate, phosphorothioate, piperazine and phosphodiester; and x is an integer of 0 or greater; and wherein at least one of R$^{18}$ or R$^{19}$ is R$^{20}$; and wherein at least one of R$^{18}$ or R$^{19}$ is R$^{20}$ and provided that both of R$^{17}$ and R$^{18}$ are not absent.

The oligomers with modified terminal groups may comprise any number of linkages of types (A) and (B). For example, the oligomers may comprise only linkage type (A). For example, X in each linkage may be —N(CH$_3$)$_2$. Alternatively, the oligomers may only comprise linkage (B). In certain embodiments, the oligomers comprise a mixture of linkages (A) and (B), for example from 1 to 4 linkages of type (B) and the remainder of the linkages being of type (A). Linkages in this regard include, but are not limited to, linkages wherein X is aminopiperidinyl for type (B) and dimethyl amino for type (A).

In some embodiments the 3' terminus comprises a modification and in other embodiments the 5' terminus comprises a modification. In other embodiments both the 3' and 5' termini comprise modifications. Accordingly, in some embodiments, R$^{18}$ is absent and R$^{19}$ is R$^{20}$. In other embodiments, R$^{19}$ is absent and R$^{18}$ is R$^{20}$. In yet other embodiments, R$^{18}$ and R$^{19}$ are each R$^{20}$.

In some embodiments, the oligomer comprises a cell-penetrating peptide in addition to a 3' or 5' modification. Accordingly, in some embodiments R$^{19}$ is a cell-penetrating peptide and R$^{18}$ is R$^{20}$. In other embodiments, R$^{18}$ is a cell-penetrating peptide and R$^{19}$ is R$^{20}$. In further embodiments of the foregoing, the cell-penetrating peptide is an arginine-rich peptide.

In some embodiments, the linker L$^1$ which links the 5' terminal group (i.e., R$^{19}$) to the oligomer may be present or absent. The linker comprises any number of functional groups and lengths provided the linker retains its ability to link the 5' terminal group to the oligomer and provided that the linker does not interfere with the oligomer's ability to bind to a target sequence in a sequence specific manner. In one embodiment, L comprises phosphorodiamidate and piperazine bonds. For example, in some embodiments L has the following structure (XXIX):

(XXIX) 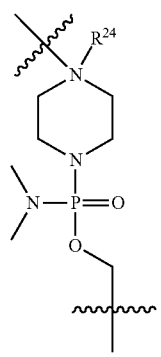

wherein $R^{24}$ is absent, hydrogen or $C_1$-$C_6$ alkyl. In some embodiments, $R^{24}$ is absent. In some embodiments, $R^{24}$ is hydrogen. In some embodiments, $R^{24}$ is $C_1$-$C_6$ alkyl. In some embodiments, $R^{24}$ is methyl. In other embodiments, $R^{24}$ is ethyl. In yet other embodiments, $R^{24}$ is $C_3$ alkyl. In some other embodiments, $R^{24}$ is isopropyl. In yet other embodiments, $R^{24}$ is $C_4$ alkyl. In some embodiments, $R^{24}$ is $C_5$ alkyl. In yet other embodiments, $R^{24}$ is $C_6$ alkyl.

In some other embodiments, only the 3' terminus of the oligomer is conjugated to one of the groups noted above. In some other embodiments, only the 5' terminus of the oligomer is conjugated to one of the groups noted above. In other embodiments, both the 3' and 5' termini comprise one of the groups noted above. In other embodiments, the terminal group may be selected from any one of the groups noted above or any of the specific groups illustrated in Table 6 below.

TABLE 6

Representative Terminal Groups

| No. | Name | Structure |
|---|---|---|
| C1 | Trimethoxybenzoyl | 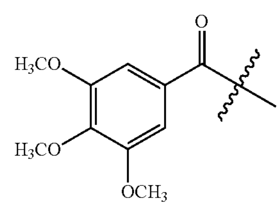 [SMILES: *C(=O)c1cc(OC)c(OC)c(OC)c1] |
| C2 | 9-fluorene-carboxyl | 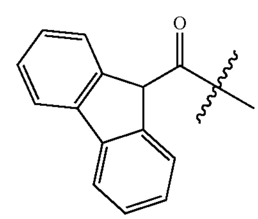 [SMILES: *C(=O)C1c2ccccc2-c2ccccc21] |
| C3 | 4-carbazolylbenzoyl | 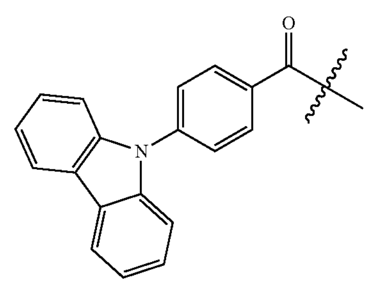 [SMILES: *C(=O)c1ccc(-n2c3ccccc3c3ccccc32)cc1] |
| C4 | 4-indazolylonebenzoyl | 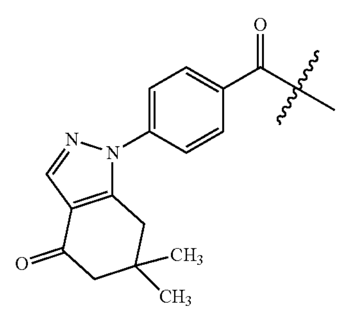 [SMILES: *C(=O)c1ccc(-n2ncc3c2CC(C)(C)CC3=O)cc1] |

TABLE 6-continued
Representative Terminal Groups
| No. | Name | Structure |
|---|---|---|
| C5 | Farnesyl | 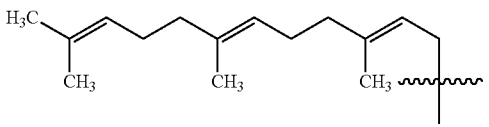 [SMILES: *C/C=C(\C)CC/C=C(\C)CCC=C(C)C] |
| C6 | Geranyl | 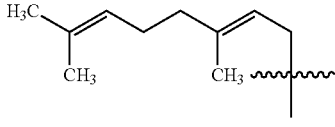 [SMILES: *C/C=C(\C)CCC=C(C)C] |
| C7 | Prenyl | 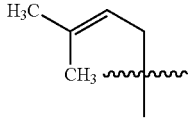 |
| C8 | Diphenylacetyl | 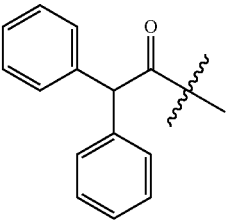 [SMILES: *C(=O)C(c1ccccc1)c1ccccc1] |
| C9 | Chlorodiphenylacetyl | 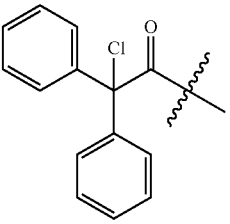 [SMILES: *C(=O)C(Cl)(c1ccccc1)c1ccccc1] |
| C10 | Hydroxydiphenylacetyl | 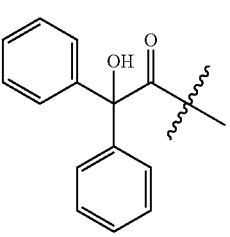 [SMILES: *C(=O)C(O)(c1ccccc1)c1ccccc1] |
| C11 | Triphenylpropionyl | 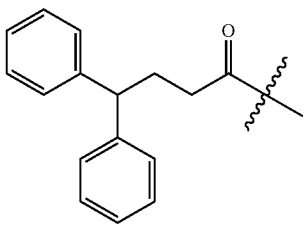 [SMILES: *C(=O)CCC(c1ccccc1)c1ccccc1] |

TABLE 6-continued
Representative Terminal Groups
| No. | Name | Structure |
|---|---|---|
| C12 | Triphenylpropyl | 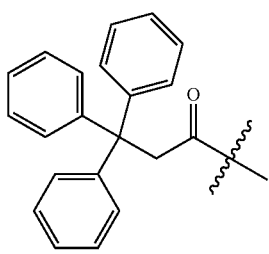 [SMILES: *C(=O)CC(c1ccccc1)(c1ccccc1)c1ccccc1] |
| C13 | Triphenylacetyl | 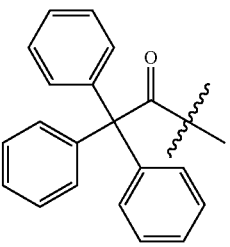 [SMILES: *C(=O)C(c1ccccc1)(c1ccccc1)c1ccccc1] |
| C14 | Trityl (Tr) | 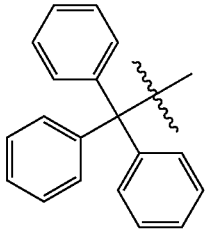 [SMILES: *C(c1ccccc1)(c1ccccc1)c1ccccc1] |
| C15 | Methoxytrityl (MeOTr) | 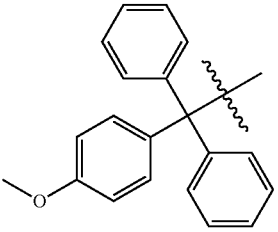 [SMILES: *C(c1ccccc1)(c1ccccc1)c1ccc(OC)cc1] |
| C16 | Methylsuccinimidyl-cyclohexoyl | 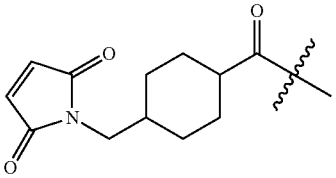 [SMILES: *C(=O)C1CCC(CN2C(=O)C=CC2=O)CC1] |
| C17 | Thioacetyl | 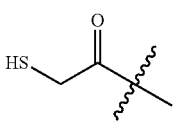 [SMILES: *C(=O)CS] |
| C18 | COCH$_2$CH$_2$SSPy | 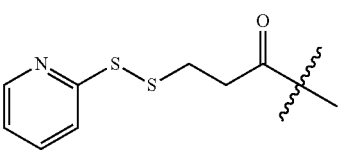 [SMILES: *C(=O)CCSSc1ccccn1] |

TABLE 6-continued
Representative Terminal Groups
| No. | Name | Structure |
|---|---|---|
| C19 | Guanidinyl | 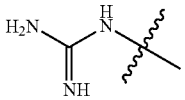 |
| C20 | Trimethylglycine | 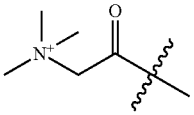 [SMILES: *C(=O)C[N+](C)(C)C] |
| C21 | Lauroyl | 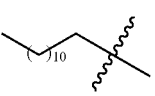 |
| C22 | Triethyleneglycoloyl (EG3) | 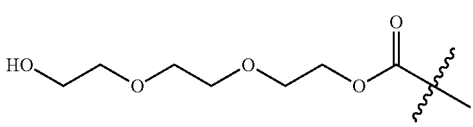 [SMILES: *C(=O)OCCOCCOCCO] |
| C23 | Succinicacetyl | 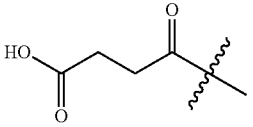 [SMILES: *C(=O)CCC(=O)O] |
| C24 | Diphenylphosphoryl | 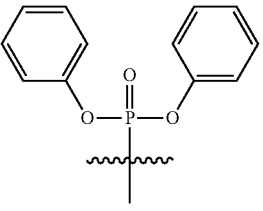 [SMILES: *P(=O)(Oc1ccccc1)Oc1ccccc1] |
| C25 | Piperidin-4-yl | 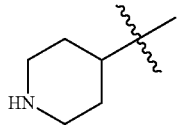 [SMILES: *C1CCNCC1] |
| C26 | Tritylpiperidin-4-yl | 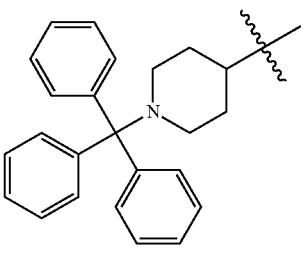 [SMILES: *C1CCN(C(c2ccccc2)(c2ccccc2)c2ccccc2)CC1] |
| C27 | Boc—Piperidin-4-yl | 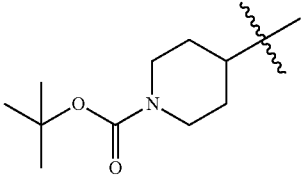 [SMILES: *C1CCN(C(=O)OC(C)(C)C)CC1] |
| C28 | Hexyn-6-yl | 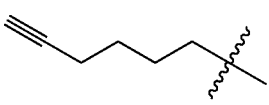 [SMILES: *CCCCC#C] |

TABLE 6-continued

Representative Terminal Groups

| No. | Name | Structure |
|---|---|---|
| C29 | 5-carboxyfluorescein | 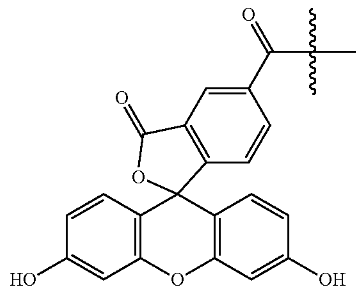 [SMILES: *C(=O)c1ccc2c(c1)C(=O)OC21c2ccc(O)cc2Oc2cc(O)ccc21] |
| C30 | Benzhydryl | 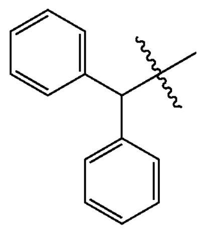 [SMILES: *C(c1ccccc1)c1ccccc1] |
| C31 | p-Chlorobenzhydryl | 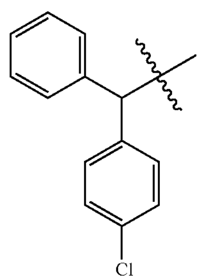 [SMILES: *C(c1ccccc1)c1ccc(Cl)cc1] |
| C32 | Piperazinyl (pip) | 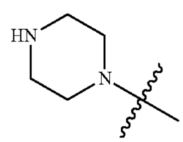 [SMILES: *N1CCNCC1] |
| C33 | Triphenylphos | 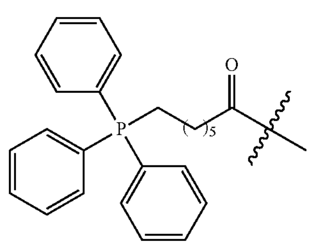 |
| C34 | Dimerized | 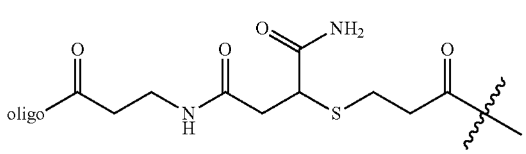 |

Oligo = a further oligomer

In a specific embodiment, an antisense oligonucleotide of the invention comprises at least one triphenylacetyl terminal group, e.g., as shown in structure C13 above.

In another specific embodiment, an antisense oligonucleotide of the invention comprises PMO$^{apn}$ intersubunit linkages, e.g., as shown above as structure B10, and further comprises at least one triphenylacetyl terminal group, e.g., as shown in structure C13 above.

4. Peptide Transporters

In some embodiments, the subject oligomer is conjugated to a peptide transporter moiety, for example a cell-penetrating peptide transport moiety, which is effective to enhance transport of the oligomer into cells. For example, in some embodiments the peptide transporter moiety is an arginine-rich peptide. In further embodiments, the transport moiety is attached to either the 5' or 3' terminus of the oligomer. When such peptide is conjugated to either termini, the opposite termini is then available for further conjugation to a modified terminal group as described herein.

In some embodiments of the foregoing, the peptide transport moiety comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^{33}N=C(NH_2)R^{34}$, where $R^{33}$ is H or R; $R^{34}$ is $R^{35}$, $NH_2$, NHR, or $NR_{34}$, where $R^{35}$ is lower alkyl or lower alkenyl and may further include oxygen or nitrogen; $R^{33}$ and $R^{34}$ may together form a ring; and the side chain is linked to said amino acid via $R^{33}$ or $R^{34}$;

(b) each Y' subunit independently represents a neutral amino acid —C(O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by one of (X'Y'X')$_p$, (X'Y')$_m$, and (X'Z'Z')$_p$, where p is 2 to 5 and m is 2 to 8.

In selected embodiments, for each X', the side chain moiety is guanidyl, as in the amino acid subunit arginine (Arg). In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit.

In certain embodiments, peptides of this type include those comprising arginine dimers alternating with single Y' subunits, where Y' is Ahx. Examples include peptides having the formula (RY'R)$_p$ or the formula (RRY')$_p$, where Y' is Ahx. In one embodiment, Y' is a 6-aminohexanoic acid subunit, R is arginine and p is 4.

In a further embodiment, each Z' is phenylalanine, and m is 3 or 4.

In some embodiments, the conjugated peptide is linked to a terminus of the oligomer via a linker Ahx-B, where Ahx is a 6-aminohexanoic acid subunit and B is a β-alanine subunit.

In selected embodiments, for each X', the side chain moiety is independently selected from the group consisting of guanidyl (HN=C(NH$_2$)NH—), amidinyl (HN=C(NH$_2$)C—), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In some embodiments, the Y' subunits are either contiguous, in that no X' subunits intervene between Y' subunits, or interspersed singly between X' subunits. However, in some embodiments the linking subunit may be between Y' subunits. In one embodiment, the Y' subunits are at a terminus of the peptide transporter; in other embodiments, they are flanked by X' subunits. In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Exemplary peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In some embodiments, the nucleic acid analog is linked to a terminal Y' subunit, preferably at the C-terminus. In other embodiments, the linker is of the structure AhxB, where Ahx is a 6-aminohexanoic acid subunit and B is a β-alanine subunit.

The peptide transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake may be evidenced by at least a two-fold increase, or in other embodiments a four-fold increase, in the uptake of the compound into mammalian cells relative to uptake of the agent by an attached transport moiety lacking the hydrophobic subunits Y'. In some embodiments, uptake is enhanced at least twenty fold or at least forty fold, relative to the unconjugated compound.

A further benefit of the peptide transport moiety is its expected ability to stabilize a duplex between an antisense oligomer and its target nucleic acid sequence. While not wishing to be bound by theory, this ability to stabilize a duplex may result from the electrostatic interaction between the positively charged transport moiety and the negatively charged nucleic acid. In some embodiments, the number of charged subunits in the transporter is less than 14, as noted above, or in other embodiments between 8 and 11, since too high a number of charged subunits may lead to a reduction in sequence specificity.

Exemplary arginine-rich cell-penetrating peptide transporters comprising linkers (B or AhxB) are given below in Table 7.

TABLE 7

ARGININE-RICH CELL-PENETRATING PEPTIDE TRANSPORTERS

| NAME (DESIGNATION) | SEQUENCE | SEQ ID NO.[A] |
|---|---|---|
| rTAT | RRRQRRKKR | 14 |
| Tat | RKKRRQRRR | 15 |
| R$_9$F$_2$ | RRRRRRRRRFF | 16 |
| R$_5$F$_2$R$_4$ | RRRRRFFRRRR | 17 |
| R$_4$ | RRRR | 18 |
| R$_5$ | RRRRR | 19 |
| R$_6$ | RRRRRR | 20 |

TABLE 7-continued

ARGININE-RICH CELL-PENETRATING PEPTIDE TRANSPORTERS

| NAME (DESIGNATION) | SEQUENCE | SEQ ID NO.[A] |
|---|---|---|
| $R_7$ | RRRRRRR | 21 |
| $R_8$ | RRRRRRRR | 22 |
| $R_9$ | RRRRRRRRR | 23 |
| $(RX)_8$ | RXRXRXRXRXRXRXRX | 24 |
| $(RAhxR)_4$; (P007) | RAhxRRAhxRRAhxRRAhxR | 25 |
| $(RAhxR)_5$; (CP04057) | RAhxRRAhxRRAhxRRAhxRRAhxR | 26 |
| $(RAhxRRBR)_2$; (CP06062) | RAhxRRBRRAhxRRBR | 27 |
| $(RAR)_4F_2$ | RARRARRARRARFFC | 28 |
| $(RGR)_4F_2$ | RGRRGRRGRRGRFFC | 29 |

[A]Sequences assigned to SEQ ID NOs do not include the linkage portion (e.g., C, G, Ahx, B, AhxB where Ahx and B refer to 6-aminohexanoic acid and beta-alanine, respectively).

5. Methods of Use

Another general aspect of the invention relates to uses of the antisense oligonucleotides and pharmaceutical compositions described herein in various methods of use. Therefore, in one aspect, provided herein is a method of inhibiting translation of an isoform of a cellular protein translated from a start codon of an mRNA that comprises at least two start codons. In some embodiments, the method comprises specifically hybridizing to said mRNA an antisense oligonucleotide of about 12 to 50, or about 12 to 40, nucleotides in length comprising a sequence substantially complementary to said start codon, wherein said antisense oligonucleotide inhibits translation of said isoform. In one aspect, provided herein is a method of inhibiting translation of a cellular protein translated from a first start codon of an mRNA that encodes at least two cellular proteins translated from at least two start codons of said mRNA. In some embodiments, the method comprises specifically hybridizing to said mRNA an antisense oligonucleotide of about 12 to 50, or about 12 to 40, nucleotides in length comprising a sequence substantially complementary to said first start codon, wherein said antisense oligonucleotide inhibits translation of said cellular protein. The antisense oligonucleotides useful in the methods provided herein include any of the antisense oligonucleotides described herein. mRNA targets and the protein isoforms encoded thereby can be any of the mRNA targets and protein isoforms described herein.

In some embodiments, hybridization of the antisense oligonucleotide to the target start codon inhibits translation by physically obstructing access of the translation machinery to the start codon. In general, this results in a reduction in translation from the target start codon, and inhibition of the expression of the corresponding protein isoform. In some embodiments, the level of inhibition is about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more. In some embodiments, the level of inhibition is about, less than about, or more than about 2-fold, 5-fold, 10-fold, 100-fold, 1000-fold, 10000-fold, 100000-fold, 1000000-fold, or more. In some embodiments, the protein isoform translated from the target start codon is reduced below a minimum threshold of detection. In some embodiments, the level of translation initiation activity of one or more alternative start codons increases in the presence of an antisense oligonucleotide that hybridizes to a target start codon, such as an increase of about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more. In some embodiments, one or more alternative start codons are only utilized for translation initiation (e.g. detectable above a minimum threshold of detection) when one or more target start codons (e.g. the primary start codon) are blocked by hybridization to an antisense oligonucleotide provided herein. In some embodiments, the level of translation initiation activity of one or more alternative start codons is unaffected by hybridization of the antisense oligonucleotide with a target start codon. In some embodiments, the portion of the antisense oligonucleotide that is substantially complementary the start codon is located near the middle of the antisense oligonucleotide sequence, or the middle of the portion of the antisense oligonucleotide sequence that specifically hybridizes to a target polynucleotide (e.g. an mRNA).

In some embodiments, the antisense oligonucleotide specifically hybridizes to two or more target start codons, such as about or more than about 2, 3, 4, 5, 6, 7, 8, 9, 10, 15, 20, or more start codons, any or all of which may or may not be located in the same mRNA. Translation from each of the two or more target start codons may be inhibited to a different degree, such as about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more; or about, less than about, or more than about 2-fold, 5-fold, 10-fold, 100-fold, 1000-fold, 10000-fold, 100000-fold, 1000000-fold, or more. In some embodiments, the method comprises hybridizing two or more antisense oligonucleotides (e.g. 2, 3, 4, 5, 6, 7, 8, 9, 10, 15, 20, or more antisense oligonucleotides) to one or more start codons of one or more mRNA molecules (e.g. 2, 3, 4, 5, 6, 7, 8, 9, 10, 15, 20 mRNA molecules). For example, two or more antisense oligonucleotides may be designed to specifically hybridize to overlapping regions of a single mRNA, each of the regions comprising the same start codon, thereby increasing the level of translational inhibition of the corresponding isoform relative to the level of inhibition achieved by any of the two or more antisense oligonucleotides alone. As a further example, two or more antisense oligonucleotides may be designed to each specifically hybridize to different start codons of the same mRNA, thereby inhibiting translation of the corresponding isoforms. As a further example, two or more antisense oligonucleotides may be designed to each specifically hybridize to different start codons of different mRNA molecules (e.g. from different genes), thereby inhibiting translation of the corresponding isoforms. Also contemplated are combinations of these scenarios. Translational inhibition induced by each of the two or more antisense oligonucleotides may be different in degree, such as about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more; or about, less than about, or more than about 2-fold, 5-fold, 10-fold, 100-fold, 1000-fold, 10000-fold, 100000-fold, 1000000-fold, or more.

Methods for measuring protein levels are known in the art, and include, without limitation, indirect methods involving detection of binding of a protein-binding agent to a target protein (e.g. Western blot, ELISA, flow cytometry, and histological and other microscopic imaging techniques), and direct methods (e.g. measuring a feature or function of a target protein, such as an enzyme activity on a detectable substrate). Typically, detection involves the use of a label. Useful labels provided herein include fluorescent dyes (e.g., fluorescein, fluorescein isothiocyanate, Texas red, rhodamine, and the like), enzymes (e.g., LacZ, CAT, horseradish peroxidase, alkaline phosphatase, I$^2$-galactosidase, β-galactosidase, glucose oxidase, acetylcholinesterase and others, commonly used as detectable enzymes), quantum dot-labels, chromophore-labels, enzyme-labels, affinity ligand-labels, electromagnetic spin labels, heavy atom labels, probes labeled with nanoparticle light scattering labels or other nanoparticles, TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, hapten conjugates such as digoxigenin or dinitrophenyl, or members of a binding pair that are capable of forming complexes (e.g. streptavidin/biotin, avidin/biotin or an antigen/antibody complex including, for example, rabbit IgG and anti-rabbit IgG), other fluorophores (e.g. umbelliferone, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin), fluorescent lanthanide complexes such as Europium and Terbium, molecular beacons and fluorescent derivatives thereof, luminescent material such as luminal, light scattering or plasmon resonant materials such as gold or silver particles or quantum dots, radiolabels (e.g. $^{14}$C, $^{123}$I, $^{124}$I, $^{131}$I, $^{125}$I, Tc99m, $^{32}$P, $^{35}$S or $^3$H), spherical shells, and probes labeled with any other signal generating label known to those of skill in the art.

In some embodiments, the antisense oligonucleotide inhibits cell cycle progression. In general, inhibition of cell cycle progression is evidenced by an increase in the proportion of cells in one or more phases of the cell cycle in a population of cells treated with an antisense oligonucleotide relative to an untreated control population of cells. Methods evaluating effects on cell cycle progression are known in the art. For example, cell cycle status for a population of cells can be determined by flow cytometry using fluorescent dyes which stain the DNA content of cell nuclei. Flow cytometry yields quantitative information on the DNA content of cells and hence allows determination of the relative numbers of cells in, or the proportion of cells in the G1, S and G2+M phases of the cell cycle. Since the DNA content of cell nuclei varies through the cell cycle in a reasonably predictable fashion, i.e. cells in G2 or M have twice the DNA content of cells in G1, and cells undergoing DNA synthesis in S phase have an intermediate amount of DNA, it is possible to monitor the relative distribution of cells between different phases of the cell cycle. EP 798386 describes a method for the analysis of the cell cycle of cell sub-populations present in heterogeneous cell samples. This method uses sequential incubation of the sample with fluorescently labeled monoclonal antibodies to identify specific cell types and a fluorochrome that specifically binds to nucleic acids. Cell-cycle may also be determined by detecting the level of one or more proteins associated with one or more cell-cycle phases. For example, WO 03/031612 describes DNA reporter constructs and methods for determining the cell cycle position of living mammalian cells by means of cell cycle phase-specific expression control elements and destruction control elements.

In some embodiments, the antisense oligonucleotide enhances sensitivity of tumor cells to chemotherapy or radiation therapy. Sensitization can be measured by any method known in the art. In general, sensitization effects compare a population of cells treated with a chemotherapeutic agent or radiation therapy alone to a population of cells treated with a chemotherapeutic agent or radiation therapy in combination with the antisense oligonucleotide. Treated cell populations may be in vitro, such as cells in a dish, or in vivo, such as a tumor. In some embodiments, sensitization is evidenced by decreased tumor mass, increased tumor cell death, stabilization of tumor size for an increased period of time, increased survival time, increased time of remission, or any other suitable measure for the treatment of a proliferative disorder (e.g. cancer).

In one aspect, provided herein is a method of inhibiting an isoform associated with a disease. In some embodiments, the method comprises administering to a subject an antisense oligonucleotide of about 12 to 50, or about 12 to 40, nucleotides in length comprising a sequence substantially complementary to a translation start codon of an mRNA that encodes a cellular protein having at least two isoforms, wherein said antisense oligonucleotide inhibits translation of an isoform. In one aspect, provided herein is a method of inhibiting a protein associated with a disease. In some embodiments, the method comprises administering to a subject an antisense oligonucleotide of about 12 to 50, or about 12 to 40, nucleotides in length comprising a sequence substantially complementary to a translation start codon of an mRNA that encodes at least two cellular proteins translated from at least two translation start codons, wherein said antisense oligonucleotide inhibits translation of at least one of said at least two cellular proteins. The antisense oligonucleotides useful in the methods provided herein include any of the antisense oligonucleotides described herein. mRNA targets and the protein isoforms encoded thereby can be any of the mRNA targets and protein isoforms described herein. Typically, the isoform that is inhibited is associated with a disease, and inhibiting the isoform treats the disease.

A "subject," as used herein, includes any animal that exhibits a symptom, or is at risk for exhibiting a symptom, which can be treated with an antisense oligonucleotide compound provided herein. Suitable subjects include laboratory animals (such as mouse, rat, rabbit, and guinea pig), farm animals, domestic animals or pets (such as a cat or dog), non-human primates, and preferably humans. Tissues, cells and their progeny of a biological entity obtained in vivo or cultured in vitro are also encompassed. Likewise, a disease treated by the methods and compositions provided herein can be any disease associated with a protein isoform expressed from an mRNA encoding two or more isoforms, which disease can be treated by inhibiting translation of the associated protein isoform. In some embodiments, the disease is a proliferative disorder (e.g. cancer, whether metastatic or benign), Alzheimer's disease, TAR DNA-binding protein-43 (TBP-43) proteinopathies, diabetes, a neurodegenerative disorder, amytrophic lateral sclerosis, or leukemia. The therapeutic methods provided herein may be carried out on subjects displaying pathology resulting from a disease being treated, subjects suspected of displaying pathology resulting from a disease being treated, and subjects at risk of displaying pathology resulting from a disease being treated. For example, subjects that have a genetic predisposition to a disease can be treated prophylactically. Subjects exhibiting symptoms of a disease may be treated to decrease the symptoms or to slow down or prevent further progression of the symptoms. In some embodiments, treatment of disease stabilizes a measure of disease severity for at least about 1, 2, 3, 4, 5, 6, 7, 8, 9, 10, 11, 12, or more months; or at least about 1, 2, 3, 4, 5, 6, 7, 8, 9, 10, 15, 20, or more years, such that steady worsening by said measure is slowed or prevented. In some embodiments, treatment of a disease improves a measure of disease severity by 5%, 10%, 15%, 20%, 25%, 30%, 35%, 40%, 45%, 50%, 60%, 70%, 80%, 90%, 95%, 99%, 100%, or more.

In some embodiments, the method comprises administering to a subject two or more antisense oligonucleotides (e.g. 2, 3, 4, 5, 6, 7, 8, 9, 10, 15, 20, or more antisense oligonucleotides), with each of the two or more antisense oligonucleotides complementary to one or more start codons of one or more mRNA molecules (e.g. 2, 3, 4, 5, 6, 7, 8, 9, 10, 15, 20 mRNA molecules). For example, two or more antisense oligonucleotides may be designed to specifically hybridize to overlapping regions of a single mRNA, each of the regions comprising the same start codon, thereby increasing the level of translational inhibition of the corresponding isoform relative to the level of inhibition achieved by any of the two or more antisense oligonucleotides alone. As a further example, two or more antisense oligonucleotides may be designed to each specifically hybridize to different start codons of the same mRNA, thereby inhibiting translation of the corresponding isoforms. As a further example, two or more antisense oligonucleotides may be designed to each specifically hybridize to different start codons of different mRNA molecules (e.g. from different genes), thereby inhibiting translation of the corresponding isoforms. Also contemplated are combinations of these scenarios. Translational inhibition induced by each of the two or more antisense oligonucleotides may be different in degree, such as about, less than about, or more than about 5%, 10%, 15%, 20%, 25%, 30%, 35%, 40%, 45%, 50%, 55%, 60%, 65%, 70%, 75%, 80%, 85%, 90%, 95%, 99%, or more.

In some embodiments, provided herein are antisense oligonucleotides as described herein for the treatment of one or more diseases. These may include, without limitation, a proliferative disorder, an autoimmune disorder, an inflammatory disorders, and a neurodegenerative disorder.

In some embodiments, the disease treated by the methods and compositions provided herein is a proliferative disorder (e.g. cancer, whether benign or malignant). Examples of proliferative disorders include, but are not limited to, Acute monocytic leukemia, Acute myeloblastic leukemia with maturation, Acute myeloid dendritic cell leukemia, Acanthoma, Acinic cell carcinoma, Acoustic neuroma, Acral lentiginous melanoma, Acrospiroma, Acute eosinophilic leukemia, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Acute lymphoblastic leukemia, Acute megakaryoblastic leukemia, Acute myeloid leukemia, Acute promyelocytic leukemia, Adamantinoma, B-cell leukemia, B-cell lymphoma, Bellini duct carcinoma, Biliary tract cancer, Bladder cancer, Blastoma, Bone Cancer, Bone tumor, Brain Stem Glioma, Adenocarcinoma, Adenoid cystic carcinoma, Adenoma, Adenomatoid odontogenic tumor, Adrenocortical carcinoma, Angiomyolipoma, Angiosarcoma, Appendix cancer, Astrocytoma, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Atypical teratoid rhabdoid tumor, Basal cell carcinoma, Basal-like carcinoma, Brain Tumor, Breast Cancer, Brenner tumor, Bronchial Tumor, Bronchioloalveolar carcinoma, Brown tumor, Chronic myelogenous leukemia, Chronic Myeloproliferative Disorder, Chronic neutrophilic leukemia, Clear-cell tumor, Colon Cancer, Colorectal cancer, Burkitt's lymphoma, Cancer of Unknown Primary Site, Cerebral Astrocytoma, Cervical Cancer, Cholangiocarcinoma, Chondroma, Chondrosarcoma, Chordoma, Choriocarcinoma, Choroid plexus papilloma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Chronic Lymphocytic Leukemia, Chronic monocytic leukemia, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, and Wilms' tumor.

In some embodiments, treatment of the proliferative disorder is effected by administering one or more antisense oligonucleotides provided herein in the absence of other therapeutic agents. In some embodiments, administration of the antisense oligonucleotide is combined with additional therapeutic measures, such as administration of additional therapeutic agents (e.g. chemotherapeutics or radiation), surgical resection, or combinations of these. In some embodiments, the antisense oligonucleotide sensitizes affected cells (e.g. tumor cells) to treatment with one or more other therapeutic agents (e.g. chemotherapeutics or radiation), such that the effect of the one or more other therapeutic agents is greater than the effect observed or expected in the absence of administration of the antisense oligonucleotide. Generally, efficacy in the treatment of a proliferative disorder may be measured by the degree to which the methods and compositions provided herein promote inhibition of tumor cell proliferation, the inhibition of tumor vascularization, the eradication of tumor cells, a reduction in the size of at least one tumor, and/or any other suitable measure known in the art for the effective treatment of a proliferative disorder. Progress of the inventive method in treating a proliferative disorder (e.g., reducing tumor size or eradicating cancerous cells) can be ascertained using any suitable method, such as those methods currently used in the clinic to track tumor size and cancer progress. A typical efficacy parameter used to evaluate the treatment of a proliferative disorder is a reduction in the size of a tumor. Tumor size can be determined using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue. In some embodiments, the antisense oligonucleotide inhibits cell cycle progression, as described herein.

Desirably, the growth of a tumor treated with antisense oligonucleotides provided herein, alone or in combination with other treatments, is stabilized (i.e., one or more tumors do not increase by more than about 5%, 10%, or 15% in size, and/or do not metastasize). Preferably, administering one or more antisense oligonucleotides provided herein, alone or in combination with other treatments, reduces the size of a tumor at least about 5% (e.g., at least about 10%, 15%, 20%, 25%, 30%, 35%, 40%, 45%, 50%, 55%, 60%, 65%, 70%, 75%, 80%, 85%, 90%, 95%, or more). In some embodiments, treatment of a proliferative disease comprises elimination of the affected tissue (e.g. a tumor), or reduction to below a level of detection. In some embodiments, a subject having a proliferative disorder treated with one or more antisense oligonucleotide provided herein remains tumor-free (e.g. in remission) for at least about 1, 2, 3, 4, 5, 6, 7, 8, 9, 10, 11, 12, or more months following treatment. In some embodiments, a subject having a proliferative disorder treated with one or more antisense oligonucleotide provided herein remains tumor-free for at least about 1, 2, 3, 4, 5, 6, 7, 8, 9, 10, or more years following treatment. When a tumor is subject to surgical resection following completion of an administration regimen including administration of one or more antisense oligonucleotides provided herein, efficacy in reducing tumor size can be determined by measuring the percentage of resected tissue that is necrotic (i.e., dead). In this regard, a cancer is treated if the necrosis percentage of the resected tissue is greater than about 20% (e.g., at least about 30%, 40%, 50%, 60%, 70%, 80%, 90%, or 100%). Examples of additional therapeutic agents for the treatment of proliferative disorders are known in the art, and include without limitation, mitotic inhibitors, alkylating agents, antimetabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, anti-androgens, and radioactive isotopes.

In some embodiments, the disease treated by the methods and compositions provided herein is a neurodegenerative disorder. Neurodegenerative disorders include any disorder comprising degeneration of neuronal cells (e.g. cells of the central and/or peripheral nervous system). Examples of neurodegenerative disorders include, but are not limited to, polyglutamine expansion disorders (e.g., Huntington's disease, dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer disease, amyotrophic lateral sclerosis, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Parkinson's disease, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, Tabes dorsalis, and prion diseases (including Creutzfeldt-Jakob, Gerstmann-Sträussler-Scheinker disease, Kuru and fatal familial insomnia).

In general, treatment of a neurodegenerative disorder may comprise slowing, stopping, or reversing disease progression, such as may be measured with respect to a sign or symptom of the neurodegenerative disorder, and/or increasing survival time. In some embodiments, a neurodegenerative disorder may be treated prophylactically so as to delay or prevent the onset of the neurodegenerative disorder in a subject at risk for developing the disease. In some embodiments, the disease treated by the methods and compositions provided herein is Amyotrophic lateral sclerosis (ALS), survival motor neuron (SMN), or spinal muscle atrophy (SMA). Examples of signs or symptoms of a neurodegenerative disorder that may be assessed include, but are not limited to, enhancement of microglial activity; infiltration and/or accumulation of microglia in the brain; accumulation of substances activated upon inflammation, e.g., complements, in the brain; accumulation and/or deposition of amyloid β in brain tissues (especially in Alzheimer's disease); impairment of learning; mild to severe dementia; progressive impairment of memory (ranging from mild forgetfulness to disorientation and severe memory loss); poor visio-spatial skills; personality changes; poor impulse control; poor judgment; distrust of others; increased stubbornness; restlessness; poor planning ability; poor decision making; social withdrawal; extracellular neuritic β-amyloid plaques (especially in Alzheimer's disease); neurofibrillary tangles; neurofibrillary degeneration; granulovascular neuronal degeneration; synaptic loss; neuronal cell death; and decreased motor control (including tics and complete loss of motor control over one or more muscles or muscle groups). In some embodiments, a therapeutically effective amount one or more antisense oligonucleotides, alone or in combination with other therapeutic agents, comprises an amount of a therapeutic agent that decreases one or more symptoms of the neurodegenerative disorder, increases the time to progression of one or more symptoms of the neurodegenerative disorder, or increases survival time by at least about 10%, 20%, 30%, 40%, 50%, 60%, 70%, 80%, 90%, 95%, 100%, or more as compared to that which would have occurred without the one or more antisense oligonucleotides provided herein, or with respect to a corresponding measure or projection prior to such treatment. Changes in a pathology associated with a neurodegenerative disorder can be measured in tissue samples from subjects by comparing one or more samples acquired before treatment to one or more samples after treatment. In some embodiments, administration of one or more antisense oligonucleotides stabilizes a pathological characteristic of a neurodegenerative disorder, or decreases a pathological characteristic thereof by 10%, 20%, 30%, 40%, 50%, 60%, 70%, 80%, 90%, 95%, or more.

In some embodiments, the neurodegenerative disorder is Alzheimer's disease (AD). Cognitive behavior in AD (e.g., mentation, memory) may be measured by any one of several tests (See Gershon et al., Clinical Evaluation of Psychotropic Drugs: Principles and Guidelines, Prien and Robinson (eds.), Raven Press, Ltd., New York, 1994, p. 467). One such test, BCRS, is designed to measure only cognitive functions: concentration, recent memory, past memory, orientation, functioning, and self-care. This test, as well as the Weschler Memory Scale and the Alzheimer's Disease-Associated Scale, may be used to determine improvement following therapeutic treatment. An increase in mentation or a reduction in memory loss is present if there is a statistically significant difference in the direction of normality in the Weschler Memory Scale test. For example, test results of the performance of treated patients are compared to members of a placebo group or between subsequent tests given to the same patient.

A frequently used instrument to evaluate cognitive impairment is the Mini-Mental State Examination (MMSE) (see Cockrell, J. R., et al., Psychopharmacology 1988; 24:689-692, Crumb, R. M., et al., JAMA 1993; 269:2386-2391). The MMSE includes measures of memory, orientation to place and time, naming, reading, copying (visuospatial organization), writing, and the ability to follow a three-stage command. A score of less than 24 points on the MMSE is generally accepted as signifying cognitive impairment. Other measures of AD severity include the Blessed Orientation Memory Concentration instrument, the Short Test of Mental Status, and the Functional Activities Questionnaire. The Blessed Information Memory Concentration instrument (Blessed, G., et al., Br. J. Psychiatry 1968; 114:797-811) primarily evaluates orientation, memory, and concentration. The Blessed Orientation Memory Concentration instrument (Katzman, R., et al., Am. J. Psychiatry 1983; 140:734-739) assesses orientation to time, recall of a short phrase, the ability to count backward, and the ability to recite months in reverse order. The Short Test of Mental Status (Kokmen, E., et al., Mayo Clin. Proc., 1987; 62(4):281-289) evaluates orientation, attention, recall, concentration, abstraction, clock drawing, and copying. The Functional Activities Questionnaire (Pfeffer, R. I., et al., J. Gerontol. 1982; 37:323-329) employs responses from a family member or a friend of the subject to evaluate functional activities that may be impaired by dementia.

In certain embodiments, the disease is an autoimmune disease. In more specific embodiments, the autoimmune disease is selected from, but not limited to, Type 1 diabetes, rheumatoid arthritis, multiple sclerosis, systemic lupus erythematosus, myasthenia gravis, Crohn's disease, Graves' diseae, thrombocytopenic purpura and pemphigus.

In certain embodiments, the disease is an inflammatory disease. In more specific embodiments, the inflammatory disease is selected from, but not limited to, Alzheimer's, ankylosing spondylitis. arthritis (osteoarthritis, rheumatoid arthritis (RA), soriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Parkinson's disease, and ulcerative colitis.

A. Illustrative Embodiments Relating to p53

In another aspect, the present invention relates to methods of using the p53-targeted antisense oligonucleotides described herein for treating a cell, tissue or subject, typically to reduce expression of one or more p53 isoforms and/or mutants in a therapeutically beneficial manner. The cells or tissue that may be modulated by the present invention are preferably mammalian cells, or more preferably human cells. Such cells can be of a healthy state or of a diseased state, such as a cancerous state. The cells can be in vitro, or in a mammalian subject such as a human in vivo. In certain aspects, the cell is a cancerous cell, where its predominant response to drug or DNA-damaged induced activation of p53 is survival relative to cell death, the latter being measured, for example, by apoptosis. The cancer cell may be refractory or resistant to a chemotherapeutic or other cancer-related treatment in a 53-associated manner. The cancer cell may express wild-type or canonical p53 and/or a mutant p53, for example, where the mutant p53 is associated with increased cell proliferation or other cancerous phenotype.

Certain embodiments therefore relate generally to methods for reducing expression of full-length p53 or an isoform or mutant or thereof, comprising contacting a cell with one or more antisense oligonucleotides described herein, thereby reducing expression of full-length p53 or the isoform or mutant thereof. These and related methods can be used to reduce expression of any one or more of the p53 isoforms, mutants, or polymorphic forms of p53 described herein and known in the art. Specific exemplary p53 isoforms include wild-type or canonical p53, ΔN-p53, p53β and/or p53γ isoforms.

Related but more specific embodiments include methods of reducing expression of full-length p53 and at least one ΔN-p53 isoform thereof in a cell, comprising contacting the cell with at least two nuclease-resistant antisense oligonucleotides described herein, preferably where the first antisense oligonucleotide is complementary to at least 12 bases of SEQ ID NO:1 (i.e., the region surrounding the AUG codon encoding for residue 1 of full-length p53), and where the second oligonucleotide is complementary to at least 12 bases of SEQ ID NO:2 (i.e., the region surrounding the AUG codon encoding for residue 40 of full-length p53), thereby reducing expression of full-length p53 and the ΔN-p53 isoform thereof. These and related embodiments can also be used to reduce expression of other p53 isoforms, such as p53β and/or p53γ isoforms, among others described herein and known in the art.

In certain aspects, for example, these and related methods can be applied to treating cancer in clinical settings where mutant p53 expression is associated with increased cell proliferation, migration, invasion and metastasis through the suppression of p63 (see, e.g., Adorno et al., 2009) or other mechanism(s), and where targeting mutant p53 in highly aggressive human tumours has therapeutic potential. As discussed below, these and related embodiments can also be combined with methods of treating or reducing cancer, by concurrently or sequentially contacting the cell with a chemotherapeutic or other cancer treatment, to increase sensitivity of the cell to the chemotherapeutic or other cancer treatment. These latter embodiments are typically employed where the cell is refractory to cancer treatment in a p53-associated manner.

Accordingly, also included are methods of increasing sensitivity of a cell to a chemotherapeutic or other cancer treatment, such as radiation treatment, where the cell expresses full-length or mutant p53 or both, and where a predominant response of the cell to p53 expression (e.g. wild-type or mutant), or p53 activation by the chemotherapeutic agent or other cancer treatment, is survival relative to cell-death, comprising contacting the cell with the chemotherapeutic or other cancer treatment (e.g., exposing the cell to radiation) and one or more antisense oligonucleotide described herein, where the antisense oligonucleotide(s) reduce expression of full-length and/or mutant p53, thereby increasing sensitivity of the cell to the chemotherapeutic. As shown in the accompanying Examples, these embodiments relate to the discovery that in certain settings, for example, where the predominant tumour response to drug-induced p53 activation is survival rather than death, the repression of p53 increases sensitivity to chemotherapeutic drugs, such as doxorubicin. Given also the observation that p53 can be resilient to efforts to block its expression, and the possibility of p53 isoforms having unanticipated activities, specific embodiments relate to contacting the cell with a combination of two or more antisense oligonucleotides, each comprising a different p53 targeting sequence (e.g., M1, M40), which preferably reduces expression of wild-type or mutant 53 along with one or more non-canonical p53 isoforms, such as ΔN-p53, p53β and/or p53γ isoforms.

The p53-targeted antisense oligonucleotides described herein can be used to sensitize cancer cells to a variety of chemotherapeutic agents and other cancer-related therapies. Examples of such non-chemotherapeutic, cancer-related therapies include irradiation and hormone-related therapies. Therapies in this latter category include the use of sex hormones, or hormone-like drugs, which alter the action or production of female or male hormones. These drugs can be used to slow the growth of breast, prostate, and endometrial (uterine) cancers, among others, which normally grow in response to natural hormones in the body. Therapeutic hormones do not typically act like standard chemotherapy drugs, but rather act by preventing the cancer cell from using the hormone it needs to grow, or by preventing the body from making the hormones. Applying the antisense methods provided herein to hormone-based therapies can be especially useful where p53 expression or activation plays a role in counteracting the ability of the hormone treatment to reduce tumor growth or metastasis. p53 antisense and hormone therapies can also be used in combination with chemotherapeutic agents. Examples of hormone drugs include the anti-estrogens such as fulvestrant (Faslodex®), tamoxifen, and toremifene (Fareston®); aromatase inhibitors such as anastrozole (Arimidex®), exemestane (Aromasin®), and letrozole (Femara®); progestins such as megestrol acetate (Megace®); estrogens; anti-androgens such as bicalutamide (Casodex®), flutamide (Eulexin®), and nilutamde (Nilandron®); and gonadotropin-releasing hormone (GnRH), also known as luteinizing hormone-releasing hormone (LHRH) agonists or analogs such as leuprolide (Lupron®) and goserelin (Zoladex®).

Preferred embodiments include the use of antisense oligonucleotides in combination with chemotherapeutics. Examples of general classes of chemotherapeutic agents that can be used according to the methods and compositions provided herein include, without limitation, DNA intercalating agents, topoisomerase inhibitors (I or II), alkylating agents, anti-metabolites, mitotic inhibitors, and chemotherapeutics having a combination of any of these activities. Also included are pharmaceutical salts and formulations of any of these chemotherapeutic agents.

In particular embodiments, the chemotherapeutic is an anthracycline antibiotic or an analog thereof. Anthracycline antibiotics can be generally classified as DNA intercalating agents, topoisomerase II inhibitors, and/or anti-tumor antibiotics. Other anti-tumor antibiotics include the drugs actinomycin-D, bleomycin, and mitomycin-C. Examples of anthracyclines or analogs include daunorubicin (Daunomycin), doxorubicin (Adriamycin), epirubicin, idarubicin, valrubicin, or mitoxantrone (an analog), or a pharmaceutical salt or formulation thereof. Specific embodiments include doxorubicin, as shown in the accompanying Examples, and pharmaceutical salts such as a hydrochloride salt of doxorubicin. Also included are PEGylated forms of doxorubicin (e.g., Doxil), and liposomal formulations of doxorubicin (e.g., Myocet).

Topoisomerase inhibitors I and II interfere with enzymes called topoisomerases, which otherwise act to separate the strands of DNA during replication. Topoisomerase inhibitors are typically used to treat certain leukemias, in addition to lung, ovarian, gastrointestinal, and other cancers. Examples of topoisomerase I inhibitors include topotecan and irinotecan (CPT-11). In addition to certan anthracyclines, examples of topoisomerase II inhibitors include etoposide (VP-16) and teniposide. As noted above, mitoxantrone also inhibits topoisomerase II Alkylating agents directly damage DNA and thereby prevent cancers cell from replicating. As a class of drugs, these agents are not phase-specific; in other words, they typically work in all phases of the cell cycle. Alkylating agents are used to treat a variety of cancers, including acute and chronic leukemia, lymphoma, Hodgkin's disease, multiple myeloma, sarcoma, in addition to cancers of the lung, breast, and ovary. There are many different alkylating agents, including, for example, nitrogen mustards such as mechlorethamine (nitrogen mustard), chlorambucil, cyclophosphamide (Cytoxan®), ifosfamide, and melphalan; nitrosourea such as streptozocin, carmustine (BCNU), and lomustine; alkyl sulfonates such as busulfan; triazines such as dacarbazine (DTIC) and temozolomide (Temodar®); and ethylenimines such as thiotepa and altretamine (hexamethylmelamine). The platinum drugs (cisplatin, carboplatin, and oxalaplatin) are sometimes grouped with alkylating agents because they kill cells in a related way.

Antimetabolites are a class of drugs that interfere with DNA and RNA growth by substituting for the normal building blocks of RNA and DNA, and thus typically damage cells during S phase. Antimetabolites are commonly used to treat leukemias, tumors of the breast, ovary, and the intestinal tract, among other cancers. Non-limiting examples of antimetabolites include 5-fluorouracil (5-FU), capecitabine (Xeloda®), 6-mercaptopurine (6-MP), methotrexate, gemcitabine (Gemzar®), cytarabine (Ara-C®), fludarabine, and pemetrexed (Alimta®).

Mitotic inhibitors include plant alkaloids and other compounds derived from natural products. These chemothereutics interfere with mitosis or inhibit enzymes from making proteins needed for cell reproduction. Even though they work mainly during the M phase of the cell cycle, they are capable of damaging cells in all phases. Mitotic agents are used to treat many different types of cancer including breast, lung, myelomas, lymphomas, and leukemias. These drugs are also known for their potential to cause peripheral nerve damage, which can be a dose-limiting side effect. Examples of mitotic inhibitors include, without limitation, taxanes such as paclitaxel (Taxol®) and docetaxel (Taxotere®); epothilones such as ixabepilone (Ixempra®); vinca alkaloids such as vinblastine (Velban®), vincristine (Oncovin®), and vinorelbine (Navelbine®); and estramustine (Emcyt®).

Accordingly, certain methods provided herein relate to combination therapies, which utilize of one or more p53-targeted antisense oligonucleotides in combination with one or more chemotherapeutics and/or other cancer-related therapies, such as irradiation and hormone-related therapies, for treating or reducing cancer in a subject. The antisense agents and chemotherapeutics can be administered to the subject concurrently or sequentially. For example, the antisense oligonucleotide(s) can be administered prior to, at the same time as, or after administering the chemotherapeutics or applying another cancer-related therapy, or vice versa. For concurrent administration, certain embodiments include compositions that comprise a combination of one or more p-53 targeted antisense oligonucleotide(s), e.g., M1 and M40, and at least one chemotherapeutic, hormone or related agent, or both, for treating or reducing cancer.

As noted above, embodiments of the present invention relate generally to reducing p53-expression in a cell, preferably a cancer cell, and also to methods of sensitizing cancer cells to a chemotherapeutic or other cancer-related therapy. Typically, the cancer cell is characterized by having a survival-oriented response to p53 expression (e.g., mutant p53 expression) and/or p53 activation by a chemotherapeutic or other drug or therapy, such as DNA damage-inducing agent/treatment or hormone therapy. Such cancer cells can be identified according to routine knowledge or techniques in the art (see, e.g., (Kim et al., 2009; Vousden and Prives, 2009, which show that p53 can promote the repair and survival of damaged cells through a variety of mechanisms). For instance, it can be shown that the predominant response of a cell to p53 expression or p53 activation (by a chemotherapeutic or other therapy) is survival relative to cell-death where a "statistically significant" number of cells in a population survive in response to contacting that population with chemotherapeutic, or exposing it to radiation, compared to those that die, for example, by apoptosis, typically where p53 activation or expression also increases in the surviving cells, relative to untreated cells. A "statistically significant" number of cells includes where greater than about 10, 20, 30, 40, 50, 60, 70, 80, 90 or 100% of the cells survive in response to being contacted with the chemotherapeutic or exposed to radiation and optionally show increased p53 activation or expression. The population of cells can be in vitro, where such measurements can be made on a per cell basis, or in vivo, where such measurements can be made, for example, by measuring the size or presence of a tumor or the degree of its metastasis in response to therapy. These methods are merely exemplary, and other methods or knowledge can be used to identify an appropriate cancer cell type for treatment according to the methods provided herein.

Certain embodiments relate to methods of treating or reducing cancers, including human cancers, and diseases associated with increased cell survival. Non-limiting examples of general types of cancers include prostate cancer, breast cancer, colon cancer, rectal cancer, lung cancer, ovarian cancer, testicular cancer, stomach cancer, bladder cancer, pancreatic cancer, liver cancer, kidney cancer, brain cancer, hematologic cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma.

Illustrative diseases associated with increased cell survival, or the inhibition of apoptosis include, but are not limited to, cancers (such as follicular lymphomas, carcinomas, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Graves' disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection.

Further illustrative diseases or conditions associated with increased cell survival include, but are not limited to, progression and/or metastases of malignancies and related disorders such as leukemia (including acute leukemias (for example, acute lymphocytic leukemia, acute myelocytic leukemia, including myeloblastic, promyelocytic, myelomonocytic, monocytic, and erythroleukemia)) and chronic leukemias (for example, chronic myelocytic (granulocytic) leukemia and chronic lymphocytic leukemia), myelodysplastic syndrome polycythemia vera, lymphomas (for example, Hodgkin's disease and non-Hodgkin's disease), multiple myeloma, Waldenstrom's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Particular embodiments include where the cancer cell is in a human subject and is associated with one or more of breast cancer, axillary lymph node involvement following resection of primary breast cancer, ovarian cancer, bladder cancer such as transitional cell bladder cancer, lung cancer, thyroid cancer, gastric cancer, soft tissue or osteogenic sarcoma, neuroblastoma, Wilms' tumor, malignant lymphoma (Hodgkin's or non-Hodgkin's), acute myeloid leukemia such as acute myeloblastic leukemia, acute lymphoblastic leukemia, Kaposi's sarcoma related to acquired immunodeficiency syndrome (AIDS), Ewing's tumor, squamous cell carcinoma of the head, neck, cervix, or vagina, carcinoma of the testes, prostate, or uterus, or refractory multiple myeloma. These cancers can often be treated by administration of doxorubicin. Accordingly, preferred embodiments relate to methods of administering to a human subject one or more antisense oligonucleotides described herein, in combination with doxorubicin or a pharmaceutical salt of formulation thereof. Specific embodiments include the administration of two antisense oligonucleotides, one targeted to SEQ ID NO:1 (e.g., M1) and the other targeted to SEQ ID NO:2 (e.g., M2), in combination with doxorubicin.

An effective in vivo treatment regimen using the antisense oligonucleotides, compositions, and methods of the invention may vary according to the duration, dose, frequency and route of administration, as well as the condition of the subject under treatment (i.e., prophylactic administration versus administration in response to an existing condition). Accordingly, such in vivo therapy will often require monitoring by tests appropriate to the particular type of cancer under treatment, and corresponding adjustments in the dose or treatment regimen, in order to achieve an optimal therapeutic outcome.

6. Pharmaceutical Formulations

In certain embodiments, the present invention provides formulations or compositions suitable for the therapeutic delivery of antisense oligomers, as described herein. Hence, in certain embodiments, the present invention provides pharmaceutically acceptable compositions that comprise a therapeutically-effective amount of one or more of the oligomers or agents described herein, formulated together with one or more pharmaceutically acceptable carriers (additives) and/or diluents. While it is possible for an oligomer of the present invention to be administered alone, it is preferable to administer the compound as a pharmaceutical formulation (composition).

Methods for the delivery of nucleic acid molecules are described, for example, in Akhtar et al., 1992, *Trends Cell Bio.*, 2:139; and *Delivery Strategies for Antisense Oligonucleotide Therapeutics*, ed. Akhtar; Sullivan et al., PCT WO 94/02595. These and other protocols can be utilized for the delivery of virtually any nucleic acid molecule, including the isolated oligomers of the present invention.

As detailed below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, *Cell Transplant*, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941-949, 1999).

The invention also features the use of the composition comprising surface-modified liposomes containing poly (ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present invention includes oligomer compositions prepared for delivery as described in U.S. Pat. Nos. 6,692,911, 7,163,695 and 7,070,807. In this regard, in one embodiment, the present invention provides an oligomer of the present invention in a composition comprising copolymers of lysine and histidine (HK) as described in U.S. Pat. Nos. 7,163,695, 7,070,807, and 6,692, 911 either alone or in combination with PEG (e.g., branched or unbranched PEG or a mixture of both), in combination with PEG and a targeting moiety or any of the foregoing in combination with a crosslinking agent. In certain embodiments, the present invention provides antisense oligomers in compositions comprising gluconic-acid-modified polyhistidine or gluconylated-polyhistidine/transferrin-polylysine. One skilled in the art will also recognize that amino acids with properties similar to His and Lys may be substituted within the composition.

Certain embodiments of the oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject oligomers include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the oligomers of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from cyclodextrins, celluloses, liposomes, micelle forming agents, e.g., bile acids, and polymeric carriers, e.g., polyesters and polyanhydrides; and an oligomer of the present invention. In certain embodiments, an aforementioned formulation renders orally bioavailable an oligomer of the present invention.

Methods of preparing these formulations or compositions include the step of bringing into association an oligomer of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An oligomer of the present invention may also be administered as a bolus, electuary or paste.

In solid dosage forms of the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of the present invention to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also prepared by entrapping the drug in liposomes or microemulsions that are compatible with body tissues.

When the oligomers of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

As noted above, the formulations or preparations of the present invention may be given orally, parenterally, topically, or rectally. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers of the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of the present invention employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to treat the desired condition.

Antisense molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., *Drug Development and Industrial Pharmacy*, 17(12), 1685-1713, 1991 and REV 5901 (Sheen, P. C., et al., *J Pharm Sci* 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β. or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

One aspect of the present invention relates to formulations comprising liposomes containing an oligomer of the present invention, where the liposome membrane is formulated to provide a liposome with increased carrying capacity. Alternatively or in addition, the compound of the present invention may be contained within, or adsorbed onto, the liposome bilayer of the liposome. An oligomer of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993. For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT® and Lipofectamine® may be utilized to introduce polynucleotides or proteins into cells.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An oligomer may be formulated to be contained within, or, adapted to release by a surgical or medical device or implant. In certain aspects, an implant may be coated or otherwise treated with an oligomer. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of inflammation.

In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal, pulmonary and topical delivery. The appropriate route may be determined by one of skill in the art, as appropriate to the condition of the subject under treatment. For example, an appropriate route for delivery of an antisense oligomer in the treatment of a condition of the skin may include topical delivery, while delivery of a antisense oligomer for the treatment of a respiratory condition (e.g., COPD) may include inhalation, intranasal or pulmonary delivery. The oligomer may also be delivered directly to the site of inflammation infection, or to the bloodstream.

The antisense oligomer may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, as noted above, liposomes may be employed to facilitate uptake of the antisense oligonucleotide into cells. (See, e.g., Williams, S. A., Leukemia 10(12): 1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286 or PCT Application No US1992/005305. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In certain embodiments, the antisense compounds may be administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 1 mg to 500 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

SEQUENCE LISTING TABLE

| NAME | SEQUENCE | SEQ ID NO: |
|---|---|---|
| Region Surrounding AUG Start Codon | CUGCCUUCCGGGUCACUGCCAUGGAGGAGCCGCAGUCAGAUCCUAGCGUCGAG | 1 |
| Region Surrounding Met40 AUG Codon | CCCCCUUGCCGUCCCAAGCAAUGGAUGAUUUGAUGCUGUCCCCGGACGAUAUU | 2 |
| M1 | GCGGCTCCTCCATGGCAGTGAC | 3 |
| M40 | CATCAAATCATCCATTGCTTGG | 4 |
| E2SD | AGTTTCCATAGGTCTGAAAA | 5 |
| E4SA | GIIIACTGTAGATGIGTGAA | 6 |
| E6SA | CGGATAAGATGCTGAGGAGG | 7 |
| E7SA | GTTGTAGTGGATGGTGGTA | 8 |
| E7SD | CTGGAGTCTTCCAGTGTGAT | 9 |
| E9SD | AAGIGTGAAATATTCTCCATC | 10 |
| E10SA | GCGCTCACGCCCACGGATC | 11 |
| E10 | CCCTGCTCCCCCCTGGCTCC | 12 |
| Control | TGCCATCAACATATCTTGATCG | 13 |
| rTAT | RRRQRRKKR | 14 |
| Tat | RKKRRQRRR | 15 |
| $R_9F_2$ | RRRRRRRRRFF | 16 |
| $R_5F_2R_4$ | RRRRRFFRRRR | 17 |
| $R_4$ | RRRR | 18 |
| $R_5$ | RRRRR | 19 |
| $R_6$ | RRRRRR | 20 |
| $R_7$ | RRRRRRR | 21 |
| $R_8$ | RRRRRRRR | 22 |
| $R_9$ | RRRRRRRRR | 23 |
| $(RX)_8$ | RXRXRXRXRXRXRXRX | 24 |
| $(RAhxR)_4$; (P007) | RAhxRRAhxRRAhxRRAhxR | 25 |
| $(RAhxR)_5$; (CP04057) | RAhxRRAhxRRAhxRRAhxRRAhxR | 26 |
| $(RAhxRRBR)_2$; (CP06062) | RAhxRRBRRAhxRRBR | 27 |
| $(RAR)_4F_2$ | RARRARRARRARFFC | 28 |
| $(RGR)_4F_2$ | RGRRGRRGRRGRFFC | 29 |
| IDE M1 | TGGCTAAUGC | 30 |
| TDP-43 M85 | AAGGAAAAUGGAUGAGACAGA | 31 |
| RGS2 M16 | CGACUGCAGACCCAUGACAAGA | 32 |

EXAMPLES

Experimental Procedures

Cell Culture.

The human colon carcinoma cell lines HCT116 and HCT116 p53−/− were provided by Dr. B. Vogelstein (Sidney Kimmel Comprehensive Cancer Center, Baltimore Md.) and were cultured in McCoy's 5a Medium; the human lung cancer cell line H460 was cultured in RPMI 1640 medium; the human breast cancer cell line MDA-MB-468 was cultured in DMEM (high glucose) medium; the human breast cancer cell line MCF7 and the human leukemia cell lines OCI/AML3 and OCI/AML4 were cultured in α-MEM. All media were supplemented with 10% fetal bovine serum (FBS, Hyclone) and antibiotics. The medium for OCI/AML4 cells was supplemented with 10% conditioned medium from the bladder carcinoma cell line 5637 (Wang et al., 1989). All cells were cultured at 37° C. in a 5% $CO_2$ incubator.

PMO Design and Treatment.

PMOs were synthesized by methods previously described (see Summerton and Weller, 1997). The cell penetrating (CP) peptides $(RXR)_4XB$ (SEQ ID NO: 37) and $(RXRRBR)_2XB$ (SEQ ID NO: 38) (where R=arginine, X=6-aminohexanoic acid and B=β-alanine) were covalently conjugated to the 3'-end of each PMO and $(RX)_8B$ (SEQ ID NO: 39) was covalently conjugated to the 5'-end of each PMO through a non-cleavable piperazine linker by methods previously described (Wu et al., 2007). Lyophilized PMOs and CP-PMOs were dissolved in sterile water to a concentration of 2 mM and stored in the dark at 4° C. Immediately before use, the PMOs were diluted to 0.2 mM in sterile water. Cells were seeded in 10-cm dishes and treated with PMOs for 2 hours in 3 ml of RPMI 1640 medium lacking antibiotics and FBS. At the end of this period, the medium was removed, the cells were washed with RPMI 1640 medium, and the cells were placed in fresh growth medium containing antibiotics and FBS. The cells were then exposed to drug or γ-irradiated as described in the text.

Flow Cytometry for Cell Cycle Analysis and Apoptosis.

Cells were fixed on ice in cold 70% ethanol, washed twice with PBS containing 1% BSA, incubated with 100 µg/ml RNase A for 30 min at 37° C., and resuspended in PBS containing 50 µg/ml propidium iodide. Cell cycle distribution was examined by flow cytometry using a FACScalibur flow cytometer (Becton Dickinson). Apoptosis was assessed by flow cytometry using sub-G1 DNA content and by caspase activity using a cell membrane-permeable fluorogenic caspase 3 substrate in non-fixed cells as described by the manufacturer (Biotium, Inc., #30029).

Western Blot Analysis.

Cells in 10-cm dishes were washed once with PBS (minus calcium and magnesium) and lysed in 1% NP40 Lysis Buffer (50 mM Tris pH 8.0, 5 mM EDTA, 150 mM NaCl, 1% NP40 and protease inhibitors). Total protein (40 µg), in the presence of 0.1% bromophenol blue was loaded onto a 12% polyacrylamide gel containing SDS, subjected to electrophoresis and transferred onto a PVDF membrane.

Membranes were blocked in TBST (TBS with 0.05% Tween-20) containing 5% skim milk for 1 hour before incubation with primary antibodies in TBST containing 5% milk for 1 hour at room temperature. Membranes were then washed twice for 10 min in TBST before incubation with secondary antibodies in TBST containing 1% skim milk for 1 hour. The following antibodies to p53 were used: DO-1 (Santa Cruz), FL393 (Santa Cruz), PAb1801 (Banks et al., 1986) and PAb421 (Harlow et al., 1981). Antibodies to p21 and Mdm2 were obtained from Santa Cruz and to β-actin from Sigma. Anti-rabbit and anti-mouse secondary antibodies were conjugated with HRP and blots were visualized using enhanced chemiluminescence (Perkin Elmer).

Example 1

PMOs Block p53 Expression and Generate p53 Isoforms

To investigate the effectiveness of PMOs in blocking p53 expression, wild-type p53 expressing breast cancer MCF7 cells were treated with PMOs and peptide-conjugated PMOs targeting the translation initiation site of p53 mRNA (M1), the splice acceptor site of exon 10 (E10SA) and the coding region within exon 10 (E10) (see Table A below for PMOs used in all experiments described herein).

TABLE A p53 Targeting Sequences

| PMO | p53 Region | Targeting Sequence 5'-3' | SEQ ID NO: |
|---|---|---|---|
| M1 | AUG start codon | GCGGCTCCTCCATGGCAGTGAC | 3 |
| M40 | Met 40 AUG codon | CATCAAATCATCCATTGCTTGG | 4 |
| E2SD | Exon 2 | AGTTTCCATAGGTCTGAAAA | 5 |
| E4SA | Intron 3/ Exon 4 | GIIIACTGTAGATGIGTGAA | 6 |

TABLE A-continued p53 Targeting Sequences

| PMO | p53 Region | Targeting Sequence 5'-3' | SEQ ID NO: |
|---|---|---|---|
| E6SA | Exon 6 | CGGATAAGATGCTGAGGAGG | 7 |
| E7SA | Exon 7 | GTTGTAGTGGATGGTGGTA | 8 |
| E7SD | Exon 7 | CTGGAGTCTTCCAGTGTGAT | 9 |
| E9SD | Exon 9 | AAGIGTGAAATATTCTCCATC | 10 |
| E10SA | Intron 9/ Exon 10 | GCGCTCACGCCCACGGATC | 11 |
| E10 | Exon 10 (Internal) | CCCTGCTCCCCCCTGGCTCC | 12 |
| Control | Scrambled Control | TGCCATCAACATATCTTGATCG | 13 |

SD, slice donor
SA, splice acceptor
I, inosine residue

The peptide used was (RX)$_8$B where R=arginine, X=6-aminohexanoic acid, and B=β alanine. No overt indications of cellular toxicity were observed during the duration of the experiments at the concentrations of PMOs tested. A rabbit polyclonal antibody (FL393) was used to evaluate p53 expression by Western immune-blotting (FIG. 1). As shown in FIG. 1, E10SA interfered with the expression of p53 and produced a smaller stable polypeptide of approximately 48 kDa (p48); an even smaller polypeptide was observed at higher doses of E10SA. M1 interfered with p53 expression and produced a stable polypeptide of approximately 44 kDa (p44). E10 targets neither translation initiation nor splicing sites and had no effect on p53 expression.

Figure 8:
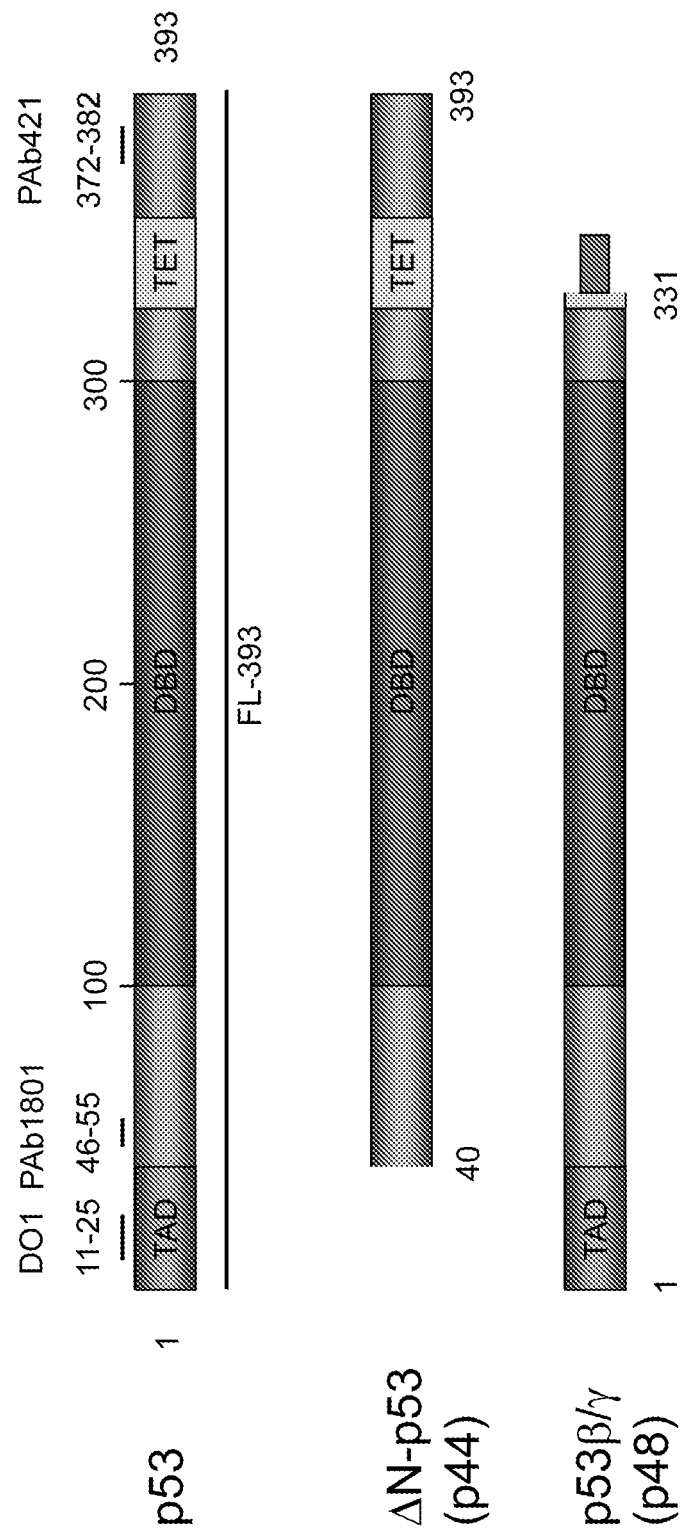
FIG. 8 shows the structural domains of wild-type p53 and two of its isoforms.

To characterize the smaller, p53-related polypeptides further, immunoblotting was performed with antibodies directed to specific epitopes of p53: D01 (residues 11-21), PAb1801 (residues 46-55) and PAb421 (residues 372-382). D01 recognized full length p53 and p48 but not p44; PAb1801 recognized full length p53, p48 and p44; and PAb421 recognized full length p53, albeit very weakly, and p44 strongly but not p48 (see FIG. 2). These epitope mapping results indicate that p44 is missing sequences at the N-terminus and that p48 is missing sequences at the C-terminus of the molecule (See FIG. 8). Moreover, they indicate that p44 and p48 are very stable relative to full length p53.

p44 likely corresponds to ΔN-p53 (also referred to as p47 or p53/p47), a previously identified isoform of p53 that is produced by internal initiation of translation at codon 40 in human p53 mRNA (see, e.g., Bourdon et al., 2005; Courtois et al., 2002; Ghosh et al., 2004; Ray et al., 2006; and Yin et al., 2002). A ΔN-p53 isoform was initially detected in a mouse erythroleukemia cell line with an internal deletion that removed all of exon 2 including the translation initiation site. Translation, initiating at the next available ATG codon in exon 4 (Met41), produces a 44-kDa protein (see, e.g., Rovinski et al., 1987). This is the corresponding ATG codon in mouse p53 that gives rise to ΔN-p53 in human cells. ΔN-p53 lacks the N-terminal Mdm2 binding site and as a result will not undergo Mdm2-mediated ubiquitination and degradation resulting in increased stability.

p48 likely corresponds to p53β (also named p53i9) or p53γ, two C-terminally truncated p53 variants produced by alternative splicing of exon 9 to one of two sites in intron 9

(see, e.g., Bourdon et al., 2005; and Flaman et al., 1996). Both p53β and p53γ terminate at Gln331 of p53 and lack amino acids 332-393 that include the oligomerization domain of p53; p53β has 10 additional amino acids and p53γ has 15 additional amino acids derived from intron 9 sequences. These experiments were unable to distinguish between these two p53 variants. The elevated level of p53β/γ in unstressed cells suggests that the last 62 amino acids of p53 contain key lysine residues for ubiquitination.

These results demonstrate that two distinct p53 isoforms can be expressed at the protein level in MCF7 cells when PMOs are used to interfere with translation initiation at codon 1 or with splicing at the splice acceptor site of exon 10.

Example 2

PMOs Block p53 Expression and p21 Induction after DNA Damage

To investigate the expression and function of p44 (ΔN-p53) and p48 (p53β/γ) isoforms in a broader range of cells under different stress conditions that activate p53, human H460 lung cancer cells were treated with doxorubicin, human HCT116 colon cancer cells were treated with 5-FU, and human OCI/AML-3 and OCI/AML-4 leukemia cells were treated with γ-radiation. All of these human cancer cell lines express wild-type p53 and respond to DNA damage by increasing p53 protein levels and activating expression of the p53-target gene, p21 (see FIG. 2).

Figure 2:
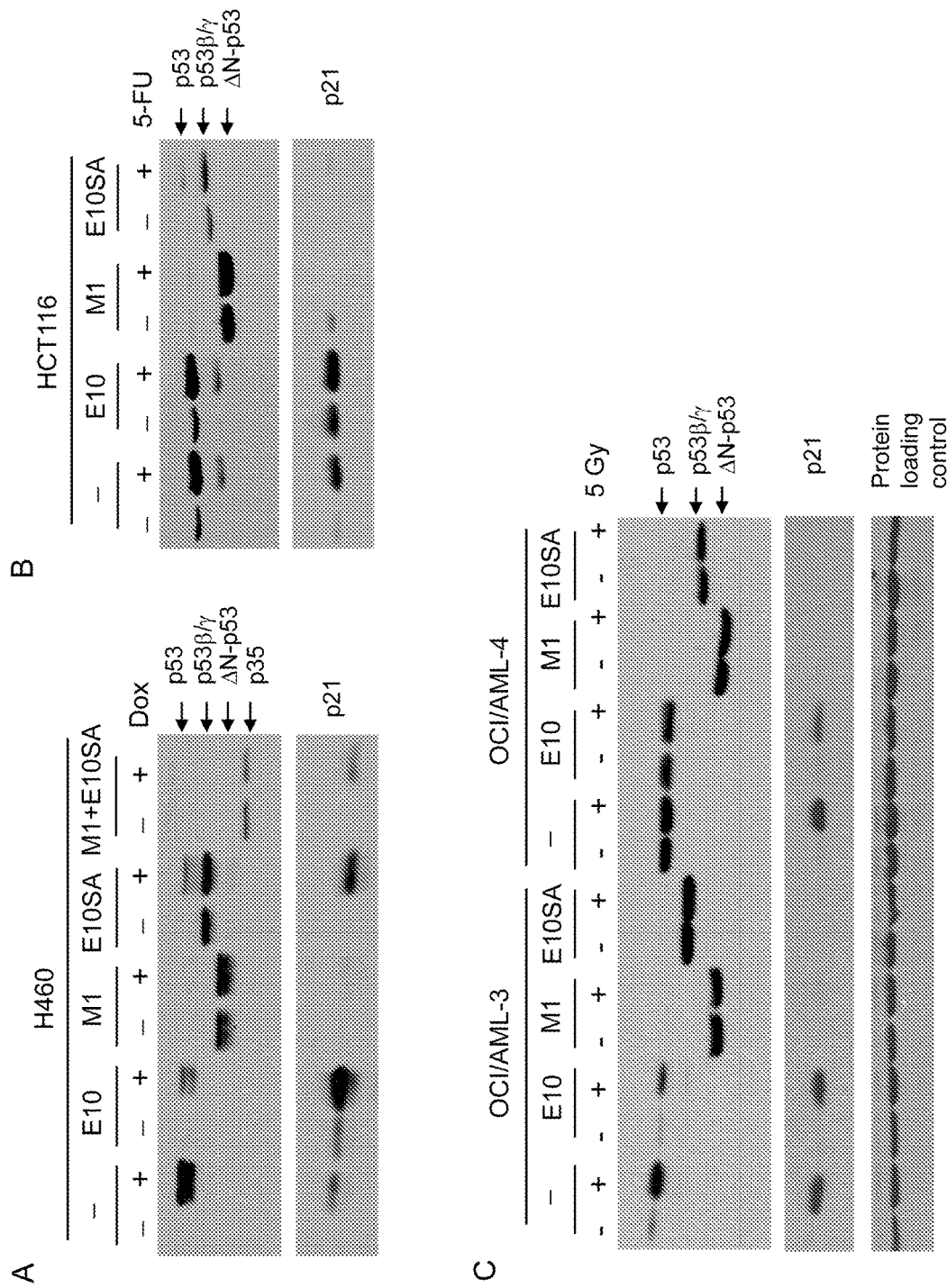
FIGS. 2A-2C show that PMOs interfere with p53 expression, increase expression of p53 isoforms and prevent induction of p21 in stressed and non-stressed cells.

As shown in FIG. 2, pre-treatment for 2 hours with peptide-conjugated M1 or E10SA prior to DNA damage led to the production of ΔN-p53 and p53β/γ, respectively, as seen previously in MCF7 cells. The levels of these stable p53 isoforms did not increase further after DNA damage. Both M1 and E10SA interfered with the accumulation of full-length p53 and with the induction of p21 after DNA damage. This was most evident in the OCI/AML cells and in the HCT116 cells. The reduced level of p21 induction in doxorubicin-treated H460 cells exposed to E10SA likely represents the effect of residual full length p53 protein. CP-conjugated E10 had no effect on p53 expression or p21 induction. Together, these results indicate that ΔN-p53 and p53β/γ lack transcriptional activity at the p21 promoter.

Also, when H460 cells were pre-treated with both M1 to block translation initiation at Men and E10SA to block splicing from exon 9 to exon 10, a novel variant of about 35 kDa was detected. It is predicted that this variant is missing the N-terminal and C-terminal regions of p53 (ΔN-p53β/γ) and that it should be missing the N-terminal transactivation domain as well as the C-terminal oligomerization domain of p53. This stable variant was present at similar levels in both doxorubicin-treated and untreated cells that had been pre-treated with M1 and E10SA Example 3

Evaluation of PMOs that Target p53 mRNA Splicing

In the following experiments, a panel peptide-conjugated PMOs was tested that target splice sites in exons 2, 4, 6, 7 and 9 of the human p53 gene (see Table A, in Example 1 above). With the exception of E2SD that targets the splice donor site of exon 2, the remaining PMOs exhibited variable effectiveness in suppressing p53 protein expression in H460 cells, revealed no new isoforms, and did not block expression of p21 in response to doxorubicin (see FIG. 3).

Figure 3:
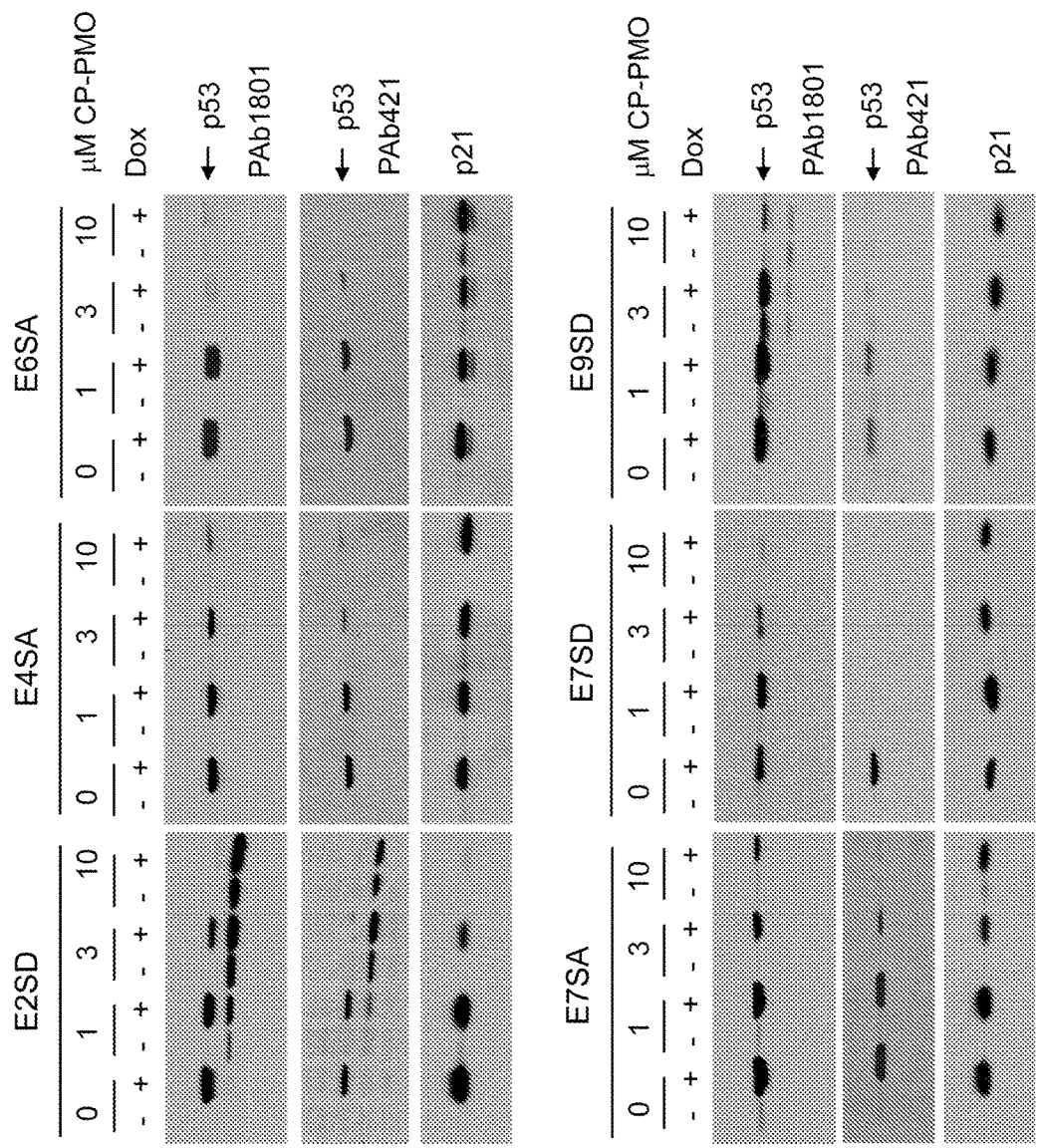
FIG. 3 shows the effect of various PMOs that target p53 pre-mRNA splicing, by western blot analysis of p53 and p21 expression in H460 cells treated with doxorubicin (200 ng/ml) for 24 hours. Cells were pre-treated with the indicated, cell-conjugated PMOs for 2 hours prior to doxorubicin treatment.

As shown in FIG. 3, E2SD produced a 44 kDa isoform that resembled ΔN-p53 and prevented the induction of p21 in response to doxorubicin treatment. This alternatively spliced transcript contains an intron 2-derived in-frame termination codon that arrests translation prematurely and was predicted to produce ΔN-p53 from codon 40. These findings suggest that E2SD and M1 produce identical truncated ΔN-p53 proteins through two different mechanisms: alternative splicing of exon 2 and alternative initiation of translation at codon 40.

Example 4

Complete Repression of p53 Expression with PMOs that Target the Translational Start Codon (Met1) and Met40

Because the inhibition of stress-induced p53 expression has potential clinical use in various pathologies including cancer, it is worth identifying PMOs that effectively block p53 expression, and also expression of certain of its isoforms. Although M1 and E2SD prevent expression of full-length p53 and allow the expression of ΔN-p53 protein, which lacks transcriptional activity at the p21 promoter, there are concerns that the N-terminally truncated p53 protein might retain transcriptional activity on other promoters or that it might possess novel and unanticipated functions (see Harms and Chen, 2006). Moreover, ΔN-p53 retains the oligomerization domain of p53 and might, therefore, function as a trans-dominant repressor of p53 family members including p63 or p73. Transgenic mice generated by microinjection of the genomic fragment encoding mouse p44 show early signs of aging and reduced body size and interestingly, this phenotype is dependent on p53 (see Maier et al., 2004). Because ΔN-p53 can form hetero-tetramers with p53, it is possible that these hetero-tetramers are responsible for the mouse phenotype. Maier et al. (2004) reported that mouse p44 has both positive and negative effects on the transcription regulatory functions of p53 depending on the specific target gene. They concluded that p44 has both dominant and dominant-negative effects on the function of full-length p53.

E10SA also prevents expression of full-length p53 but gives rise to p53β/γ. Although p53β/γ lacks the oligomerization domain and was reported to lack transcriptional activity, it retains the ability to bind certain p53-response elements on DNA (Bourdon et al., 2005). Benefits may therefore be obtained by designing intervention strategies that not only reduce expression of full-length p53, but also reduce expression of ΔN-p53, p53β/γ, or both.

A PMO-based strategy was thus designed to block translation from codon 1 and codon 40 (within exon 4) of full-length p53. When the methionine (AUG) codons at positions 1 are 40 are bypassed, the next available methionine codon bearing a Kozak consensus sequence for translation initiation occurs in codon 160 (within exon 5). A p53 mRNA variant that initiates at intron 4 from an internal promoter was previously identified and predicted to initiate translation at codon 133 giving rise to Δ133p53 (Bourdon et al., 2005). Whether either of the predicted variants (initiation from codon 133 or codon 160) is expressed at the protein level under physiological or stress conditions is not known.

A peptide-conjugated PMO that targets codon 40 of p53 mRNA (M40) was first designed and tested for its ability to repress p53 expression. When used alone, M40 repressed expression of full length p53 in a dose-dependent manner presumably through steric hindrance of the translation elongation machinery, and produced a novel polypeptide of about 35 kDa that was recognized by DO1 and FL393 but not PAb1801 (see FIGS. 4A and 4B). This could reflect translation of a splicing variant that contains exon 2 sequences (DO1 epitope) and which is missing exon 4 sequences (PAb1801 epitope). p21 expression was suppressed but not eliminated by M40 even when used at high concentration (10 µM).

Figure 4:
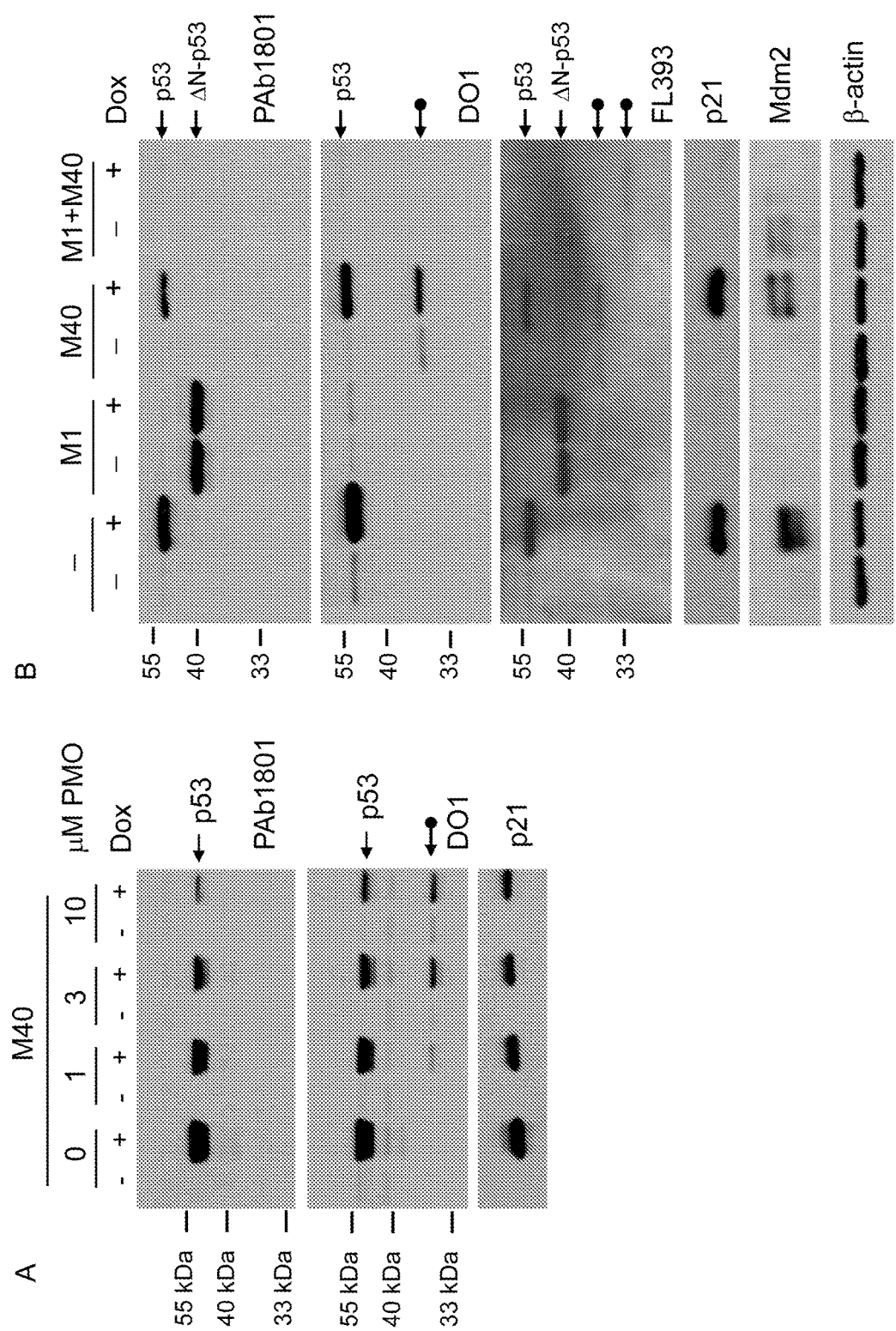
FIG. 4 shows that the combined use of M1 and M40 blocks p53 expression.

When M40 was used together with M1, however, complete suppression of p53 and ΔN-p53 was observed (see FIG. 4B). This result confirms that ΔN-p53 initiates from codon 40. A smaller polypeptide of about 33 kDa was detected very weakly by FL393 (and not by PAb1801 or DO1) in H460 cells treated with M1 and M40. This could represent a p53 translation product initiating from codon 133 (Δ133p53) or codon 160. The Western blot presented in FIG. 4B confirms that M1 prevents induction of p21 after DNA damage and additionally shows that M1 prevents induction of another p53 target gene, Mdm2. The combination of M1 and M40 prevented p21 and Mdm2 induction. Based on these results, the combined use of M1 and M40 CP-PMOs provides an effective strategy to block both full-length p53 and ΔN-p53 protein expression and p53 transcriptional activity in human cells.

Example 5

PMO-Mediated Repression of p53 Disrupts p53-Dependent Cell Cycle Arrest in G1 and p53-Dependent Apoptosis To determine the consequences of using PMOs to repress p53 expression, the ability of p53 to block cell cycle progression and to promote apoptosis in response to DNA damage was examined. First, a pair of isogenic colon cancer cell lines, HCT116 p53+/+ and HCT116 p53−/−, with 5-FU (50 µg/ml) were treated for 48 hours and the subjected to flow cytometry. A proportion of the p53+/+ cells but not the p53−/− cells had a sub-G1 DNA content characteristic of apoptotic cells (see FIG. 5A). This result confirmed that HCT116 cells undergo p53-dependent apoptosis in response to 5-FU (see Bunz et al., 1999).

Next, a comparison was made on the apoptotic response of HCT116 p53+/+ cells to 5-FU between the effect of E10, which is unable to block p53 expression, and M1 and E10SA, which do block p53 expression. Pre-treatment of these cells with M1 or E10SA but not E10 blocked p53-dependent apoptosis in these cells (see FIG. 5A). These results also indicate that ΔN-p53 (produced in response to M1) and p53β/γ (produced in response to E10SA) are defective in promoting apoptosis in H460 cells.

Figure 5:
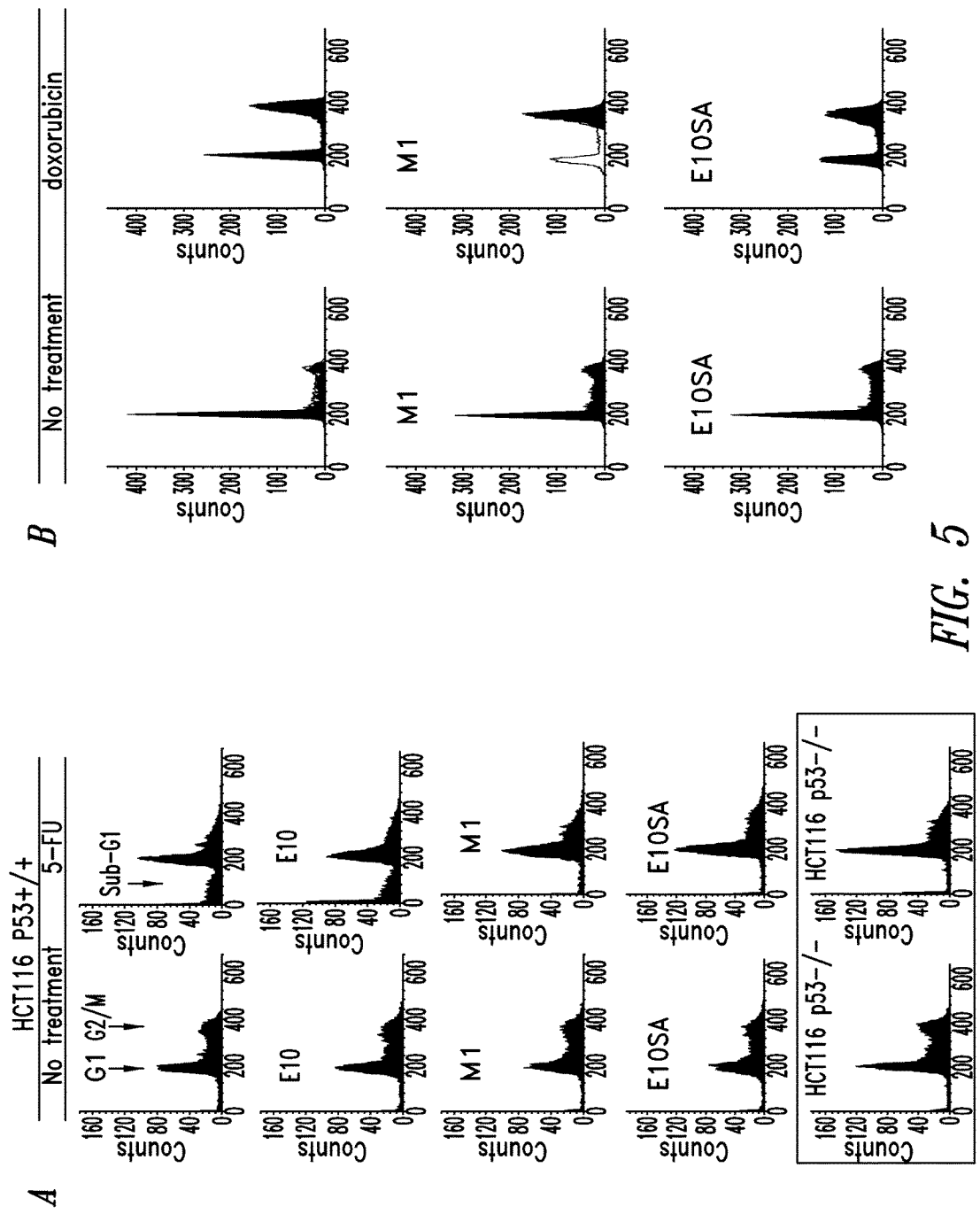
FIG. 5 shows that M1 and E10SA disrupt the apoptotic and cell cycle arrest functions of p53.

In contrast to HCT116 cells treated with 5-FU, H460 cells treated with doxorubicin (200 ng/ml) for 48 hours undergo predominantly cell cycle arrest in G1 and G2/M and not cell death (see FIG. 5B). In the absence of doxorubicin, peptide-conjugated M1 and E10SA had no effect on the cell cycle profile of H460 cells. In the presence of doxorubicin, however, both M1 and E10SA reduced the proportion of cells undergoing G1 arrest with no detectable effect on G2/M arrest (see FIG. 5B). This indicates that H460 cells undergo p53-dependent G1 arrest. In addition, these results indicate that ΔN-p53 and p53β/γ are defective at promoting cell cycle arrest. Together, these assays using 5-FU-treated HCT116 cells and doxorubicin-treated H460 cells indicate that M1 and E10SA independently suppress p53-dependent cellular responses.

The N-terminus of p53 is reported to contain two independent transcription activation (TA) domains, TA1 (~residues 1-40) and TA2 (~residues 43-63). ΔN-p53 is missing TA1 but retains TA2. Previous studies (Yin et al., 2002; Zhu et al., 1998) reported that ectopic expression of ΔN-p53 activates a subset of p53 target genes including Mdm2 and Bax through TA2; moreover, ΔN-p53 retains the ability to induce apoptosis. Taken together, these results show that endogenously expressed ΔN-p53 lacks the ability to activate p21 and Mdm2 expression in stressed or unstressed H460 cells (FIG. 4B) and lacks the ability to promote apoptosis in response to DNA damage (FIG. 5A).

Example 6

PMO-Mediated Repression of p53 Sensitizes H460 Cells to Doxorubicin-Induced Apoptosis The role of p53 in determining the cellular response to chemotherapeutic drug treatment is complex and can be dependent on cell type and the drug used (Bunz et al., 1999). In some experimental models, p53-deficiency is associated with resistance to DNA damaging agents, whereas in other models p53-deficiency leads to enhanced sensitivity to drug killing. It remains unclear how p53 determines strikingly different cellular responses to DNA damage and how these responses affect drug sensitivity in a clinical setting. p53-dependent cell cycle arrest in response to DNA damage could provide cells with time to repair the damage prior to DNA synthesis or cell division. In addition, p53 can regulate the expression of anti-oxidant genes, metabolic genes and DNA repair genes that may influence drug sensitivity and cell survival (Vousden and Prives, 2009). The pro-survival function of p53 could mitigate the effects of chemotherapy on tumour cells with wild-type p53 (Kim et al., 2009).

To determine if p53 plays a role in determining the sensitivity of H460 cells to doxorubicin, PMOs were used to repress p53 expression prior to treatment with doxorubicin. H460 cells were pre-treated with M1 alone, M40 alone or both M1 and M40 prior to treatment with doxorubicin (200 ng/ml) for 72 hours. Apoptosis was measured using propidium iodide staining and flow cytometry to identify cells with sub-G1 DNA content (FIGS. 6A and 6B) or by using a highly sensitive assay that measures caspase 3 activation (FIG. 6C).

Figure 6:
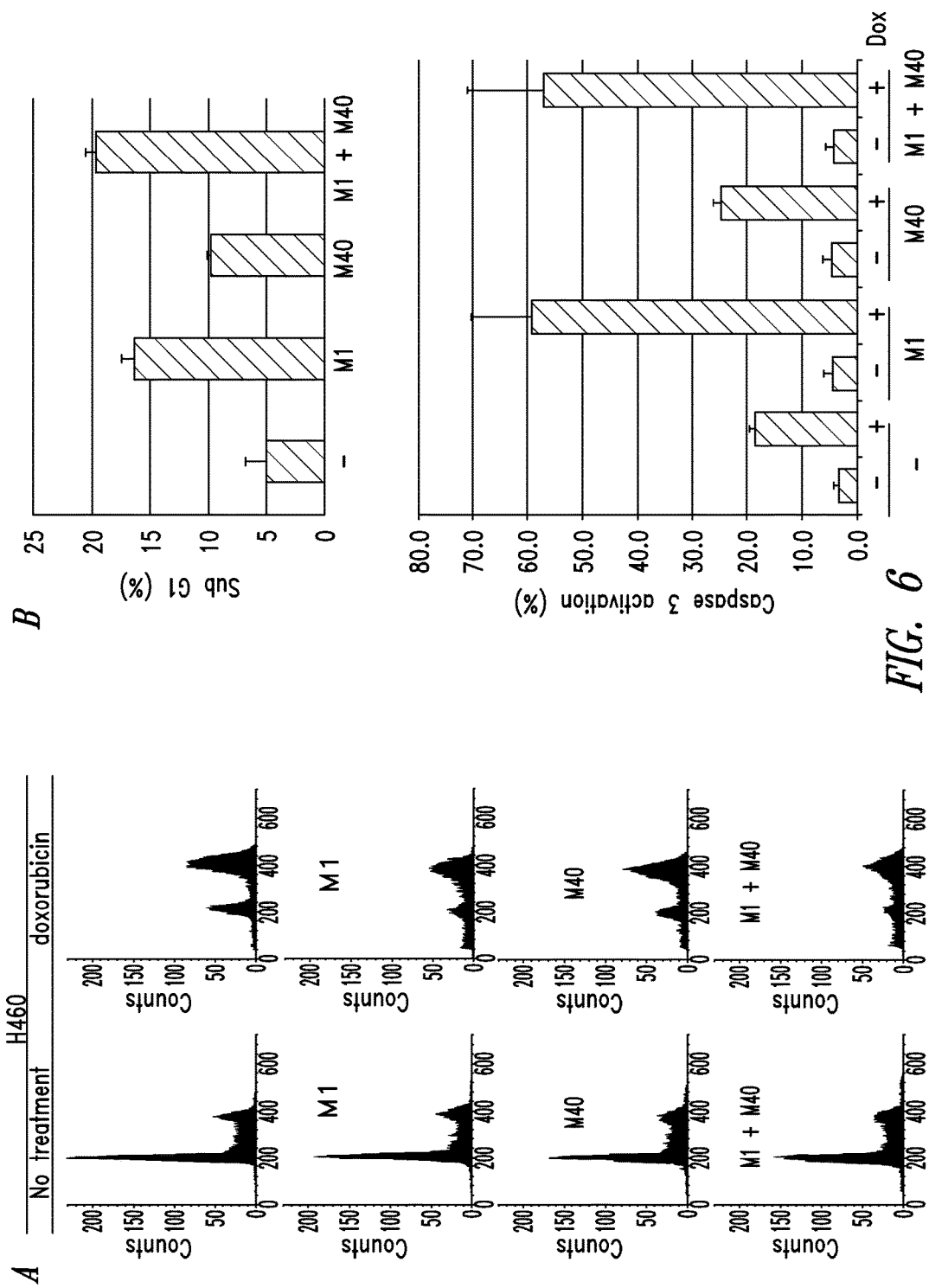
FIG. 6 shows that inhibition of p53 expression sensitizes H460 cells to doxorubicin-induced apoptosis.
Figure 7:
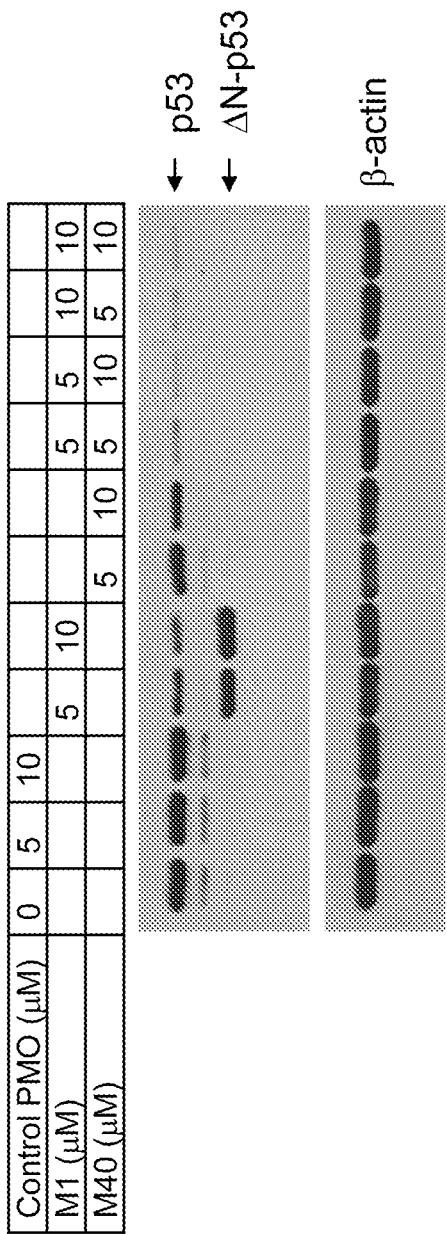
FIG. 7 shows that M1 and M40 inhibit mutant p53 expression in MDA-MB-468 breast cancer cells, by western blot analysis of p53 expression in human breast cancer MDA-MB-468 cells. Targeting M1 with PMO increases translation of the deltaN-p53 isoform. Cells were treated with peptide-conjugated PMOs as indicated for 2 hours. Cells were collected 24 hours after treatment and protein extracts were analyzed by Western blotting with antibodies to p53 (PAb1801) or β-actin as a loading control.

In the experiments described in FIG. 5B, H460 cells were treated with doxorubicin for 48 hours and observed predominantly cell cycle arrest. After longer treatment (72 hours), a small proportion of apoptotic cells could be detected (FIG. 6). Both apoptotic assays indicated a significant enhancement (3-fold) of doxorubicin-induced apoptosis when M1 was used to block p53 expression. The combined use of M1 and M40 was not more effective than M1 alone in sensitizing H460 cells to doxorubicin-induced cell death indicating that ΔN-p53 (produced by M1) is defective in promoting survival. However, repression of ΔN-p53 could provide other advantages, discussed herein.

These results unmask a pro-survival function of full-length wild-type p53 in H460 cells that limits the effectiveness of doxorubicin in killing these cancer cells. Hence, in certain tumour cells where the predominant response to p53 activation is not apoptosis but rather survival, the inhibition of p53's protective function may render these cells sensitive to drugs that promote cell death through p53-independent processes.

A number of strategies have been proposed to exploit the defective G1 checkpoint status of cancer cells with inactive mutant p53 (see, e.g., Wang and E1-Deiry, 2004; Wiman, 2006). These studies suggest that such strategies could be applied more broadly to include cancers that retain wild-type p53 alleles through the use of PMOs to block p53 expression in these tumours.

Example 7

The Combined Use of M1 and M40 Blocks Mutant p53 Expression in MDA-MB-468 Breast Carcinoma Cells Unlike mutations in other tumour suppressor genes, most p53 mutations in human cancer are missense mutations that lead to the synthesis of stable but defective p53 protein. The retention of mutant p53 in human tumours rather than complete loss of p53 could reflect a gain of function for mutant p53. The generation of mutant p53 knock-in mice that display aggressive and metastatic tumours not seen in p53-null mice provides strong support for this idea (Lang et al., 2004; Olive et al., 2004). Furthermore, mutant p53 expression has been associated with increased cell proliferation, migration, invasion and metastasis through the suppression of p63 (Adorno et al., 2009). These findings suggest that targeting mutant p53 in highly aggressive human tumours could have therapeutic potential.

To test the ability of M1 and M40 to inhibit mutant p53 expression, the breast carcinoma cell line MDA-MB-468 that expresses mutant (R273H) p53 was treated with peptide-conjugated PMOs. M1 treatment inhibited full length p53 expression and produced ΔN-p53. When used together, M1 and M40 reduced full length p53 without producing ΔN-p53. These data indicate that M1 and M40 are effective at blocking mutant p53 expression in human tumour cells.

Much of the evidence for the various p53 isoforms is theoretical and based on RT-PCR analysis and ectopic expression of cDNAs constructs. Endogenous expression of only a few of the reported human p53 isoforms has been detected unambiguously at the protein level. The PMOs described herein provide valuable reagents to investigate the structure and function of p53 isoforms that arise naturally upon targeted disruption of splicing or translation. One finding is the resiliency of p53 expression in response to various efforts to block its expression. It is notable that truncated p53 variants observed herein are more stable than full-length p53 in unstressed cells including ΔN-p53, p53β/γ, and the smaller ΔN-p53β/γ and putative Δ133p53.

Transient p53 repression may be beneficial not only in tumour cells but also as a means of limiting normal tissue damage in response to irradiation or chemotherapy. Reducing p53 induction may also be therapeutically beneficial during ischemia or during subsequent reperfusion injury and in various neurodegenerative diseases.

Example 8

Antisense Oligonucleotides with Complementarity to Insulin Degrading Enzyme

Insulin degrading enzyme (IDE) is a zinc metallopeptidase that regulates both cerebral amyloid β-peptide and plasma insulin levels. A single transcript encoding IDE has two characterized alternative translation initiation codons—an first AUG (AUG1) at the first methionine (M1) and a downstream AUG (AUG2) at residue 42 (M42). The IDE isoform translated from M1 (Met$^1$-IDE) localizes to the mitochondria, while the IDE isoform translated from M42 (Met$^2$-IDE) localizes to the cytoplasm. Furthermore, some observations indicate that mitochondrial localization of IDE may be linked to type II diabetes mellitus (DMII) and Alzheimer's disease (AD). An antisense oligonucleotide can be designed to hybridize with the start codon encoding M1 in order to inhibit Met$^1$-IDE and treat DMII and/or AD. The antisense oligonucleotide comprising a sequence complementary to the start codon encoding M1 can be designed to comprise a sequence complementary to the sequence TGGCTA<u>AUG</u>C (SEQ ID NO: 30) or a portion thereof comprising the AUG of M1 (underlined). The antisense oligonucleotide will switch translation to the downstream AUG start codon (Met$^2$-IDE) relative to the upstream AUG (Met$^1$-IDE).

Example 9

Antisense Oligonucleotides with Complementarity to TAR DNA-Binding Protein mRNA

The TAR DNA binding protein-43 (TDP-43) is a major component of the ubiquitin-positive inclusions found in neurodegenerative disease collectively termed TDP-43 proteinopathies. Amyotrophic lateral sclerosis (ALS), survival motor neuron (SMN), and spinal muscle atrophy (SMA) are all linked to the TDP-43 proteinopathies. Three alternate translation start sites for TDP-43 resulting in 43 kDa, 35 kDa, and 25 kDa proteins have been observed. The third in-frame methionine of TDP-43 (Met85) is the start site for the 35 kDa protein isoform, which accumulates in "stress granules" that have been linked to neurodegeneration. An antisense oligonucleotide can be designed to hybridize with the start codon encoding Met85 in order to inhibit the 35 kDa isoform of TDP-43 and treat one or more neudegenerative diseases, such as ALS, SMN, and SMA. The antisense oligonucleotide comprising a sequence complementary to the start codon encoding Met85 can be designed to comprise a sequence complementary to the sequence AAGGAAAAUGG<u>AUG</u>AGACAGA (SEQ ID NO: 31) or a portion thereof comprising the AUG of Met85 (underlined).

Example 10

Antisense Oligonucleotides with Complementarity to Regulator of G-Protein Signaling 2

The regulator of G-protein signaling 2 (RGS2) contains two functional domains. RGS2 inhibits signal transduction from G-protein-coupled receptors, and the amino-terminal domain directs interaction with adenylyl cyclases. The two functional domains can be separated by expression from different translation start sites. For example, translation initiating from the alternative start codon encoding the methionine at amino acid position 16 (Met16) produces an RGS2 isoform that is impaired as an inhibitor of type V adenylyl cyclase. An antisense oligonucleotide can be designed to hybridize with the start codon encoding Met16 in order to inhibit the isoform of RGS2 expressed therefrom and prevent receptor desensitization or alter adenylate cyclase signaling, thereby manipulating a variety of physiological responses. The antisense oligonucleotide comprising a sequence complementary to the start codon encoding Met16 can be designed to comprise a sequence complementary to CGACUGCAGACCCAUGACAAGA (SEQ ID NO: 32) or a portion thereof comprising the AUG of Met16 (underlined).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

REFERENCES

Abes, R., Arzumanov, A., Moulton, H., Abes, S., Ivanova, G., Gait, M. J., Iversen, P. and Lebleu, B. (2008). Arginine-rich cell penetrating peptides: design, structure-activity, and applications to alter pre-mRNA splicing by steric-block oligonucleotides. J. Pept. Sci. 4, 455-460.

Adorno, M., Cordenonsi, M., Montagner, M., Dupont, S., Wong, C., Hann, B., Solari, A., Bobisse, S., Rondina, M. B., Guzzardo, V. et al. (2009). A Mutant-p53/Smad Complex Opposes p63 to Empower TGF & beta; -Induced Metastasis. Cell 1, 87-98.

Banks, L., Matlashewski, G. and Crawford, L. (1986). Isolation of human-p53-specific monoclonal antibodies and their use in the studies of human p53 expression. Eur. J. Biochem. 3, 529-534.

Bourdon, J. C., Fernandes, K., Murray-Zmijewski, F., Liu, G., Diot, A., Xirodimas, D. P., Saville, M. K. and Lane, D. P. (2005). p53 Isoforms can Regulate p53 Transcriptional Activity. Genes Dev. 18, 2122-2137.

Bunz, F., Hwang, P. M., Torrance, C., Waldman, T., Zhang, Y., Dillehay, L., Williams, J., Lengauer, C., Kinzler, K. W. and Vogelstein, B. (1999). Disruption of p53 in human cancer cells alters the responses to therapeutic agents. J. Clin. Invest. 3, 263-269.

Courtois, S., Verhaegh, G., North, S., Luciani, M. G., Lassus, P., Hibner, U., Oren, M. and Hainaut, P. (2002). DeltaN-p53, a natural isoform of p53 lacking the first transactivation domain, counteracts growth suppression by wild-type p53. Oncogene 44, 6722-6728.

Flaman, J. M., Waridel, F., Estreicher, A., Vannier, A., Limacher, J. M., Gilbert, D., Iggo, R. and Frebourg, T. (1996). The human tumour suppressor gene p53 is alternatively spliced in normal cells. Oncogene 4, 813-818.

Ghosh, A., Stewart, D. and Matlashewski, G. (2004). Regulation of human p53 activity and cell localization by alternative splicing. Mol. Cell. Biol. 18, 7987-7997.

Harlow, E., Crawford, L. V., Pim, D. C. and Williamson, N. M. (1981). Monoclonal antibodies specific for simian virus 40 tumor antigens. J. Virol. 3, 861-869.

Harms, K. L. and Chen, X. (2006). The functional domains in p53 family proteins exhibit both common and distinct properties. Cell Death Differ. 6, 890-897.

Iversen, P. L. (2001). Phosphorodiamidate morpholino oligomers: favorable properties for sequence-specific gene inactivation. Curr. Opin. Mol. Ther. 3, 235-238.

Kim, E., Giese, A. and Deppert, W. (2009). Wild-type p53 in cancer cells: when a guardian turns into a blackguard. Biochem. Pharmacol. I, 11-20.

Lang, G. A., Iwakuma, T., Suh, Y. A., Liu, G., Rao, V. A., Parant, J. M., Valentin-Vega, Y. A., Terzian, T., Caldwell, L. C., Strong, L. C., El-Naggar, A. K. and Lozano, G. (2004). Gain of function of a p53 hot spot mutation in a mouse model of Li-Fraumeni syndrome. Cell 6, 861-872.

Maier, B., Gluba, W., Bernier, B., Turner, T., Mohammad, K., Guise, T., Sutherland, A., Thorner, M. and Scrable, H. (2004). Modulation of mammalian life span by the short isoform of p53. Genes Dev. 3, 306-319.

Nelson, M. H., Stein, D. A., Kroeker, A. D., Hatlevig, S. A., Iversen, P. L. and Moulton, H. M. (2005). Arginine-rich peptide conjugation to morpholino oligomers: effects on antisense activity and specificity. Bioconjug. Chem. 4, 959-966.

Olive, K. P., Tuveson, D. A., Ruhe, Z. C., Yin, B., Willis, N. A., Bronson, R. T., Crowley, D. and Jacks, T. (2004). Mutant p53 gain of function in two mouse models of Li-Fraumeni syndrome. Cell 6, 847-860.

Ray, P. S., Grover, R. and Das, S. (2006). Two internal ribosome entry sites mediate the translation of p53 isoforms. EMBO Rep. 4, 404-410.

Rovinski, B., Munroe, D., Peacock, J., Mowat, M., Bernstein, A. and Benchimol, S. (1987). Deletion of 5'-coding sequences of the cellular p53 gene in mouse erythroleukemia: a novel mechanism of oncogene regulation. Mol. Cell. Biol. 2, 847-853.

Summerton, J. and Weller, D. (1997). Morpholino antisense oligomers: design, preparation, and properties. Antisense Nucleic Acid Drug Dev. 3, 187-195.

Vousden, K. H. and Prives, C. (2009). Blinded by the Light: The Growing Complexity of p53. Cell 3, 413-431.

Wang, C., Curtis, J. E., Minden, M. D. and McCulloch, E. A. (1989). Expression of a retinoic acid receptor gene in myeloid leukemia cells. Leukemia 4, 264-269.

Wang, S, and El-Deiry, W. S. (2004). The p53 pathway: targets for the development of novel cancer therapeutics. Cancer Treat. Res. 175-187.

Wiman, K. G. (2006). Strategies for therapeutic targeting of the p53 pathway in cancer. Cell Death Differ. 6, 921-926.

Wu, R. P., Youngblood, D. S., Hassinger, J. N., Lovejoy, C. E., Nelson, M. H., Iversen, P. L. and Moulton, H. M. (2007). Cell-penetrating peptides as transporters for morpholino oligomers: effects of amino acid composition on intracellular delivery and cytotoxicity. Nucleic Acids Res. 15, 5182-5191.

Yin, Y., Stephen, C. W., Luciani, M. G. and Fahraeus, R. (2002). p53 Stability and activity is regulated by Mdm2-mediated induction of alternative p53 translation products. Nat. Cell Biol. 6, 462-467.

Zhu, J., Zhou, W., Jiang, J. and Chen, X. (1998). Identification of a novel p53 functional domain that is necessary for mediating apoptosis. J. Biol. Chem. 21, 13030-13036.

The invention claimed is:

1. An isolated antisense phosphorodiamidate morpholino oligonucleotide of 22 to 25 bases comprising the base sequence SEQ ID NO:4 (M40).

2. The isolated antisense phosphorodiamidate morpholino oligonucleotide of claim 1, wherein the antisense phosphorodiamidate morpholino oligonucleotide has a base sequence that is 100% complementary to contiguous bases surrounding a second translation start codon of a p53 mRNA.

3. The isolated antisense phosphorodiamidate morpholino oligonucleotide of claim 1, wherein the antisense phosphorodiamidate morpholino oligonucleotide consists of the base sequence of SEQ ID NO:4 (M40).

4. The isolated antisense phosphorodiamidate morpholino oligonucleotide of claim 1, wherein the antisense phosphorodiamidate morpholino oligonucleotide is a phosphorodiamidate morpholino oligonucleotide comprising one or more piperazine-containing intersubunit linkages, one or more PMO-X linkages, or a combination thereof.

5. The isolated antisense phosphorodiamidate morpholino oligonucleotide of claim 1, wherein the antisense phosphorodiamidate morpholino oligonucleotide is a phosphorodiamidate morpholino oligonucleotide comprising one or more piperazine-containing intersubunit linkages.

6. A composition for reducing expression of full-length p53 protein and at least one ΔN-p53 protein isoform thereof in a cell, comprising a first antisense phosphorodiamidate morpholino oligonucleotide and a second antisense phosphorodiamidate morpholino oligonucleotide, wherein the first antisense phosphorodiamidate morpholino oligonucleotide has 22 to 30 bases and comprises the base sequence of SEQ ID NO:3 (M1) and the second antisense phosphorodiamidate morpholino oligonucleotide has 22 to 25 bases and comprises the base sequence of SEQ ID NO:4 (M40).

7. The composition of claim 6, further comprising a chemotherapeutic, where the chemotherapeutic is a DNA intercalating agent, a topoisomerase II inhibitor, or both.

8. The composition of claim 6, wherein the first and second antisense phosphorodiamidate morpholino oligonucleotides are each a phosphorodiamidate morpholino oligonucleotide comprising one or more piperazine-containing intersubunit linkages, one or more PMO-X linkages, or a combination thereof.

9. The composition of claim 8, wherein the first and second antisense phosphorodiamidate morpholino oligonucleotides are each a phosphorodiamidate morpholino oligonucleotide comprising one or more piperazine-containing intersubunit linkages (PMOplus).

10. The composition of claim 6, wherein the first antisense phosphorodiamidate morpholino oligonucleotide consists of the base sequence of SEQ ID NO:3 and the second antisense phosphorodiamidate morpholino oligonucleotide consists of the base sequence of SEQ ID NO:4.

11. A method of inhibiting translation of an isoform of a p53 protein translated from a start codon of a p53 mRNA that comprises at least two start codons, comprising contacting a cell that expresses the p53 mRNA with an antisense phosphorodiamidate morpholino oligonucleotide of claim 1.

12. The method of claim 11, wherein the isoform is associated with a disease.

13. The method of claim 12, wherein the disease is selected from the group consisting of a proliferative disorder, a neurodegenerative disorder, an autoimmune disorder and an inflammatory disorder.

14. The method of claim 12, further comprising contacting the cell with one or more additional antisense phosphorodiamidate morpholino oligonucleotides, wherein each additional antisense phosphorodiamidate morpholino oligonucleotide comprises a base sequence that is complementary to an additional translation start codon of an additional isoform of said p53 protein encoded by said p53 mRNA, wherein said additional antisense phosphorodiamidate morpholino oligonucleotides inhibit translation of said additional isoforms of said p53 mRNA.

15. The method of claim 12, wherein the method comprises increasing the sensitivity of the cell to a chemotherapeutic, wherein the cell expresses full-length p53 protein, mutant p53 protein, or both, and wherein a predominant response of the cell to p53 expression, or p53 activation by the chemotherapeutic, is survival relative to cell-death, and wherein the method further comprises contacting the cell with the chemotherapeutic, wherein the chemotherapeutic is a DNA intercalating agent, a topoisomerase II inhibitor, or both, and wherein the antisense phosphorodiamidate morpholino oligonucleotide reduces expression of full-length p53 protein, thereby increasing sensitivity of the cell to the chemotherapeutic.

16. The method of claim 15, where the chemotherapeutic is an anthracycline antibiotic or an analog thereof.

17. A method for reducing expression of full-length p53 protein and at least one ΔN-p53 protein isoform thereof in a cell, comprising contacting a cell with a composition of claim 6, thereby reducing expression of full-length p53 protein and at least one ΔN-p53 protein isoform.

18. The method of claim 17, wherein the cell is a cancer cell.

19. The method of claim 17, wherein the cell is in a subject, and the method comprises administering the composition to the subject.

20. The method of claim 17, for sensitizing the cell to a chemotherapeutic, comprising contacting the cell with a chemotherapeutic prior to, at the same time as, or after contacting the cell with the composition, wherein the chemotherapeutic comprises a DNA intercalating agent, a topoisomerase II inhibitor, or both.

21. The method of claim 20, wherein the chemotherapeutic is an anthracycline antibiotic or an analog thereof.

22. The method of claim 17, for treating cancer, wherein the cancer is refractory or resistant to a chemotherapeutic in a p53-associated manner.

23. The method of claim 17, wherein the first antisense phosphorodiamidate morpholino oligonucleotide consists of the base sequence of SEQ ID NO:3 and the second antisense phosphorodiamidate morpholino oligonucleotide consists of the base sequence of SEQ ID NO:4.

* * * * *